(12) United States Patent
Wenzel Tornoe et al.

(10) Patent No.: US 8,299,075 B2
(45) Date of Patent: Oct. 30, 2012

(54) SUBSTITUTED THIOMORPHOLINE DERIVATIVES

(75) Inventors: Christian Wenzel Tornoe, Kgs. Lyngby (DK); Mario Rottlander, Greve (DK); Nikolay Khanzhin, Humlebaek (DK); William Patrick Watson, Coventry (GB); Andreas Ritzen, Vanlose (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 13/192,833

(22) Filed: Jul. 28, 2011

(65) Prior Publication Data

US 2011/0294787 A1 Dec. 1, 2011

Related U.S. Application Data

(60) Division of application No. 12/611,249, filed on Nov. 3, 2009, now Pat. No. 8,012,962, which is a division of application No. 12/361,404, filed on Jan. 28, 2009, now abandoned, and a division of application No. 12/361,509, filed on Jan. 28, 2009, now Pat. No. 7,632,835, said application No. 12/361,404 is a division of application No. 11/314,802, filed on Dec. 21, 2005, now Pat. No. 7,501,414, said application No. 12/361,509 is a division of application No. 11/314,802, filed on Dec. 21, 2005, now Pat. No. 7,501,414, which is a continuation of application No. PCT/DK2005/000159, filed on Mar. 9, 2005.

(60) Provisional application No. 60/552,574, filed on Mar. 12, 2004.

(30) Foreign Application Priority Data

Mar. 12, 2004 (DK) .................................. 2004 00412

(51) Int. Cl.
*A61K 31/5377* (2006.01)

(52) U.S. Cl. ................................. 514/237.2; 514/237.8

(58) Field of Classification Search ............... 514/237.2, 514/237.8
See application file for complete search history.

(56) References Cited

U.S. PATENT DOCUMENTS

| | | | |
|---|---|---|---|
| 5,688,792 A | 11/1997 | Barbachyn et al. | |
| 6,020,357 A | 2/2000 | Pinto et al. | |
| 6,187,797 B1 | 2/2001 | Pruitt et al. | |
| 6,605,609 B2 | 8/2003 | Barbachyn et al. | |
| 7,501,414 B2 | 3/2009 | Tornoe et al. | |
| 7,632,835 B2 | 12/2009 | Tornoe et al. | |
| 7,812,023 B2 | 10/2010 | Tornoe et al. | |
| 2001/0049444 A1 | 12/2001 | McNaughton-Smith et al. | |

FOREIGN PATENT DOCUMENTS

| | | |
|---|---|---|
| JP | 03175086 | 7/1991 |
| WO | 98/28269 A1 | 7/1998 |
| WO | 98/28282 A2 | 7/1998 |
| WO | 99/32454 A1 | 7/1999 |
| WO | 99/50255 A2 | 10/1999 |
| WO | 02/49628 A2 | 6/2002 |
| WO | 02/055013 A2 | 7/2002 |
| WO | 02/055014 A2 | 7/2002 |
| WO | 02/066036 A1 | 8/2002 |
| WO | 03/037871 A1 | 5/2003 |
| WO | 03/037872 A1 | 5/2003 |

OTHER PUBLICATIONS

Main M., et al., "Modulation of KCNQ2/3 Potassium Channels by the Novel Anticonvulsant Retigabine," Molecular Pharmacology, 58:2; p. 253-262, 2000.
Database Beilstein Beilstein Crossfire Institut Zur Foerderung Der Chemischen Wissenschaften, DE; BRN 6233316 1993, XP002330358, Abstract; & Verna M Al: Arch Pharm (Weinheim W Ger), 315:7; p. 358-363, 1982.

*Primary Examiner* — Kahsay T Habte
(74) *Attorney, Agent, or Firm* — Stephen G. Kalinchak; Kitae Lim; Mary Catherine Di Nunzio

(57) ABSTRACT

The present invention relates to morpholine and thiomorpholine derivatives of the general formula I or pharmaceutically acceptable salts thereof and their use.

11 Claims, No Drawings

SUBSTITUTED THIOMORPHOLINE DERIVATIVES

CROSS-REFERENCE TO RELATED APPLICATION

The present application is a U.S. divisional patent application that claims the benefit of U.S. patent application Ser. No. 12/611,249, filed on Nov. 3, 2009, which is a U.S. divisional application of U.S. patent application Ser. Nos. 12/361,404 and 12/361,509 (now, U.S. Pat. No. 7,632,835), filed on Jan. 28, 2009, which are U.S. divisional patent applications of U.S. patent application Ser. No. 11/314,802 (now, U.S. Pat. No. 7,501,414), filed Dec. 21, 2005, which is a §365(c) continuation of PCT International Application No. PCT/DK2005/000159, filed Mar. 9, 2005, which claims the benefit of priority of U.S. Provisional Application No. 60/552,574 and Danish Application No. PA200400412, both filed Mar. 12, 2004. Each of the foregoing is herein incorporated by reference in its entirety.

FIELD OF THE INVENTION

The present invention relates to novel substituted morpholine and thiomorpholine derivatives being openers of the KCNQ family potassium ion channels. The compounds are useful in the treatment of disorders and diseases being responsive to opening of the KCNQ family potassium ion channels, one such disease is epilepsy.

BACKGROUND OF THE INVENTION

Ion channels are cellular proteins that regulate the flow of ions, including potassium, calcium, chloride and sodium into and out of cells. Such channels are present in all animal and human cells and affect a variety of processes including neuronal transmission, muscle contraction, and cellular secretion.

Humans have over 70 genes encoding potassium channel subtypes (Jentsch *Nature Reviews Neuroscience* 2000, 1, 21-30) with a great diversity with regard to both structure and function. Neuronal potassium channels, which are found in the brain, are primarily responsible for maintaining a negative resting membrane potential, as well as controlling membrane repolarisation following an action potential.

One subset of potassium channel genes is the KCNQ family. Mutations in four out of five KCNQ genes have been shown to underlie diseases including cardiac arrhythmias, deafness and epilepsy (Jentsch *Nature Reviews Neuroscience* 2000, 1, 21-30).

The KCNQ4 gene is thought to encode the molecular correlate of potassium channels found in outer hair cells of the cochlea and in Type I hair cells of the vestibular apparatus, in which mutations can lead to a form of inherited deafness.

KCNQ1 (KvLQT1) is co-assembled with the product of the KCNE1 (minimal K(+)-channel protein) gene in the heart to form a cardiac-delayed rectifier-like K(+) current. Mutations in this channel can cause one form of inherited long QT syndrome type 1 (LQT1), as well as being associated with a form of deafness (Robbins *Pharmacol Ther* 2001, 90, 1-19).

The genes KCNQ2 and KCNQ3 were discovered in 1988 and appear to be mutated in an inherited form of epilepsy known as benign familial neonatal convulsions (Rogawski *Trends in Neurosciences* 2000, 23, 393-398). The proteins encoded by the KCNQ2 and KCNQ3 genes are localised in the pyramidal neurons of the human cortex and hippocampus, regions of the brain associated with seizure generation and propagation (Cooper et al. *Proceedings National Academy of Science USA* 2000, 97, 4914-4919).

KCNQ2 and KCNQ3 are two potassium channel subunits that form "M-currents" when expressed in vitro. The M-current is a non-inactivating potassium current found in many neuronal cell types. In each cell type, it is dominant in controlling membrane excitability by being the only sustained current in the range of action potential initiation (Marrion *Annual Review Physiology* 1997, 59, 483-504). Modulation of the M-current has dramatic effects on neuronal excitability, for example activation of the current will reduce neuronal excitability. Openers of these KCNQ channels or activators of the M-current, will reduce excessive neuronal activity and may thus be of use in the treatment of seizures and other diseases and disorders characterised by excessive neuronal activity, such as neuronal hyperexcitability including convulsive disorders, epilepsy and neuropathic pain.

Retigabine (D-23129; N-(2-amino-4-(4-fluorobenzylamino)-phenyl) carbamic acid ethyl ester) and analogues thereof are disclosed in EP554543. Retigabine is an anticonvulsive compound with a broad spectrum and potent anticonvulsant properties, both in vitro and in vivo. It is active after oral and intraperitoneal administration in rats and mice in a range of anticonvulsant tests including: electrically induced seizures, seizures induced chemically by pentylenetetrazole, picrotoxin and N-methyl-D-aspartate (NMDA) and in a genetic animal model, the DBA/2 mouse (Rostock et al. *Epilepsy Research* 1996, 23, 211-223). In addition, retigabine is active in the amygdala kindling model of complex partial seizures, further indicating that this compound has potential for anti-convulsive therapy. In clinical trials, retigabine has recently shown effectiveness in reducing the incidence of seizures in epileptic patients (Bialer et al. *Epilepsy Research* 2002, 51, 31-71).

Retigabine has been shown to activate a K(+) current in neuronal cells and the pharmacology of this induced current displays concordance with the published pharmacology of the M-channel, which recently was correlated to the KCNQ2/3 K(+) channel heteromultimer. This suggests that activation of KCNQ2/3 channels may be responsible for some of the anticonvulsant activity of this agent (Wickenden et al. *Molecular Pharmacology* 2000, 58, 591-600)—and that other agents working by the same mechanism may have similar uses.

KCNQ 2 and 3 channels have also been reported to be upregulated in models of neuropathic pain (Wickenden et al. *Society for Neuroscience Abstracts* 2002, 454.7), and potassium channel modulators have been hypothesised to be active in both neuropathic pain and epilepsy (Schroder et al. *Neuropharmacology* 2001, 40, 888-898).

Retigabine has also been shown to be beneficial in animal models of neuropathic pain (Blackburn-Munro and Jensen *European Journal of Pharmacology* 2003, 460, 109-116), and it is thus suggested that openers of KCNQ channels will be of use in treating pain disorders including neuropathic pain.

The localisation of KCNQ channel mRNA is reported in brain and other central nervous system areas associated with pain (Goldstein et al. *Society for Neuroscience Abstracts* 2003, 53.8).

In addition to a role in neuropathic pain, the expression of mRNA for KCNQ 2-5 in the trigeminal and dorsal root ganglia and in the trigeminal nucleus caudalis implies that openers of these channels may also affect the sensory processing of migraine pain (Goldstein et al. *Society for Neuroscience Abstracts* 2003, 53.8).

Recent reports demonstrate that mRNA for KCNQ 3 and 5, in addition to that for KCNQ2, are expressed in astrocytes and glial cells. Thus KCNQ 2, 3 and 5 channels may help modulate synaptic activity in the CNS and contribute to the neuroprotective effects of KCNQ channel openers (Noda et al., *Society for Neuroscience Abstracts* 2003, 53.9).

Retigabine and other KCNQ modulators may thus exhibit protection against the neurodegenerative aspects of epilepsy, as retigabine has been shown to prevent limbic neurodegeneration and the expression of markers of apoptosis following kainic acid-induced status epilepticus in the rat (Ebert et al. *Epilepsia* 2002, 43 Suppl 5, 86-95). This may have relevance for preventing the progression of epilepsy in patients, i.e. be anti-epileptogenic. Retigabine has also been shown to delay the progression of hippocampal kindling in the rat, a further model of epilepsy development (Tober et al. *European Journal Of Pharmacology* 1996, 303, 163-169).

It is thus suggested that these properties of retigabine and other KCNQ modulators may prevent neuronal damage induced by excessive neuronal activation, and such compounds may be of use in the treatment of neurodegenerative diseases, and be disease modifying (or antiepileptogenic) in patients with epilepsy.

Given that anticonvulsant compounds such as benzodiazepines and chlormethiazole are used clincially in the treatment of the ethanol withdrawal syndrome and that other anticonvulsant compounds e.g. gabapentin, are very effective in animal models of this syndrome (Watson et al. *Neuropharmacology* 1997, 36, 1369-1375), we expect that other anticonvulsant compounds such as KCNQ openers are thus expected to be effective in this condition.

mRNA for KCNQ 2 and 3 subunits are found in brain regions associated with anxiety and emotional behaviours such as bipolar disorder e.g. hippocampus and amygdala (Saganich et al. *Journal of Neuroscience* 2001, 21, 4609-4624), and retigabine is reportedly active in some animal models of anxiety-like behaviour (Hartz et al. *Journal of Psychopharmacology* 2003, 17 suppl 3, A28,B16), and other clinically used anticonvulsant compounds are used in the treatment of bipolar disorder. Thus, KCNQ openers may be useful for the treatment of anxiety disorders and bipolar disorder.

WO 200196540 discloses the use of modulators of the M-current formed by expression of KCNQ2 and KCNQ3 genes for insomnia, while WO 2001092526 discloses that modulators of KCNQ5 can be utilized for the treatment of sleep disorders.

WO01/022953 describes the use of retigabine for prophylaxis and treatment of neuropathic pain such as allodynia, hyperalgesic pain, phantom pain, neuropathic pain related to diabetic neuropathy and neuropathic pain related to migraine.

WO02/049628 describes the use of retigabine for the treatment of anxiety disorders such as anxiety, generalized anxiety disorder, panic anxiety, obsessive compulsive disorder, social phobia, performance anxiety, post-traumatic stress disorder, acute stress reaction, adjustment disorders, hypochondriacal disorders, separation anxiety disorder, agoraphobia and specific phobias.

WO97/15300 describes the use of retigabine for the treatment of neurodegenerative disorders such as Alzheimer's disease; Huntington's chorea; sclerosis such as multiple sclerosis and amyotrophic lateral sclerosis; Creutzfeld-Jakob disease; Parkinson's disease; AIDS-induced encephalopathy and other infection-related encephalopathies being caused by rubella viruses, herpes viruses, borrelia and by unknown pathogens, trauma-induced neurodegenerations, neuronal hyperexcitation states such as in medicament withdrawal or intoxication, and neurodegenerative disorders of the peripheral nervous system such as polyneuropathies and polyneuritides.

Hence, there is a great desire for novel compounds, which are potent openers of the KCNQ family of potassium channels.

Also desired are novel compounds with improved properties relative to known compounds, which are openers of the KCNQ family potassium channels, such as retigabine. Improvement of one or more of the following parameters is desired: half-life, clearance, selectivity, interactions with other medications, bioavailability, potency, formulability, chemical stability, metabolic stability, membrane permeability, solubility and therapeutic index. The improvement of such parameters may lead to improvements such as:

an improved dosing regime by reducing the number of required doses a day,
ease of administration to patients on multiple medications,
reduced side effects,
enlarged therapeutic index,
improved tolerability or
improved compliance.

SUMMARY OF THE INVENTION

One object of the present invention is to provide novel compounds, which are potent openers of the KCNQ family potassium channels.

The compounds of the invention are substituted morpholine and thiomorpholine derivatives of the general formula I or salts thereof

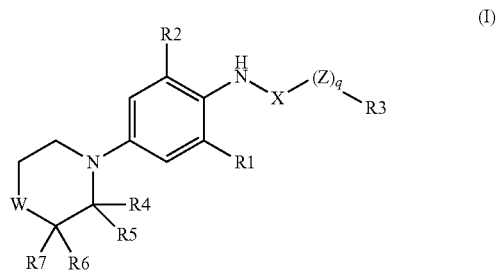

wherein q, W, X, Z, R1, R2, R3, R4, R5, R6 and R7 are as defined below.

The invention provides a compound of formula I for use as a medicament.

The invention further relates to a pharmaceutical composition comprising a compound of formula I, and the use thereof.

The invention thus provides a pharmaceutical composition comprising a compound of formula I and a pharmaceutically acceptable carrier or diluent.

The invention provides the use of a compound of formula I for the preparation of a medicament for the treatment of seizure disorders, anxiety disorders, neuropathic pain and migraine pain disorders or neurodegenerative disorders.

The invention furthermore concerns the use of a compound of formula I in a method of treatment of seizure disorders, anxiety disorders, neuropathic pain and migraine pain disorders or neurodegenerative disorders.

DETAILED DESCRIPTION OF THE INVENTION

The present invention relates to substituted morpholine and thiomorpholine derivatives which are potent openers of KCNQ potassium channels.

Accordingly, the present invention relates to substituted morpholine and thiomorpholine derivatives of the general formula I

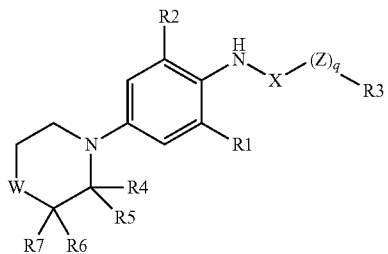

(I)

wherein
g is 0 or 1;
W is O or S;
X is CO;
Z is O;
R1 is selected from the group consisting of halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, $C_{1-6}$-alk(en/yn)yloxy, $C_{3-8}$-cycloalk(en)yloxy and $C_{3-8}$-cycloalk(en)yl-$C_{1-6}$-alk(en/yn)yloxy;
R2 is selected from the group consisting of halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, $C_{1-6}$-alk(en/yn)yloxy, $C_{3-8}$-cycloalk(en)yloxy, $C_{3-8}$-cycloalk(en)yl-$C_{1-6}$-alk(en/yn)yloxy, optionally substituted phenyl and optionally substituted pyridyl; wherein phenyl and pyridyl are optionally substituted with one or more substituents independently being halogen, $C_{1-6}$-alk(en/yn)yl, $C_{3-8}$-cycloalk(en)yl or $C_{3-8}$-cycloalk(en)yl-$C_{1-6}$-alk(en/yn)yl;
R3 is selected from the group consisting of $C_{1-10}$-alk(en/yn)yl, $C_{3-8}$-cycloalk(en)yl, $C_{3-8}$-cycloalk(en)yl-$C_{1-6}$-alk(en/yn)yl, Ar—$C_{1-6}$-alk(en/yn)yl, Ar—$C_{3-8}$-cycloalk(en)yl, Ar—$C_{3-8}$-cycloalk(en)yl-$C_{1-6}$-alk(en/yn)yl and Ar; and
each of R4, R5, R6 and R7 is independently selected from the group consisting of hydrogen and Ar;
as the free base or salts thereof.

In one embodiment of the compound of formula I, q is 0;
in another embodiment of the compound of formula I, q is 1.
In a further embodiment of the compound of formula I, W is an oxygen atom;
in another embodiment W is a sulphur atom.
In a further embodiment of the compound of formula I, R1 is selected from the group consisting of $C_{3-3}$-cycloalk(en)yl, $C_{3-8}$-cycloalk(en)yl-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, $C_{3-8}$-cycloalk(en)yloxy and $C_{3-8}$-cycloalk(en)yl-$C_{1-6}$-alk(en/yn)yloxy;
in another embodiment R1 is selected from the group consisting of halogen, halo-$C_{1-6}$-alk(en/yn)yl, $C_{1-6}$-alk(en/yn)yl and cyano.
Typically, R1 is selected from the group consisting of halogen, cyano, $C_{1-6}$-alk(en/yn)yl, halo-$C_{1-6}$-alk(en/yn)yl and $C_{1-6}$-alk(en/yn)yloxy.
To further illustrate without limiting the invention an embodiment of R1 is halogen;
another embodiment of R1 is cyano;
another embodiment of R1 is $C_{1-6}$-alk(en/yn)yl;
another embodiment of R1 is halo-$C_1$-alk(en/yn)yl;
another embodiment of R1 is $C_{1-6}$-alk(en/yn)yloxy.

In a further embodiment of the compound of formula I, R2 is selected from the group consisting of $C_{3-8}$-cycloalk(en)yl, $C_{3-8}$-cycloalk(en)yl-$C_{1-6}$-alk(en/yn)yl, halo-$C_{3-8}$-cycloalk(en)yl, halo-$C_{34}$-cycloalk(en)yl-$C_{1-6}$-alk(en/yn)yl, $C_{3-8}$-cycloalk(en)yloxy and $C_{3-8}$-cycloalk(en)yl-$C_{1-6}$-alk(en/yn)yloxy;
in another embodiment R2 is selected from the group consisting of halogen, halo-$C_{1-6}$-alk(en/yn)yl, $C_{1-6}$-alk(en/yn)yl and cyano.
Typically, R2 is selected from the group consisting of halogen, cyano, $C_{1-6}$-alk(en/yn)yl, halo-$C_{1-6}$-alk(en/yn)yl, $C_{1-6}$-alk(en/yn)yloxy, optionally substituted phenyl and optionally substituted pyridyl.
To further illustrate without limiting the invention an embodiment of R2 is halogen;
another embodiment of R2 is cyano;
another embodiment of R2 is $C_{1-6}$-alk(en/yn)yl;
another embodiment of R2 is halo-$C_{1-6}$-alk(en/yn)yl;
another embodiment of R2 is $C_{1-6}$-alk(en/yn)yloxy:
another embodiment of R2 is optionally substituted phenyl;
another embodiment of R2 is optionally substituted pyridyl.
In a further embodiment of the compound of R2, optionally substituted phenyl and optionally substituted pyridyl may be substituted with one or more substituents independently selected from the group consisting of halogen or $C_{1-6}$-alk(en/yn)yl;
in another embodiment of R2, phenyl and pyridyl are not substituted;
in yet another embodiment of R2, optionally substituted phenyl and optionally substituted pyridyl are substituted with one substituent;
in yet another embodiment of R2, optionally substituted phenyl and optionally substituted pyridyl are substituted with two substituents;
in yet another embodiment of R2, optionally substituted phenyl and optionally substituted pyridyl are substituted with three substituents.
In a further embodiment of the compound of formula I, R3 is selected from the group consisting of $C_{3-8}$-cycloalk(en)yl, Ar—$C_{3-8}$-cycloalk(en)yl and Ar—$C_{3-8}$-cycloalk(en)yl-$C_{1-6}$-alk(en/yn)yl.
Typically, R3 is selected from the group consisting of $C_{1-10}$-alk(en/yn)yl, $C_{3-8}$-cycloalk(en)yl-$C_{1-6}$-alk(en/yn)yl, Ar—$C_{1-6}$-alk(en/yn)yl and Ar
To further illustrate without limiting the invention an embodiment of R3 is $C_{1-10}$-alk(en/yn)yl;
another embodiment of R3 is $C_{3-8}$-cycloalk(en)yl-$C_{1-6}$-alk(en/yn)yl;
another embodiment of R3 is Ar—$C_{1-6}$-alk(en/yn)yl;
another embodiment of R3 is Ar.
In a further embodiment of the compound of formula I, Ar is selected from the group consisting of optionally substituted furan, optionally substituted thiazole, optionally substituted quinoline, optionally substituted indole, optionally substituted pyrimidine, optionally substituted pyrrole and optionally substituted oxazole;
in another embodiment Ar is selected from the group consisting of optionally substituted phenyl, optionally substituted thiophene and optionally substituted naphthyl;
in another embodiment Ar is selected from the group consisting of optionally substituted phenyl, optionally substituted thiophene, optionally substituted naphthyl and optionally substituted 2,3-dihydro-benzofuran;

in another embodiment Ar is selected from the group consisting of optionally substituted phenyl and optionally substituted pyridine.

In one embodiment of the invention, Ar represents optionally substituted phenyl, optionally substituted naphthyl, optionally substituted thiophene or optionally substituted 2,3-dihydro-benzofuran.

Typically, Ar is selected from the group consisting of optionally substituted phenyl, optionally substituted naphthyl, optionally substituted pyridine, optionally substituted 2,3-dihydro-benzofuran and optionally substituted thiophene.

To further illustrate without limiting the invention an embodiment of Ar is optionally substituted phenyl;
another embodiment of Ar is optionally substituted naphthyl;
another embodiment of Ar is optionally substituted pyridine;
another embodiment of Ar is optionally substituted 2,3-dihydro-benzofuran;
another embodiment of Ar is optionally substituted thiophene.

In a further embodiment of the compound of formula I, Ar refers to optionally substituted aromatic systems of 5-10 carbon atoms.

Typically, such optionally substituted aromatic systems of 5-10 carbon atoms are selected from optionally substituted phenyl and optionally substituted naphthyl.

In a further embodiment of the compound of formula I, Ar refers to a optionally substituted aromatic systems of 5-10 carbon atoms wherein 1, 2, 3 or 4 carbon atoms are replaced by heteroatoms independently selected from N, S, or O.

In a further embodiment of the compound of formula I, such optionally substituted aromatic system of 5-10 carbon atoms wherein 1, 2, 3 or 4 carbon atoms are replaced by heteroatoms is selected from the group consisting of optionally substituted pyridine, optionally substituted thiophene, optionally substituted furan, optionally substituted thiazole, optionally substituted quinoline, optionally substituted indole, optionally substituted 2,3-dihydro-benzofuran, optionally substituted pyrimidine, optionally substituted pyrrole and optionally substituted oxazole.

Typically, such optionally substituted aromatic system of 5-10 carbon atoms wherein 1, 2, 3 or 4 carbon atoms are replaced by heteroatoms is selected from the group consisting of optionally substituted pyridine, optionally substituted 2,3-dihydro-benzofuran and optionally substituted thiophene.

In a further embodiment of the compound of formula I, Ar is optionally substituted with one or more substituents independently being hydroxy, acyl, nitro or cyano, —CO—NH—$C_{1-6}$-alk(en/yn)yl, —CO—N($C_{1-6}$-alk(en/yn)yl)$_2$, —NH$_2$, —NH—$C_{1-6}$-alk(en/yn)yl, —N($C_{1-6}$-alk(en/yn)yl)$_2$, —S—$C_{1-6}$-alk(en/yn)yl, —SO$_2$—$C_{1-6}$-alk(en/yn)yl, —SO$_2$N($C_{1-6}$-alk(en/yn)yl)$_2$ and —SO$_2$NH—$C_{1-6}$-alk(en/yn)yl, or two adjacent substituents may together with the aromatic group to which they are attached form a 4-8 membered ring, which optionally contains one, two or three heteroatoms;

in another embodiment Ar is optionally substituted with one or more substituents independently being halogen, $C_{1-6}$-alk(en/yn)yl, $C_{3-8}$-cycloalk(en)yl, $C_{3-8}$-cycloalk(en)yl-$C_{1-6}$-alk(en/yn)yl, halo-$C_{1-6}$-alk(en/yn)yl, $C_{1-6}$-alk(en/yn)yloxy or $C_{3-8}$-alk(en/yn)yloxy;

in another embodiment Ar is optionally substituted with one or more substituents independently being halogen or halo-$C_{1-6}$-alk(en/yn)yl.

In one further embodiment of the invention, Ar is substituted with one or more substituents independently being halogen, $C_{1-6}$-alk(en/yn)yl, halo-$C_{1-6}$-alk(en/yn)yl, $C_{1-6}$-alk(en/yn)yloxy.

To further illustrate without limiting the invention an embodiment of Ar is substituted with halogen;
another embodiment of Ar is substituted with $C_{1-6}$-alk(en/yn)yl;
another embodiment of Ar is substituted with halo-$C_{1-6}$-alk(en/yn)yl;
another embodiment of Ar is substituted with $C_{1-6}$-alk(en/yn)yloxy;
another embodiment of Ar is un-substituted;
another embodiment of Ar is substituted with 1 substituent;
another embodiment of Ar is substituted with 2 substituents;
another embodiment of Ar is substituted with 3 substituents.

One embodiment relates to compounds of general formula I wherein at least one of R4 and R5 is not Ar.

Another embodiment relates to compounds of general formula I wherein at least one of R6 and R7 is not Ar.

Yet another embodiment relates to compounds of general formula I wherein at least three of R4, R5, R6 and R7 are not Ar.

Yet another embodiment relates to compounds of general formula I wherein at most one of R3, R4, R5, R6 and R7 comprises Ar;
yet another embodiment relates to compounds of general formula I wherein at most two of R3, R4, R5, R6 and R7 comprise Ar;
yet another embodiment relates to compounds of general formula I wherein at most three of R3, R4, R5, R6 and R7 comprise Ar;
yet another embodiment relates to compounds of general formula I wherein R3 does not comprise Ar;
yet another embodiment relates to compounds of general formula I wherein R4 does not comprise Ar;
yet another embodiment relates to compounds of general formula I wherein R5 does not comprise Ar;
yet another embodiment relates to compounds of general formula I wherein R6 does not comprise Ar;
yet another embodiment relates to compounds of general formula I wherein R7 does not comprise Ar.

One embodiment relates to compounds of general formula I wherein the stereo configuration on the carbon atom to which R4 and R5 are attached is the S-configuration.

Another embodiment relates to compounds of general formula I wherein the stereo configuration on the carbon atom to which R4 and R5 are attached is the R-configuration.

Yet another embodiment relates to compounds of general formula I wherein the stereo configuration on the carbon atom to which R6 and R7 are attached is the S-configuration.

Yet another embodiment relates to compounds of general formula I wherein the stereo configuration on the carbon atom to which R6 and R7 are attached is the R-configuration.

Yet another embodiment relates to compounds of general formula I wherein the stereo configuration on the carbon atom to which R4 and R5 are attached is identical to the stereo configuration on the carbon atom to which R6 and R7 are attached.

Yet another embodiment relates to compounds of general formula I wherein the stereo configuration on the carbon atom to which R4 and R5 are attached is different from the stereo configuration on the carbon atom to which R6 and R7 are attached.

The compounds of the following list and salts thereof exemplifies the invention, the list is in no way intended to be construed as limiting:

N-(2-Bromo-4-morpholin-4-yl-6-trifluoromethyl-phenyl)-2-(4-fluoro-phenyl)-acetamide;
2-Cyclopentyl-N-(2-bromo-6-trifluoromethyl-4-morpholin-4-yl-phenyl)-acetamide;
N-(2-Bromo-4-morpholin-4-yl-6-trifluoromethyl-phenyl)-3-cyclopentyl-propionamide;
N-(2-Chloro-6-cyano-4-morpholin-4-yl-phenyl)-3-cyclohexyl-propionamide;
2-Cyclopentyl-N-(2,6-dimethyl-4-thiomorpholin-4-yl-phenyl)-acetamide;
2-Cyclopentyl-N-[2,6-dimethyl-4-(2-phenyl-morpholin-4-yl)-phenyl]-acetamide;
2-Cyclopentyl-N-[2,6-dimethyl-4-(2-phenyl-thiomorpholin-4-yl)-phenyl]-acetamide;
2-Cyclopentyl-N-[2,6-dimethyl-4-(3-pyridin-3-yl-thiomorpholin-4-yl)-phenyl]-acetamide;
2-Cyclopentyl-N-{2,6-dimethyl-4-[2-(4-trifluoromethyl-phenyl)-thiomorpholin-4-yl]-phenyl}-acetamide;
N-{4-[2-(2-Chloro-phenyl)-thiomorpholin-4-yl]-2,6-dimethyl-phenyl}-2-cyclopentyl-acetamide;
2-Bicyclo[2.2.1]hept-2-yl-N-(2,6-dimethyl-4-morpholin-4-yl-phenyl)-acetamide;
2-Cyclohexyl-N-(2,6-dimethyl-4-morpholin-4-yl-phenyl)-acetamide;
3-(3,4-Difluoro-phenyl)-N-(2,6-dimethyl-4-morpholin-4-yl-phenyl)-propionamide;
2-Cyclopentyl-N-(2,6-dimethyl-4-morpholin-4-yl-phenyl)-acetamide;
(2,6-Dimethyl-4-morpholin-4-yl-phenyl)-carbamic acid butyl ester;
2-(4-Chloro-phenyl)-N-(2,6-dimethyl-4-morpholin-4-yl-phenyl)-acetamide;
2,3-Dihydro-benzofuran-2-carboxylic acid (2,6-dimethyl-4-morpholin-4-yl-phenyl)-amide;
3-Cyclohexyl-N-(2,6-dimethyl-4-morpholin-4-yl-phenyl)-propionamide;
3-Cyclopentyl-N-(2,6-dimethyl-4-morpholin-4-yl-phenyl)-propionamide;
N-(2,6-Dimethyl-4-morpholin-4-yl-phenyl)-2-(4-fluoro-phenyl)-acetamide;
N-(2,6-Dimethyl-4-morpholin-4-yl-phenyl)-2-thiophen-2-yl-acetamide;
N-(2,6-Dimethyl-4-morpholin-4-yl-phenyl)-3,3-dimethyl-butyramide;
Hexanoic acid (2,6-dimethyl-4-morpholin-4-yl-phenyl)-amide;
2-Cycloheptyl-N-(2,6-dimethyl-4-morpholin-4-yl-phenyl)-acetamide;
(2,6-Dimethyl-4-morpholin-4-yl-phenyl)-carbamic acid benzyl ester;
(2,6-Dimethyl-4-morpholin-4-yl-phenyl)-carbamic acid 2-chloro-benzyl ester;
3,5,5-Trimethyl-hexanoic acid (2,6-dimethyl-4-morpholin-4-yl-phenyl)-amide;
Octanoic acid (2,6-dimethyl-4-morpholin-4-yl-phenyl)-amide;
Heptanoic acid (2,6-dimethyl-4-morpholin-4-yl-phenyl)-amide;
N-(2,6-Dimethyl-4-morpholin-4-yl-phenyl)-2-phenyl-acetamide;
2-(3,4-Dichloro-phenyl)-N-(2,6-dimethyl-4-morpholin-4-yl-phenyl)-acetamide;
2-(4-Allyloxy-3-chloro-phenyl)-N-(2,6-dimethyl-4-morpholin-4-yl-phenyl)-acetamide;
N-(2,6-Dimethyl-4-morpholin-4-yl-phenyl)-2-(3-trifluoromethyl-phenyl)-acetamide;
N-(2,6-Dimethyl-4-morpholin-4-yl-phenyl)-2-naphthalen-2-yl-acetamide;
3-(3-Chloro-phenyl)-N-(2,6-dimethyl-4-morpholin-4-yl-phenyl)-propionamide;
N-(2,6-Dimethyl-4-morpholin-4-yl-phenyl)-2-(3,4-dimethyl-phenyl)-acetamide;
2-(3-Bromo-phenyl)-N-(2,6-dimethyl-4-morpholin-4-yl-phenyl)-acetamide;
2-(3-Chloro-phenyl)-N-(2,6-dimethyl-4-morpholin-4-yl-phenyl)-acetamide;
N-(2,6-Dimethyl-4-morpholin-4-yl-phenyl)-2-p-tolyl-acetamide;
N-(2,6-Dimethyl-4-morpholin-4-yl-phenyl)-2-m-tolyl-acetamide;
2-(3,4-Difluoro-phenyl)-N-(2,6-dimethyl-4-morpholin-4-yl-phenyl)-acetamide;
N-(2,6-Dimethyl-4-morpholin-4-yl-phenyl)-2-(3-fluoro-phenyl)-acetamide;
N-(2-Bromo-4-morpholin-4-yl-6-trifluoromethyl-phenyl)-3-cyclohexyl-propionamide;
N-(2-Bromo-4-morpholin-4-yl-6-trifluoromethyl-phenyl)-2-(3-fluoro-phenyl)-acetamide;
N-(2-Bromo-4-morpholin-4-yl-6-trifluoromethyl-phenyl)-propionamide;
N-(2-Bromo-4-morpholin-4-yl-6-trifluoromethyl-phenyl)-butyramide;
N-(2-Chloro-4-morpholin-4-yl-6-trifluoromethyl-phenyl)-2-(3-fluoro-phenyl)-acetamide;
N-(2-Chloro-4-morpholin-4-yl-6-trifluoromethyl-phenyl)-2-cyclopentyl-acetamide;
2-Cyclopentyl-N-{2,6-dimethyl-4-[2-(4-trifluoromethyl-phenyl)-morpholin-4-yl]-phenyl}-acetamide;
N-{4-[2-(2-Chloro-phenyl)-morpholin-4-yl]-2,6-dimethyl-phenyl}-2-cyclopentyl-acetamide;
2-Cyclopentyl-N-{4-[2-(4-fluoro-phenyl)-morpholin-4-yl]-2,6-dimethyl-phenyl}-acetamide;
2-(2-Chloro-phenyl)-N-(2,6-dimethyl-4-morpholin-4-yl-phenyl)-acetamide;
Pentanoic acid (2,6-dimethyl-4-morpholin-4-yl-phenyl)-amide;
4-Methyl-pentanoic acid (2,6-dimethyl-4-morpholin-4-yl-phenyl)-amide;
2-Cyclopent-2-enyl-N-(2,6-dimethyl-4-morpholin-4-yl-phenyl)-acetamide;
5-Methyl-hexanoic acid (2,6-dimethyl-4-morpholin-4-yl-phenyl)-amide;
3-Methyl-pentanoic acid (2,6-dimethyl-4-morpholin-4-yl-phenyl)-amide;
Hex-5-enoic acid (2,6-dimethyl-4-morpholin-4-yl-phenyl)-amide;
3-Ethyl-pentanoic acid (2,6-dimethyl-4-morpholin-4-yl-phenyl)-amide;
2-Cyclopentyl-N-(4-morpholin-4-yl-2-pyridin-3-yl-6-trifluoromethyl-phenyl)-acetamide;
2-Cyclopentyl-N-(5-morpholin-4-yl-3-trifluoromethyl-biphenyl-2-yl)-acetamide;
2-Cyclopentyl-N-(4'-fluoro-5-morpholin-4-yl-3-trifluoromethyl-biphenyl-2-yl)-acetamide;
2-Cyclopentyl-N-(4'-methyl-5-morpholin-4-yl-3-trifluoromethyl-biphenyl-2-yl)-acetamide;
2-Cyclopentyl-N-(3'-methyl-5-morpholin-4-yl-3-trifluoromethyl-biphenyl-2-yl)-acetamide;
2-Cyclopentyl-N-(3',4'-difluoro-5-morpholin-4-yl-3-trifluoromethyl-biphenyl-2-yl)-acetamide;
2-(4-Fluoro-phenyl)-N-(4-morpholin-4-yl-2-pyridin-3-yl-6-trifluoromethyl-phenyl)-acetamide;

2-Cyclopentyl-N-(2,6-diethyl-4-morpholin-4-yl-phenyl)-acetamide;
2-Cyclopentyl-N-(2,6-diisopropyl-4-morpholin-4-yl-phenyl)-acetamide;
2-Cyclopentyl-N-(2,6-difluoro-4-morpholin-4-yl-phenyl)-acetamide;
Hexanoic acid (2,6-difluoro-4-morpholin-4-yl-phenyl)-amide;
N-(2,6-Difluoro-4-morpholin-4-yl-phenyl)-3,3-dimethyl-butyramide;
N-(2,6-Difluoro-4-morpholin-4-yl-phenyl)-2-(3-fluoro-phenyl)-acetamide;
2-Cyclopent-2-enyl-N-(2,6-difluoro-4-morpholin-4-yl-phenyl)-acetamide;
2-Bicyclo[2.2.1]hept-2-yl-N-(2,6-difluoro-4-morpholin-4-yl-phenyl)-acetamide;
2-Bicyclo[2.2.1]hept-2-yl-N-(2-methyl-4-morpholin-4-yl-6-trifluoromethyl-phenyl)-acetamide;
5-Methyl-pentanoic acid (2-methyl-4-morpholin-4-yl-6-trifluoromethyl-phenyl)-amide;
5-Methyl-hexanoic acid (2-methyl-4-morpholin-4-yl-6-trifluoromethyl-phenyl)-amide;
2-Cyclopent-2-enyl-N-(2-methyl-4-morpholin-4-yl-6-trifluoromethyl-phenyl)-acetamide;
2-Cyclopentyl-N-(2-methyl-4-morpholin-4-yl-6-trifluoromethyl-phenyl)-acetamide;
Hexanoic acid (2-methyl-4-morpholin-4-yl-6-trifluoromethyl-phenyl)-amide;
3,3-Dimethyl-N-(2-methyl-4-morpholin-4-yl-6-trifluoromethyl-phenyl)-butyramide;
2-(3,4-Difluoro-phenyl)-N-(2-methyl-4-morpholin-4-yl-6-trifluoromethyl-phenyl)-acetamide;
Hexanoic acid (2-methoxy-6-methyl-4-morpholin-4-yl-phenyl)-amide;
2-Cyclopentyl-N-(2-methoxy-6-methyl-4-morpholin-4-yl-phenyl)-acetamide;
N-(2-Methoxy-6-methyl-4-morpholin-4-yl-phenyl)-3,3-dimethyl-butyramide;
2-(3,4-Difluoro-phenyl)-N-(2-methoxy-6-methyl-4-morpholin-4-yl-phenyl)-acetamide;
2-Cyclopent-2-enyl-N-(2-methoxy-6-methyl-4-morpholin-4-yl-phenyl)-acetamide;
2-(3-Fluoro-phenyl)-N-(2-methoxy-6-methyl-4-morpholin-4-yl-phenyl)-acetamide;
2-Bicyclo[2.2.1]hept-2-yl-N-(2-methoxy-6-methyl-4-morpholin-4-yl-phenyl)-acetamide;
4-Methyl-pentanoic acid (2-methoxy-6-methyl-4-morpholin-4-yl-phenyl)-amide;
5-Methyl-hexanoic acid (2-methoxy-6-methyl-4-morpholin-4-yl-phenyl)-amide;
N-(2-Chloro-6-methyl-4-morpholin-4-yl-phenyl)-2-(3-fluoro-phenyl)-acetamide; and
N-(2-Chloro-6-methyl-4-morpholin-4-yl-phenyl)-2-cyclopentyl-acetamide;
as the free base or a salt thereof. Each of these compounds is considered a specific embodiment and may be subjected to individual claims.

The present invention also comprises salts of the compounds of the invention, typically, pharmaceutically acceptable salts. The salts of the invention include acid addition salts, metal salts, ammonium and alkylated ammonium salts.

The salts of the invention are preferably acid addition salts. The acid addition salts of the invention are preferably pharmaceutically acceptable salts of the compounds of the invention formed with non-toxic acids. Acid addition salts include salts of inorganic acids as well as organic acids. Examples of suitable inorganic acids include hydrochloric, hydrobromic, hydroiodic, phosphoric, sulfuric, sulfamic, nitric acids and the like. Examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutical acceptable inorganic or organic acid addition salts include the pharmaceutically acceptable salts listed in J. Pharm. Sci. 1977, 66, 2, which is incorporated herein by reference.

Also intended as acid addition salts are the hydrates, which the present compounds, are able to form.

Examples of metal salts include lithium, sodium, potassium, magnesium salts and the like.

Examples of ammonium and alkylated ammonium salts include ammonium, methyl-, dimethyl-, trimethyl-, ethyl-, hydroxyethyl-, diethyl-, n-butyl-, sec-butyl-, tert-butyl-, tetramethylammonium salts and the like.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

The compounds of the present invention may have one or more asymmetric centre and it is intended that any optical isomers (i.e. enantiomers or diastereomers), as separated, pure or partially purified optical isomers and any mixtures thereof including racemic mixtures, i.e. a mixture of stereoisomers, are included within the scope of the invention.

Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can also be resolved into their optical antipodes, e.g. by fractional crystallization. The compounds of the present invention may also be resolved by the formation of diastereomeric derivatives. Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981). Optically active compounds can also be prepared from optically active starting materials, or by stereoselective synthesis.

Furthermore, when a double bond or a fully or partially saturated ring system is present in the molecule geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention.

The invention also encompasses prodrugs of the present compounds, which on administration undergo chemical conversion by metabolic processes before becoming pharmacologically active substances. In general, such prodrugs will be functional derivatives of the compounds of the general formula I, which are readily convertible in vivo into the required compound of the formula I. Conventional procedures for the selection and preparation of suitable prodrug derivatives are described, for example, in "Design of Prodrugs", ed. H. Bundgaard, Elsevier, 1985.

The invention also encompasses active metabolites of the present compounds. An aspect of the invention provides a compound of formula I or a salt thereof for use as a medicament.

In one embodiment, the invention relates to the use of one or more compounds according to the invention in a method of treatment. The disorder or disease to be treated is responsive to an increased ion flow in a potassium channel such as the KCNQ family potassium ion channels. Such disorder or disease is preferably a disorder or disease of the central nervous system.

In yet another embodiment, the invention provides a pharmaceutical composition comprising one or more pharmaceutically acceptable carriers or diluents and one or more compounds of formula I or a salt thereof.

A further embodiment of the invention relates to the use of a compound of formula I or a salt thereof for the preparation of a pharmaceutical composition for the treatment of a disease or disorder wherein a KCNQ potassium channel opener such as a KCNQ2 potassium channel opener is beneficial. Typically, such disorder or disease is selected from the group consisting of seizure disorders, anxiety disorders, neuropathic pain and migraine pain disorders or neurodegenerative disorders.

In one embodiment, the compounds of the invention may be administered as the only therapeutically effective compound.

In another embodiment the compounds of the invention may be administered as a part of a combination therapy, i.e. the compounds of the invention may be administered in combination with other therapeutically effective compounds having e.g. anti-convulsive properties. The effects of such other compounds having anti-convulsive properties may include but not be limited to activities on:

ion channels such as sodium, potassium, or calcium channels
  the excitatory amino acid systems e.g. blockade or modulation of NMDA receptors
  the inhibitory neurotransmitter systems e.g. enhancement of GABA release, or blockade of GABA-uptake or
  membrane stabilisation effects.

Current anti-convulsive medications include, but are not limited to, tiagabine, carbamazepine, sodium valproate, lamotrigine, gabapentin, pregabalin, ethosuximide, levetiracetam, phenyloin, topiramate, zonisamide as well as members of the benzodiazepine and barbiturate class.

The compounds of the invention are considered useful for increasing ion flow in a voltage-dependent potassium channel in a mammal such as a human. The compounds are thus considered useful in the treatment of a disorder or disease being responsive to an increased ion flow in a voltage-dependent potassium channel, such as the KCNQ family potassium ion channels. Such disorder or disease is preferably a disorder or disease of the central nervous system.

In one embodiment, the disorder or disease is selected from the group consisting of seizure disorders; such as acute seizures, convulsions, status epilepticus and epilepsy such as epileptic syndromes and epileptic seizures; in particular convulsions, epilepsy and status epilepticus.

In another embodiment the disorder or disease is selected from the group consisting of neuropathic pain and migraine pain disorders; such as allodynia, hyperalgesic pain, phantom pain, neuropathic pain related to diabetic neuropathy, neuropathic pain related to trigeminal neuralgia and neuropathic pain related to migraine; in particular allodynia, hyperalgesic pain, phantom pain, neuropathic pain related to diabetic neuropathy and neuropathic pain related to migraine.

In yet another embodiment, the disorder or disease is selected from the group consisting of anxiety disorders; such as anxiety and disorders and diseases related to panic attack, agoraphobia, panic disorder with agoraphobia, panic disorder without agoraphobia, agoraphobia without history of panic disorder, specific phobia, social phobia and other specific phobias, obsessive-compulsive disorder, posttraumatic stress disorder, acute stress disorders, generalized anxiety disorder, anxiety disorder due to general medical condition, substance-induced anxiety disorder, separation anxiety disorder, adjustment disorders, performance anxiety, hypochondriacal disorders, anxiety disorder due to general medical condition and substance-induced anxiety disorder and anxiety disorder not otherwise specified; in particular anxiety, generalized anxiety disorder, panic anxiety, obsessive compulsive disorder, social phobia, performance anxiety, post-traumatic stress disorder, acute stress reaction, adjustment disorders, hypochondriacal disorders, separation anxiety disorder, agoraphobia, specific phobias, anxiety disorder due to general medical condition and substance-induced anxiety disorder.

In yet another embodiment, the disorder or disease is selected from the group consisting of neurodegenerative disorders; such as Alzheimer's disease, Huntington's chorea, multiple sclerosis, amyotrophic lateral sclerosis, Creutzfeld-Jakob disease, Parkinson's disease, encephalopathies induced by AIDS or infection by rubella viruses, herpes viruses, borrelia and unknown pathogens, trauma-induced neurodegenerations, neuronal hyperexcitation states such as in medicament withdrawal or intoxication and neurodegenerative diseases of the peripheral nervous system such as polyneuropathies and polyneuritides; in particular Alzheimer's disease, Huntington's chorea, multiple sclerosis, amyotrophic lateral sclerosis, AIDS-induced encephalopathy and other infection-related encephalopathies being caused by rubella viruses, herpes viruses, borrelia and by unknown pathogens, Creutzfeld-Jakob disease, Parkinson's disease, trauma-induced neurodegenerations. In yet another embodiment, the disorder or disease is selected from the group consisting of neuronal hyperexcitation states such as in medicament withdrawal or by intoxication.

In yet another embodiment, the disorder or disease is selected from the group consisting of bipolar disorders.

In yet another embodiment, the disorder or disease is selected from the group consisting of sleep disorders; such as insomnia.

The term "treatment" as used herein in connection with a disease or disorders includes also prevention, inhibition and amelioration as the case may be.

In one embodiment, the compounds of the invention have been found to have effect on potassium channels of the KCNQ family, in particular the KCNQ2 subunit.

The invention provides compounds showing effect in one or more of the following tests:

"Relative efflux through the KCNQ2 channel"
  Which is a measure of the potency of the compound at the target channel
"Maximum electroshock"
  Which is a measure of seizures induced by non-specific CNS stimulation by electrical means
"Pilocarpine induced seizures"
  Seizures induced by pilocarpine are often difficult to treat with many existing antiseizure medications and so reflect a model of "drug resistant seizures"
"Electrical seizure-threshold tests" and "Chemical seizure-threshold tests"
  These models measure the threshold at which seizures are initiated, thus being models that detect whether compounds could delay seizure initiation.
"Amygdala kindling"
  Which is used as a measure of disease progression, as in normal animals the seizures in this model get more severe as the animal receives further stimulations
"Electrophysiological patch-clamp recordings in CHO cells" and "electrophysiological recordings of KCNQ2, KCNQ2/KCNQ3 or KCNQ5 channels in oocytes"
  In these tests voltage-activated KCNQ2, KCNQ2/KCNQ3 or KCNQ5 currents are recorded.

In one embodiment, the compounds are KCNQ2 active with an $EC_{50}$ of less than 15000 nM such as less than 10000 nM as measured by the test "Relative efflux through the KCNQ2 channel". In another embodiment, the compounds are KCNQ2 active with an $EC_{50}$ of less than 2000 nM such as less than 1500 nM as measured by the test "Relative efflux through the KCNQ2 channel". In yet another embodiment, the compounds are KCNQ2 active with an $EC_{50}$ of less than 200 nM such as less than 150 nM as measured by the test "Relative efflux through the KCNQ2 channel". The test "Relative efflux through the KCNQ2 channel" is described below.

In one embodiment, the compounds have an $ED_{50}$ of less than 15 mg/kg in the test "Maximum electroshock". In another embodiment, the compounds have an $ED_{50}$ of less than 5 mg/kg in the test "Maximum electroshock". The test "Maximum electroshock" is described below.

In one embodiment, the compounds have an $ED_{50}$ of less than 5 mg/kg in the "Electrical seizure-threshold test" and "Chemical seizure-threshold test" which are described below.

Some compounds have few or clinically insignificant side effects. Some of the compounds are thus tested in models of the unwanted sedative, hypothermic and ataxic actions of the compounds.

Some of the compounds have a large therapeutic index between anticonvulsant efficacy and side-effects such as impairment of locomotor activity or ataxic effects as measured by performance on a rotating rod. Such compounds will expectedly be well tolerated in patients permitting high doses to be used before side effects are seen. Thereby compliance with the therapy will expectedly be good and administration of high doses may be permitted making the treatment more efficacious in patients who would otherwise have side effects with other medications.

A non-limiting aspect of the invention concerns compounds according to below embodiments 1-10:

1. A substituted morpholine or thiomorpholine derivative of the general formula I

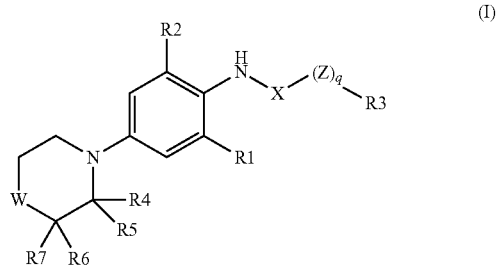

wherein
q is 0 or 1;
W is O or S;
X is CO;
Z is O;
R1 and R2 are independently selected from the group consisting of halogen, halo-$C_{1-6}$-alk(en/yn)yl, $C_{1-6}$-alk(en/yn)yl and cyano;
R3 is selected from the group consisting of $C_{1-10}$-alk(en/yn)yl, $C_{3-8}$-cycloalk(en)yl-$C_{1-6}$-alk(en/yn)yl, Ar—$C_{1-6}$-alk(en/yn)yl and Ar; and
R4, R5, R6 and R7 are independently selected from the group consisting of hydrogen and Ar;
as the free base or salts thereof.

2. A compound according to embodiment 1, said compound being selected from the group consisting of:
N-(2-Bromo-4-morpholin-4-yl-6-trifluoromethyl-phenyl)-2-(4-fluoro-phenyl)-acetamide;
2-Cyclopentyl-N-(2-bromo-6-trifluoromethyl-4-morpholin-4-yl-phenyl)-acetamide;
N-(2-Bromo-4-morpholin-4-yl-6-trifluoromethyl-phenyl)-3-cyclopentyl-propionamide;
N-(2-Chloro-6-cyano-4-morpholin-4-yl-phenyl)-3-cyclohexyl-propionamide;
2-Cyclopentyl-N-(2,6-dimethyl-4-thiomorpholin-4-yl-phenyl)-acetamide;
2-Cyclopentyl-N-[2,6-dimethyl-4-(2-phenyl-morpholin-4-yl)-phenyl]-acetamide;
2-Cyclopentyl-N-{2,6-dimethyl-4-(2-phenyl-thiomorpholin-4-yl)-phenyl}-acetamide;
2-Cyclopentyl-N-[2,6-dimethyl-4-(3-pyridin-3-yl-thiomorpholin-4-yl)-phenyl]-acetamide;
2-Cyclopentyl-N-{2,6-dimethyl-4-[2-(4-trifluoromethyl-phenyl)-thiomorpholin-4-yl]-phenyl}-acetamide;
N-{4-[2-(2-Chloro-phenyl)-thiomorpholin-4-yl]-2,6-dimethyl-phenyl}-2-cyclopentyl-acetamide;
2-Bicyclo[2.2.1]hept-2-yl-N-(2,6-dimethyl-4-morpholin-4-yl-phenyl)-acetamide;
2-Cyclohexyl-N-(2,6-dimethyl-4-morpholin-4-yl-phenyl)-acetamide;
3-(3,4-Difluoro-phenyl)-N-(2,6-dimethyl-4-morpholin-4-yl-phenyl)-propionamide;
2-Cyclopentyl-N-(2,6-dimethyl-4-morpholin-4-yl-phenyl)-acetamide;
(2,6-Dimethyl-4-morpholin-4-yl-phenyl)-carbamic acid butyl ester;

2-(4-Chloro-phenyl)-N-(2,6-dimethyl-4-morpholin-4-yl-phenyl)-acetamide;
2,3-Dihydro-benzofuran-2-carboxylic acid (2,6-dimethyl-4-morpholin-4-yl-phenyl)-amide;
3-Cyclohexyl-N-(2,6-dimethyl-4-morpholin-4-yl-phenyl)-propionamide;
3-Cyclopentyl-N-(2,6-dimethyl-4-morpholin-4-yl-phenyl)-propionamide;
N-(2,6-Dimethyl-4-morpholin-4-yl-phenyl)-2-(4-fluoro-phenyl)-acetamide;
N-(2,6-Dimethyl-4-morpholin-4-yl-phenyl)-2-thiophen-2-yl-acetamide;
N-(2,6-Dimethyl-4-morpholin-4-yl-phenyl)-3,3-dimethyl-butyramide;
Hexanoic acid (2,6-dimethyl-4-morpholin-4-yl-phenyl)-amide;
2-Cycloheptyl-N-(2,6-dimethyl-4-morpholin-4-yl-phenyl)-acetamide;
(2,6-Dimethyl-4-morpholin-4-yl-phenyl)-carbamic acid benzyl ester;
(2,6-Dimethyl-4-morpholin-4-yl-phenyl)-carbamic acid 2-chloro-benzyl ester;
3,5,5-Trimethyl-hexanoic acid (2,6-dimethyl-4-morpholin-4-yl-phenyl)-amide;
Octanoic acid (2,6-dimethyl-4-morpholin-4-yl-phenyl)-amide;
Heptanoic acid (2,6-dimethyl-4-morpholin-4-yl-phenyl)-amide;
N-(2,6-Dimethyl-4-morpholin-4-yl-phenyl)-2-phenyl-acetamide
2-(3,4-Dichloro-phenyl)-N-(2,6-dimethyl-4-morpholin-4-yl-phenyl)-acetamide;
2-(4-Allyloxy-3-chloro-phenyl)-N-(2,6-dimethyl-4-morpholin-4-yl-phenyl)-acetamide;
N-(2,6-Dimethyl-4-morpholin-4-yl-phenyl)-2-(3-trifluoromethyl-phenyl)-acetamide;
N-(2,6-Dimethyl-4-morpholin-4-yl-phenyl)-2-naphthalen-2-yl-acetamide;
3-(3-Chloro-phenyl)-N-(2,6-dimethyl-4-morpholin-4-yl-phenyl)-propionamide;
N-(2,6-Dimethyl-4-morpholin-4-yl-phenyl)-2-(3,4-dimethyl-phenyl)-acetamide;
2-(3-Bromo-phenyl)-N-(2,6-dimethyl-4-morpholin-4-yl-phenyl)-acetamide;
2-(3-Chloro-phenyl)-N-(2,6-dimethyl-4-morpholin-4-yl-phenyl)-acetamide;
N-(2,6-Dimethyl-4-morpholin-4-yl-phenyl)-2-p-tolyl-acetamide;
N-(2,6-Dimethyl-4-morpholin-4-yl-phenyl)-2-m-tolyl-acetamide;
2-(3,4-Difluoro-phenyl)-N-(2,6-dimethyl-4-morpholin-4-yl-phenyl)-acetamide; and
N-(2,6-Dimethyl-4-morpholin-4-yl-phenyl)-2-(3-fluoro-phenyl)-acetamide.

3. A pharmaceutical composition comprising one or more pharmaceutically acceptable carriers or diluents and one or more compounds according to any one of embodiments 1 and 2.

4. Use of a pharmaceutical composition according to embodiment 3 for increasing ion flow in a voltage-dependent potassium channel of a mammal such as a human.

5. Use according to embodiment 4 in the treatment of a disorder or disease being responsive to an increased ion flow in a voltage-dependent potassium channel, such disorder or disease is preferably a disorder or diseases of the central nervous system.

6. Use according to embodiment 5 characterized in that the disorder or disease is selected from the group consisting of seizure disorders such as convulsions, epilepsy and status epilepticus.

7. Use according to embodiment 5 characterized in that the disorder or disease is selected from the group consisting of neuropathic and migraine pain disorders such as allodynia, hyperalgesic pain, phantom pain, neuropathic pain related to diabetic neuropathy and neuropathic pain related to migraine.

8. Use according to embodiment 5 characterized in that the disorder or disease is selected from the group consisting of anxiety disorders such as anxiety, generalized anxiety disorder, panic anxiety, obsessive compulsive disorder, social phobia, performance anxiety, post-traumatic stress disorder, acute stress reaction, adjustment disorders, hypochondriacal disorders, separation anxiety disorder, agoraphobia, specific phobias, anxiety disorder due to general medical condition and substance-induced anxiety disorder.

9. Use according to embodiment 5 characterized in that the disorder or disease is selected from the group consisting of neurodegenerative disorders such as Alzheimer's disease, Huntington's chorea, multiple sclerosis, amyotrophic lateral sclerosis, AIDS-induced encephalopathy and other infection-related encephalopathies being caused by rubella viruses, herpes viruses, borrelia and by unknown pathogens, Creutzfeld-Jakob disease, Parkinson's disease, trauma-induced neurodegenerations.

10. Use according to embodiment 5 characterized in that the disorder or disease is selected from the group consisting of neuronal hyperexcitation states such as in medicament withdrawal or by intoxication.

Definitions

The term heteroatom refers to a nitrogen, oxygen or sulphur atom.

Halogen means fluoro, chloro, bromo or iodo.

The expression $C_{1-6}$-alk(en/yn)yl means a $C_{1-6}$-alkyl, $C_{2-6}$-alkenyl or a $C_{2-6}$-alkynyl group. The term $C_{1-6}$-alkyl refers to a branched or un-branched alkyl group having from one to six carbon atoms inclusive, including but not limited to methyl, ethyl, 1-propyl, 2-propyl, 1-butyl, 2-butyl, 2-methyl-2-propyl and 2-methyl-1-propyl. Similarly, $C_{2-6}$-alkenyl and $C_{2-6}$-alkynyl, respectively, designate such groups having from two to six carbon atoms, including one double bond and one triple bond respectively, including but not limited to ethenyl, propenyl, butenyl, ethynyl, propynyl and butynyl.

The expression $C_{1-10}$-alk(en/yn)yl means a $C_{1-10}$-alkyl, $C_{2-10}$-alkenyl or a $C_{2-10}$-alkynyl group. The term $C_{1-10}$-alkyl refers to a branched or un-branched alkyl group having from one to six carbon atoms inclusive, including but not limited to methyl, ethyl, 1-propyl, 2-propyl, 1-butyl, 2-butyl, 1-pentyl, 1-hexyl, 1-heptyl, 1-octyl, 1-nonyl, 1-decyl, 2-methyl-2-propyl and 2-methyl-1-propyl. Similarly, $C_{2-10}$-alkenyl and $C_{2-10}$-alkynyl, respectively, designate such groups having from two to six carbon atoms, including one double bond and one triple bond respectively, including but not limited to ethenyl, propenyl, butenyl, pentenyl, hexenyl, heptenyl, octenyl, nonenyl, decenyl, ethynyl, propynyl, butynyl, pentynyl, hexynyl, heptynyl, octynyl, nonynyl, and decynyl.

The expression $C_{3-8}$-cycloalk(en)yl means a $C_{3-8}$-cycloalkyl- or cycloalkenyl group. The term $C_{3-8}$-cycloalkyl designates a monocyclic or bicyclic carbocycle having three to eight C-atoms, including but not limited to cyclopropyl, cyclopentyl, cyclohexyl, cycloheptyl, cyclooctyl, [1.1.1]bicyclopentyl, bicyclo[2.2.1]heptyl, [2.2.2]bicyclooctyl and [3.3.0]bicyclooctyl, etc. The term $C_{3-8}$-cycloalkenyl designates a monocyclic or bicyclic carbocycle having three to eight C-atoms and including one double bond.

The term halo-$C_{1-6}$-alk(en/yn)yl designates $C_{1-6}$-alk(en/yn)yl being substituted with one or more halogen atoms, including but not limited to trifluoromethyl.

Similarly, halo-$C_{3-8}$-cycloalk(en)yl designates $C_{3-4}$-cycloalk(en)yl being substituted with one or more halogen atoms.

In the expression halo-$C_{3-8}$-cycloalk(en)yl-$C_{1-6}$-alk(en/yn)yl the terms $C_{1-6}$-alk(en/yn)yl and halo-$C_{3-8}$-cycloalk(en)yl are as defined above.

When two adjacent substituents together with the aromatic group to which they are attached form a 4-8 membered ring, which optionally contains one, two or three heteroatoms, then a ring system is formed by 4-8 atoms selected from 4-8 carbon atoms and 0-3 heteroatoms selected from N, S, or O, Such two adjacent substituents may together form:
—$(CH_2)_a$—$CH_2$—, —CH=CH—$(CH_2)_b$—, —$CH_2$—CH=CH—$(CH_2)_c$—, —CH=CH—CH=CH—, —$(CH_2)_a$—O—, —O—$(CH_2)_b$—, —$CH_2$—O—$(CH_2)_c$—O—, —$CH_2$—O—$CH_2$—O—$CH_2$—, —$(CH_2)_a$—S—, —S—$(CH_2)_b$—S—, —$CH_2$—S—$(CH_2)_c$—S—, —$CH_2$—S—$CH_2$—S—$CH_2$—, —$(CH_2)_a$—NH—, —NH—$(CH_2)_b$—NH—, —$CH_2$—NH—$(CH_2)_c$—NH—, —CH=CH—NH—, —O—$(CH_2)_b$—NH—, —$CH_2$—O—$(CH_2)_c$—NH— or —O—$(CH_2)_c$—NH—$CH_2$—, —S—$(CH_2)_b$—NH—, —N=CH—NH—, —N=CH—O— or —N=CH—S— or —N=N—NH—,
wherein b is 1, 2 or 3, a is 2, 3 or 4 and c is 1 or 2.

The term Ar refers to optionally substituted aromatic systems of 5-10 carbon atoms, wherein 0, 1, 2, 3 or 4 carbon atoms may be replaced by heteroatoms independently selected from N, S, or O. Examples of such Ar groups are optionally substituted phenyl, optionally substituted naphthyl, optionally substituted pyridine, optionally substituted thiophene, optionally substituted furan, optionally substituted thiazole, optionally substituted quinoline, optionally substituted indole, optionally substituted 2,3-dihydro-benzofuran, optionally substituted pyrimidine, optionally substituted pyrrole and optionally, substituted oxazole. Ar may be substituted with one or more substituents independently being hydroxy, halogen, $C_{1-6}$-alk(en/yn)yl, $C_{3-8}$-cycloalk(en)yl, $C_{3-8}$-cycloalk(en)yl-$C_{1-6}$-alk(en/yn)yl, halo-$C_{1-6}$-alk(en/yn)yl, $C_{1-6}$-alk(en/yn)yloxy, $C_{3-8}$-alk(en/yn)yloxy, acyl, nitro or cyano, —CO—NH—$C_{1-6}$-alk(en/yn)yl, —CO—N($C_{1-6}$-alk(en/yn)yl)$_2$, —$NH_2$, —NH—$C_{1-6}$-alk(en/yn)yl, —N($C_{1-6}$-alk(en/yn)yl)$_2$, —S—$C_{1-6}$-alk(en/yn)yl, —$SO_2$—$C_{1-6}$-alk(en/yn)yl, —$SO_2$N($C_{1-6}$-alk(en/yn)yl)$_2$ and —$SO_2$NH—$C_{1-6}$-alk(en/yn)yl; or two adjacent substituents may together with the aromatic group to which they are attached form a 4-8 membered ring, which optionally contains one, two or three heteroatoms.

When Ar is substituted with CO—NH—$C_{1-6}$-alk(en/yn)yl or CO—N($C_{1-6}$-alk(en/yn)yl)$_2$, then the carbon atom of the CO group is attached to Ar.

When Ar is substituted with $NH_2$, NH—$C_{1-6}$-alk(en/yn)yl or N($C_{1-6}$-alk(en/yn)yl)$_2$, then the nitrogen atom is attached to Ar.

When Ar is substituted with —S—$C_{1-6}$-alk(en/yn)yl, —$SO_2$—$C_{1-6}$-alk(en/yn)yl, —$SO_2$N($C_{1-6}$-alk(en/yn)yl)$_2$ or —$SO_2$NH—$C_{1-6}$-alk(en/yn)yl then the sulphur atom is attached to Ar.

The term acyl refers to formyl, $C_{1-6}$-alk(en/yn)ylcarbonyl, $C_{3-8}$-cycloalk(en)ylcarbonyl, Ar-carbonyl, Ar—$C_{1-6}$-alk(en/yn)ylcarbonyl or a $C_{3-8}$-cycloalk(en)yl-$C_{1-6}$-alk(en/yn)ylcarbonyl group, wherein $C_{1-6}$-alk(en/yn)yl, $C_{3-8}$-cycloalk(en)yl and Ar are as defined above.

The terms $C_{3-8}$-cycloalk(en)yl-$C_{1-6}$-alk(en/yn)yl, Ar—$C_{1-6}$-alk(en/yn)yl, $C_{1-6}$-alk(en/yn)yloxy and $C_{3-8}$-cycloalk(en)yloxy; designate such groups in which the $C_{1-6}$-alk(en/yn)yl, $C_{3-8}$-cycloalk(en)yl and Ar are as defined above.

Similarly, $C_{3-8}$-cycloalk(en)yl-$C_{1-6}$-alk(en/yn)yloxy designate such groups in which $C_{3-8}$-cycloalk(en)yl and $C_{1-6}$-alk(en/yn)yloxy are as defined above.

The expressions Ar—$C_{3-8}$-cycloalk(en)yl and Ar—$C_{3-8}$-cycloalk(en)yl-$C_{1-6}$-alk(en/yn)yl designate such groups in which the $C_{1-6}$-alk(en/yn)yl, $C_{3-8}$-cycloalk(en)yl and Ar are as defined above.

Pharmaceutical Compositions

The present invention also relates to a pharmaceutical composition. The compounds of the invention or salts thereof may be administered alone or in combination with pharmaceutically acceptable carriers or diluents, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19 Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the disorder or disease to be treated and the active ingredient chosen.

The pharmaceutical compositions formed by combining the compound of the invention and the pharmaceutical acceptable carriers are then readily administered in a variety of dosage forms suitable for the disclosed routes of administration. The formulations may conveniently be presented in unit dosage form by methods known in the art of pharmacy.

The compounds of this invention are generally utilized as the free substance or as a pharmaceutically acceptable salt thereof. One example is an acid addition salt of a compound having the utility of a free base. When a compound of the invention contains a free base such salts are prepared in a conventional manner by treating a solution or suspension of a free base of the invention with a chemical equivalent of a pharmaceutically acceptable acid. Representative examples are mentioned above.

Pharmaceutical compositions for oral administration may be solid or liquid. Solid dosage forms for oral administration include e.g. capsules, tablets, dragees, pills, lozenges, powders, granules and tablette e.g. placed in a hard gelatine capsule in powder or pellet form or e.g. in the form of a troche or lozenge. Where appropriate, pharmaceutical compositions for oral administration may be prepared with coatings such as enteric coatings or they can be formulated so as to provide controlled release of the active ingredient such as sustained or prolonged release according to methods well known in the art. Liquid dosage forms for oral administration include e.g. solutions, emulsions, suspensions, syrups and elixirs.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid, lower alkyl ethers of cellulose, corn starch, potato starch, gums and the like. Examples of liquid carriers are syrup, peanut oil, olive oil, phospho lipids, fatty acids, fatty acid amines, polyoxyethylene and water.

The carrier or diluent may include any sustained release material known in the art, such as glyceryl monostearate or glyceryl distearate, alone or mixed with a wax.

Any adjuvants or additives usually used for such purposes such as colourings, flavourings, preservatives etc. may be used provided that they are compatible with the active ingredients.

The amount of solid carrier may vary but will usually be from about 25 mg to about 1 g.

If a liquid carrier is used, the preparation may be in the form of a syrup, emulsion, soft gelatine capsule or sterile injectable liquid such as an aqueous or non-aqueous liquid suspension or solution.

Tablets may be prepared by mixing the active ingredient with ordinary adjuvants or diluents and subsequently compressing the mixture in a conventional tabletting machine.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Depot injectable formulations are also contemplated as being within the scope of the present invention.

For parenteral administration, solutions of the compound of the invention in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Solutions for injections may be prepared by dissolving the active ingredient and possible additives in a part of the solvent for injection, preferably sterile water, adjusting the solution to the desired volume, sterilising the solution and filling it in suitable ampoules or vials. Any suitable additive conventionally used in the art may be added, such as tonicity agents, preservatives, antioxidants, etc.

Other suitable administration forms include suppositories, sprays, ointments, cremes, gels, inhalants, dermal patches, implants, etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the disorder or disease treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.01 to about 1000 mg, such as about 0.01 to 100 mg, preferably from about 0.05 to about 500 mg, and more preferred from about 0.5 mg to about 200 mg.

For parenteral routes such as intravenous, intrathecal, intramuscular and similar administration, typically doses are in the order of about half the dose employed for oral administration.

Typical examples of recipes for the formulation of the invention are as follows:

1) Tablets containing 5.0 mg of a compound of the invention calculated as the free base:

| | |
|---|---|
| Compound of formulae I | 5.0 mg |
| Lactose | 60 mg |
| Maize starch | 30 mg |
| Hydroxypropylcellulose | 2.4 mg |
| Microcrystalline cellulose | 19.2 mg |
| Croscarmellose Sodium Type A | 2.4 mg |
| Magnesium stearate | 0.84 mg |

2) Tablets containing 0.5 mg of a compound of the invention calculated as the free base:

| | |
|---|---|
| Compound of formulae I | 0.5 mg |
| Lactose | 46.9 mg |
| Maize starch | 23.5 mg |
| Povidone | 1.8 mg |
| Microcrystalline cellulose | 14.4 mg |
| Croscarmellose Sodium Type A | 1.8 mg |
| Magnesium stearate | 0.63 mg |

3) Syrup containing per milliliter:

| | |
|---|---|
| Compound of formulae I | 25 mg |
| Sorbitol | 500 mg |
| Hydroxypropylcellulose | 15 mg |
| Glycerol | 50 mg |
| Methyl-paraben | 1 mg |
| Propyl-paraben | 0.1 mg |
| Ethanol | 0.005 mL |
| Flavour | 0.05 mg |
| Saccharin sodium | 0.5 mg |
| Water | ad 1 mL |

4) Solution for injection containing per milliliter:

| | |
|---|---|
| Compound of formulae I | 0.5 mg |
| Sorbitol | 5.1 mg |
| Acetic Acid | 0.05 mg |
| Saccharin sodium | 0.5 mg |
| Water | ad 1 mL |

By the expression a compound of the invention is meant any one of the embodiments of formula I as described herein.

In a further aspect the present invention relates to a method of preparing a compound of the invention as described in the following.

Preparation of the Compounds of the Invention

The compounds of the invention of the general formula I, wherein q, W, X, Z, R1, R2, R3, R4, R5, R6 and R7 are as defined above may be prepared by the methods as represented in the schemes and as described below:

Scheme 1.
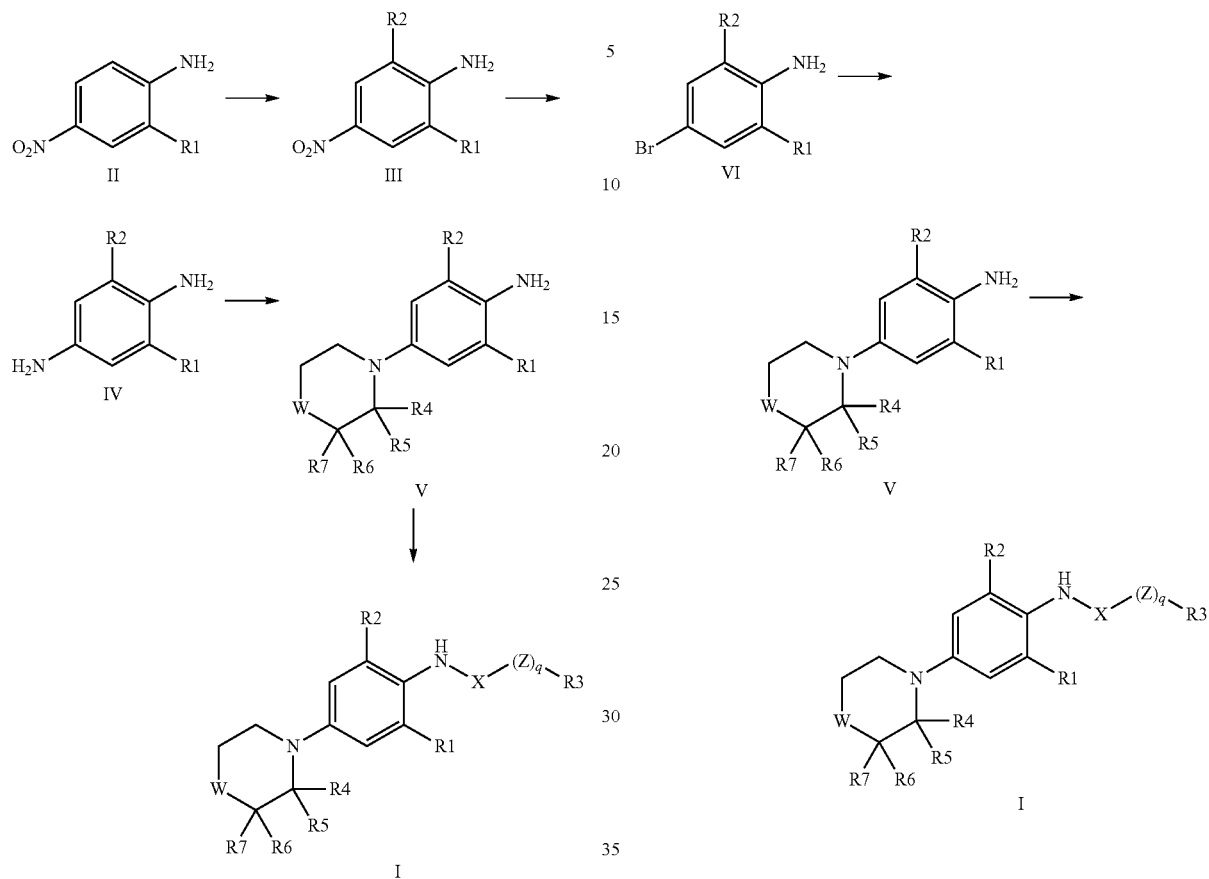
Scheme 3.
Scheme 2.
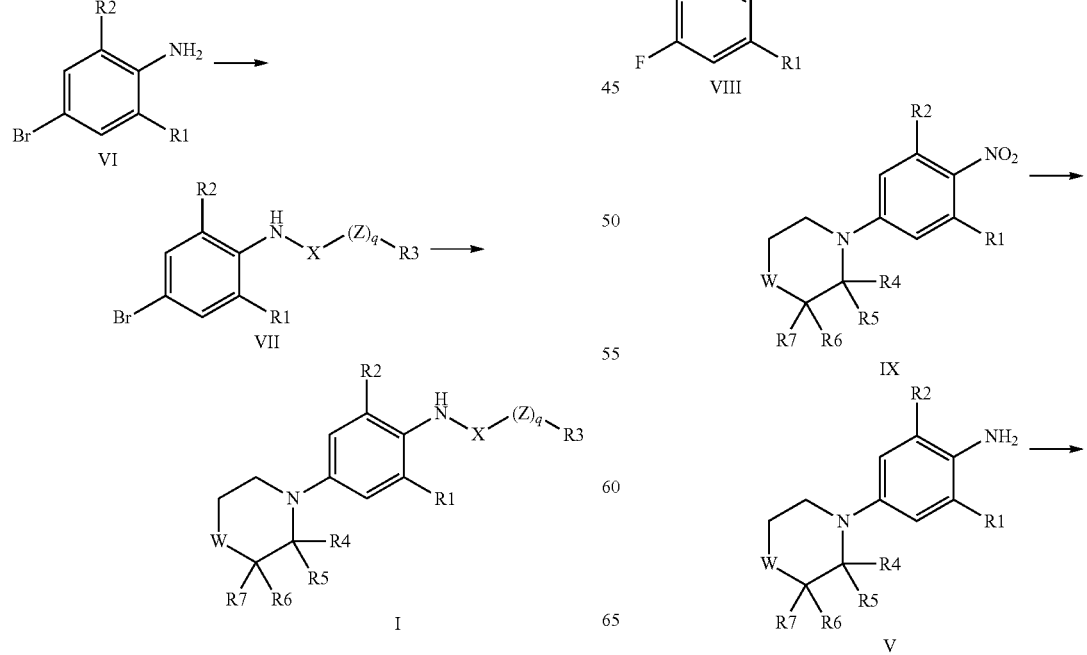
Scheme 4.

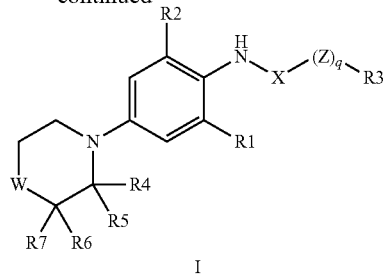

I

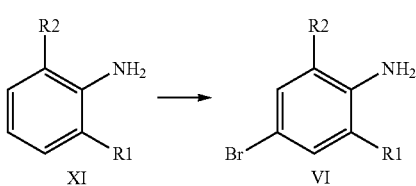

Scheme 5.

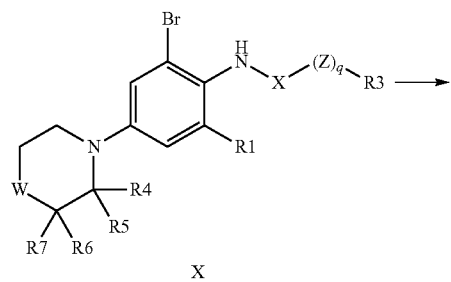

X

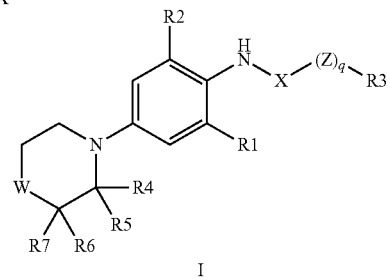

I (I: R2 = Br)

In the compounds of the general formulae I-XV, q, W, X, Z, R1, R2, R3, R4, R5, R6 and R7 are as defined under formula I.

Compounds of the general formulae II, III, VI, VIII and XI are either obtained from commercial sources, or prepared by standard methods known to chemists skilled in the art.

Alternatively, compounds of the general formula III, where R2 is halogen such as Cl, Br or I (scheme 1), are obtained by means of regioselective electrophilic aromatic substitution, well known to chemists skilled in the art, with appropriate electrophiles such as N-chlorosuccinimide, N-bromosuccinimide, bromine, iodine or iodochloride in a suitable solvent such as acetic acid, as described in "Electrophilic halogenations" by P. B. D. de la Mare, Cambridge University Press, Cambridge, 1976.

The nitro group in compounds of the general formulae III, IX and XIII (schemes 1, 4 and 6) can be reduced with suitable reducing agents such as zinc or iron powder in the presence of acid such as acetic acid or aqueous hydrochloric acid, or by hydrogen gas or ammonium formiate in the presence of a suitable hydrogenation catalyst such as palladium on activated carbon in suitable solvents such as methanol, ethanol, or tetrahydrofuran, at suitable temperatures or under ultrasonic irradiation, to obtain anilines of the general formulae IV, V and XIV, respectively. Alternatively, tin (II) chloride or sodium dithionite can be used as reducing agents under conditions well known to the chemist skilled in the art.

Compounds of the general formulae I and VII (schemes 1, 2, 3 and 4) may be prepared by reacting compounds of the

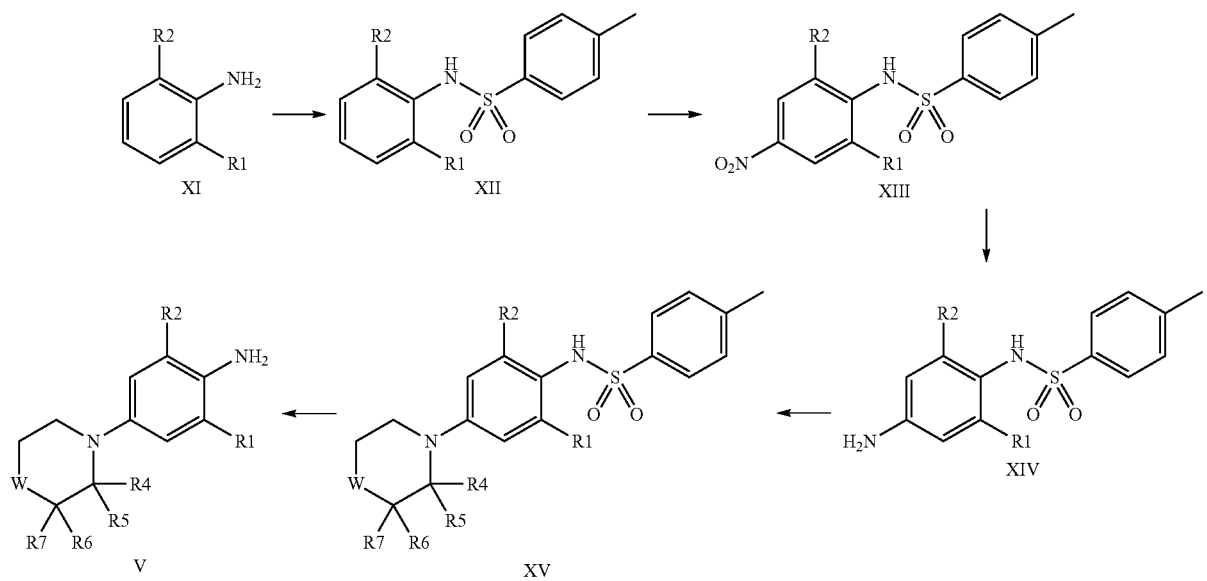

general formulae V and VI, respectively, with suitable electrophilic reagents, such as, but not limited to, suitably substituted carboxylic acid chlorides, carboxylic acid bromides, carboxylic acid iodides, carboxylic acid anhydrides, activated esters, chloro formates, and with or without the addition of bases, such as pyridine, trialkyl amines, potassium carbonate, magnesium oxide or lithium-, sodium-, or potassium alcoholates, in a suitable solvent, such as ethyl acetate, dioxane, tetrahydrofuran, acetonitrile or diethyl ether, at a suitable temperature, such as room temperature or reflux temperature.

Alternatively, compounds of the general formulae I and V (schemes 2 and 3) may be prepared by palladium catalysed C—N bond-forming reaction between suitably substituted compounds of the general formulae VII and VI and suitably substituted morpholines or thiomorpholines, as described by S. L. Buchwald et al. (M. C. Harris, X. Hang and S. L. Buchwald, Organic Letters, 2002, 4, 2885).

Compounds of the general formulae V and XV (schemes 1 and 6) may be prepared by reacting compounds of the general formulae IV and XIV with suitably substituted bis-(2-haloethyl)ethers and with or without the addition of bases, such as trialkyl amines, potassium carbonate or lithium-, sodium-, or potassium alcoholates, in a suitable solvent, such as dimethyl sulfoxide or N,N-dimethylformamide, at a suitable temperature, such as room temperature or reflux temperature.

Alternatively, compounds of the general formula V (scheme 3) may be prepared by reacting compounds of the general formula VI with suitably substituted morpholine or thiomorpholine derivatives in the presence of a palladium catalyst, such as bis(dibenzylideneacetone)palladium with the addition of a suitable phosphine ligand, such as (±)-2,2'-bis(diphenylphosphino)-1,1'-binaphthyl in the presence of base, such as potassium carbonate or lithium-, sodium-, or potassium alcoholates, in a suitable solvent, such as toluene or tetrahydrofuran, at a suitable temperature, such as room temperature or reflux temperature.

Compounds of the general formula IX (scheme 4) may be prepared by reacting compounds of the general formula VIII with suitably substituted morpholines or thiomorpholines and with or without the addition of bases, such as potassium carbonate, in a suitable solvent, such as dimethyl sulfoxide or N,N-dimethylformamide, at a suitable temperature, such as room temperature or reflux temperature.

Compounds of the general formula I, wherein R2 is Ar or Het (scheme 5), may be prepared from compounds of the general formula X, by means of cross-coupling reactions known to chemists skilled in the art, such as Suzuki coupling, Stille coupling, or other transition metal catalyzed cross-coupling reactions (D. W. Knight, "Coupling reactions between sp2 carbon centers" in *Comprehensive Organic Synthesis*, v. 3, pp. 481-520, Pergamon Press, 1991).

Compounds of the general formula VI (scheme 7), may be prepared from compounds of the general formula XI, by means of electrophilic aromatic substitution well known to chemists skilled in the art, with appropriate electrophiles such as N-bromosuccinimide or bromine in a suitable solvent such as acetic acid, as described by P. B. D. de la Mare and J. H. Ridd, "Preparative methods of aromatic halogenation" in *Aromatic substitutions*, pp. 105-115, Butterworths Scientific Publications, London, 1959.

Compounds of the general formula XII (scheme 6) may be prepared by reacting compounds of the general formula XI with p-toluenesulfonyl chloride with or without the addition of bases, such as pyridine, trialkyl amines, potassium carbonate, sodium hydrogen carbonate, magnesium oxide or lithium-, sodium-, or potassium alcoholates, in a suitable solvent, such as pyridine, ethyl acetate, dioxane, tetrahydrofuran, acetonitrile or diethyl ether, at suitable temperatures, such as room temperature or reflux temperature.

Compounds of the general formula XIII (scheme 6) may be prepared from compounds of the general formula XII, by nitration reactions known to chemists skilled in the art, such as reaction with concentrated nitric acid, sodium nitrite or sodium nitrate, in a suitable solvent, such as glacial acetic acid, acetic anhydride, trifluoroacetic acid, concentrated sulfuric acid or mixtures thereof, at appropriate temperatures, for example as described by P. B. D. de la Mare and J. H. Ridd, "Preparative methods of nitration" in *Aromatic substitutions*, pp. 48-56, Butterworths Scientific Publications, London, 1959.

Compounds of the general formula V (scheme 6) may be prepared by treating compounds of the general formula XV under strong acidic conditions such as aqueous sulfuric acid or aqueous hydrochloric acid, at suitable temperatures, such as room temperature or reflux temperature.

EXAMPLES

Analytical LC-MS data were obtained on a PE Sciex API 150EX instrument equipped with atmospheric pressure photo ionisation and a Shimadzu LC-8A/SLC-10A LC system. Column: 30×4.6 mm Waters Symmetry C18 column with 3.5 μm particle size; Solventsystem: A=water/trifluoroacetic acid (100:0.05) and B=water/acetonitrile/trifluoroacetic acid (5:95:0.03); Method: Linear gradient elution with 90% A to 100% B in 4 minutes and with a flow rate of 2 mL/minute. Purity was determined by integration of the UV (254 nm) and ELSD trace. The retention times ($t_R$) are expressed in minutes.

Preparative LC-MS-purification was performed on the same instrument with atmospheric pressure chemical ionisation. Column: 50×20 mm YMC ODS-A with 5 μm particle size; Method: Linear gradient elution with 80% A to 100% B in 7 minutes and with a flow rate of 22.7 mL/minute. Fraction collection was performed by split-flow MS detection.

Analytical LC-MS-TOF (TOF=time of flight) data were obtained on a micromass LCT 4-ways MUX equipped with a Waters 2488/Sedex 754 detector system. Column: 30×4.6 mm Waters Symmetry C18 column with 3.5 μm particle size; Solventsystem: A=water/trifluoroacetic acid (100:0.05) and B=water/acetonitrile/trifluoroacetic acid (5:95:0.03); Method: Linear gradient elution with 90% A to 100% B in 4 minutes and with a flow rate of 2 mL/minute. Purity was determined by integration of the UV (254 nm) and ELSD trace. The retention times ($t_R$) are expressed in minutes.

GC-MS data were obtained on a Varian CP 3800 gaschromatograph fitted with a Phenomenex column (Zebron ZB-5, length: 15 metres, internal diameter: 0.25 mm) coupled to a Varian Saturn 2000 iontrap mass spectrometer. Method: Duration 15 minutes, column flow 1.4 mL/minute (carrier gas was helium), oven gradient: 0-1 minute, 60° C.; 1-13 minutes, 60-300° C.; 13-15 minutes, 300° C.

$^1$H NMR spectra were recorded at 500.13 MHz on a Bruker Avance DRX500 instrument. Deuterated chloroform (99.8% D) or dimethyl sulfoxide (99.8% D) were used as solvents. TMS was used as internal reference standard. Chemical shift values are expressed in ppm-values. The following abbreviations are used for multiplicity of NMR signals: s=singlet, d=doublet, t=triplet, q=quartet, qui=quintet, h=heptet, dd=double doublet, ddd=double double doublet, dt=double triplet, dq=double quartet, tt=triplet of triplets, m=multiplet and b=broad singlet.

Microwave experiments were performed in sealed process vials or reactors using an Emrys Synthesizer or Emrys Optimizer EXP from Personal Chemistry or a Milestone Microsynth instrument from Milestone. When a reaction was heated in a microwave instrument, it was cooled to 25° C. before the next process step.

Preparation of Intermediates

2,6-Dimethyl-4-morpholin-4-yl-phenylamine

Bis(dibenzylideneacetone)palladium (2.88 g) and (±)-2,2'-bis(diphenylphosphino)-1,1'-binaphthyl (4.69 g) were added to dry toluene (175 mL purged with argon) and stirred for 15 minutes under argon. Potassium tert-butoxide (7.06 g), morpholine (8.7 mL) and 4-bromo-2,6-dimethylaniline (10.03 g) were added subsequently. The reaction mixture was heated to reflux for 16 hours under argon, cooled and filtered through silica (200 g). Brine (250 mL) was added and the mixture was extracted with ethyl acetate (3×200 mL). The combined organic phases were dried over magnesium sulfate and concentrated in vacuo. The crude product was dissolved in diethyl ether (250 mL), filtered through silica (200 g) and concentrated in vacuo to furnish 8.5 g (41% yield) of the title compound as a dark oil. The product was used without further purification. GC-MS (m/z) 206 (M$^+$); $t_R$=6.90. $^1$H NMR (500 MHz, CDCl$_3$): 2.18 (s, 6H), 3.02 (m, 4H), 3.85 (m, 4H), 6.62 (b, 2H).

N-(4-Bromo-2,6-dimethyl-phenyl)-2-cyclopentyl-acetamide

4-Bromo-2,6-dimethylaniline (5.92 g) and cyclopentylacetyl chloride (4.87 mL) were dissolved in acetonitrile (26 mL) and heated to 150° C. for 10 minutes in a sealed microwave process vial. The reaction was cooled to 0° C., the product filtered off and washed with cold acetonitrile (50 mL) affording 8.43 g (92% yield) of the title compound as a brown solid. The crude product was used without further purification. LC-MS (m/z) 312 (MH$^+$); $t_R$=3.10, (UV, ELSD) 89%, 99%. $^1$H NMR (500 MHz, CDCl$_3$): 1.22 (m, 2H), 1.52 (m, 2H), 1.63 (m, 2H), 1.77 (m, 2H), 2.06 (s, 6H), 2.31 (m, 1H), 2.64 (d, 2H), 7.15 (s, 2H), 9.98 (b, 1H).

2-Bromo-4-nitro-6-trifluoromethyl-phenylamine

Bromine (0.60 mL) dissolved in acetic acid (11 mL) was added dropwise to a solution of 4-nitro-2-trifluoromethyl-phenylamine (2.4 g) in acetic acid (12 mL). The reaction mixture was heated to 120° C. for TA hours, poured into water (400 mL) and filtered. The collected solid was washed with water (200 mL) and dried in vacuo to furnish 3.03 g (91% yield) of the title compound as a yellow solid. $^1$H NMR (500 MHz, DMSO-d$_o$): 7.08 (s, 2H), 8.23 (d, 1H), 8.51 (d, 1H).

2-Bromo-6-trifluoromethyl-benzene-1,4-diamine

Aqueous hydrochloric acid (2 M, 45 mL) was added slowly to a mixture of zinc dust (8.6 g) and 2-bromo-4-nitro-6-trifluoromethyl-phenylamine (2.5 g) in tetrahydrofuran (50 mL). The reaction mixture was stirred for 1 hour, filtered and neutralized with saturated aqueous sodium bicarbonate (100 mL). Water (100 mL) was added and the mixture was extracted with ethyl acetate (2×100 mL). The combined organic phases were washed with water (2×200 mL) and brine (200 mL), dried over sodium sulfate and concentrated in vacuo to furnish 2.22 g (98% yield) of the title compound as a red solid. $^1$H NMR (500 MHz, DMSO-d$_6$): 4.55 (s, 2H), 4.91 (s, 2H), 6.76 (d, 1H), 7.01 (d, 1H).

2-Bromo-4-morpholin-4-yl-6-trifluoromethyl-phenylamine

2-Bromo-6-trifluoromethyl-benzene-1,4-diamine (2.21 g), bis-(2-bromoethyl)ether (1.30 mL) and N,N-diisopropyl-ethylamine (4.64 mL) were mixed in N,N-dimethylformamide (19 mL) and heated to 180° C. for 30 minutes in a sealed microwave process vial. Saturated aqueous bicarbonate (100 mL) was added and the crude mixture was extracted with ethyl acetate (100 mL). The organic phase was washed with water (100 mL) and brine (100 mL), dried over sodium sulfate and concentrated in vacuo. The crude product was purified by flash chromatography to furnish 1.78 g (63%) of the title compound as a yellow solid. LC-MS (m/z) 326 (MH$^+$); $t_R$=2.54, (UV, ELSD) 83%, 75%. $^1$H NMR (500 MHz, DMSO-d$_6$): 2.99 (m, 4H), 3.70 (m, 4H), 5.00 (s, 2H), 7.00 (d, 1H), 7.38 (d, 1H).

2,5-Diamino-3-chloro-benzonitrile

Aqueous hydrochloric acid (12 M, 5.3 mL) was added slowly to a mixture of zinc dust (2.01 g) and 2-amino-3-chloro-5-nitro-benzonitrile (0.50 g) in tetrahydrofuran (40 mL). The reaction mixture was stirred for 2 hours, neutralized with saturated aqueous sodium carbonate (50 mL), and extracted with ethyl acetate (3×50 mL). The combined organic phases were dried over sodium sulfate and concentrated in vacuo to furnish 0.42 g (99% yield) of the title compound as a red solid. $^1$H NMR (500 MHz, DMSO-d$_6$): 4.89 (s, 2H), 5.13 (s, 2H), 6.64 (d, 1H), 6.89 (d, 1H).

2-Amino-3-chloro-5-morpholin-4-yl-benzonitrile 2,5-Diamino-3-chloro-benzonitrile (387 mg), bis-(2-bromoethyl)ether (0.35 mL) and N,N-diisopropyl-ethylamine (1.25 mL) were mixed in N,N-dimethylformamide (4 mL) and heated to 180° C. for 30 minutes in a sealed microwave process vial. Saturated aqueous bicarbonate (20 mL) was added and the crude mixture was extracted with ethyl acetate (20 mL). The organic phase was washed with water (20 mL) and brine (20 mL), dried over sodium sulfate and concentrated in vacuo to furnish 0.50 g (91%) of the title compound as a brown solid. LC-MS (m/z) 238 (MH$^+$); $t_R$=2.31, (UV, ELSD) 85%, 95%. $^1$H NMR (500 MHz, DMSO-d$_6$): 2.97 (m, 4H), 3.69 (m, 4H), 5.59 (s; 2H), 7.04 (d, 1H), 7.29 (d, 1H).

[2-(4-Fluoro-phenyl)-2-hydroxy-ethyl]-carbamic acid tert-butyl ester

To a stirred solution of carbamic acid tert-butyl ester (0.22 g) in acetonitrile (6 mL) was added in sequence at 0° C.: Sodium hydroxide (52 mg) in water (5 mL); after 2 minutes tert-butyl hypochlorite (139 μL); after 10 minutes potassium osmate(VI) dihydrate (9 mg) in water (1 mL); after 1 minute hydroquinine (anthraquinone-1,4-diyl)diether (26 mg) in acetonitrile (4 mL); after 3 minutes acetonitrile (6.7 mL) and phosphate buffer (3.3 mL, 0.5 M pH 7.65); after 5 minutes enough sodium biphosphate monohydrate to make pH=7.65; and finally 4-fluorostyrene. The reaction was quenched after stirring 3 hours at 25° C. with sodium sulfite (0.20 g) in water (2 mL) at 0° C. The phases were separated and the aqueous layer extracted with ethyl acetate (3×20 mL). The combined organic phases were washed with water (1×50 mL), dried over sodium sulfate, concentrated in vacuo and purified by flash chromatography to furnish 90 mg (57%) of the title compound as a colorless oil. $^1$H NMR (500 MHz, CDCl$_3$):

1.45 (s, 9H), 3.18 (m, 1H), 3.23 (m, 1H), 3.44 (m, 1H), 4.83 (m, 1H), 4.92 (b, 1H), 7.04 (t, 2H), 7.34 (m, 2H).

The following compounds were prepared analogously:

[2-Hydroxy-2-(4-trifluoromethyl-phenyl)-ethyl]-carbamic acid tert-butyl ester

Yield: 82%. $^1$H NMR (500 MHz, CDCl$_3$): 1.44 (s, 9H), 3.26 (m, 1H), 3.52 (m, 2H), 4.40 (b, 1H), 4.92 (b, 1H), 7.49 (d, 2H), 7.61 (d, 2H).

[2-(2-Chloro phenyl)-2-hydroxy-ethyl]-carbamic acid tert-butyl ester

Yield: 61%. $^1$H NMR (500 MHz, CDCl$_3$): 1.44 (s, 9H), 3.32 (m, 1H), 3.51 (m, 1H), 4.23 (m, 1H), 5.08 (b, 1H), 5.19 (b, 1H), 7.20 (m, 1H), 7.28 (m, 1H), 7.59 (m, 1H).

2-(4-Fluoro phenyl)-morpholine

A solution of [2-(4-fluoro-phenyl)-2-hydroxy-ethyl]-carbamic acid tert-butyl ester (90 mg) in dichloromethane (1 mL) and trifluoroacetic acid (1 mL) was stirred at 25° C. for 1 hour and then concentrated in vacuo. The residue was partitioned between ethyl acetate (5 mL) and saturated aqueous potassium carbonate (5 mL). The organic phase was dried over sodium sulfate, concentrated in vacuo and redissolved in dry tetrahydrofuran (3 mL) and triethylamine (54 µL). Chloroacetyl chloride (31 µL) in dry tetrahydrofuran (1 mL) was added dropwise at 0° C. After 30 minutes the reaction was diluted with ethyl acetate (10 mL) and washed with water/brine (1:1, 3×10 mL). The organic phase was dried over sodium sulfate, concentrated in vacuo and redissolved in tert-butanol (5 mL). Potassium tert-butoxide (79 mg) was added and the reaction stirred at 25° C. for 1.5 hour. The reaction was quenched with saturated aqueous ammonium chloride (30 mL) and extracted with ethyl acetate (2×30 mL). The combined organic phases were dried over sodium sulfate, concentrated in vacuo and co-evaporated with toluene (2×5 mL). The residue was dissolved in dry toluene (5 mL) under argon and treated with sodium bis(2-methoxyethoxy)aluminium hydride (70% in toluene, 205 µL) dropwise and stirred at 25° C. for 5 hours. The reaction was quenched at 0° C. with 10% aqueous sodium hydroxide (5 mL), and the mixture was extracted with diethyl ether (2×15 mL). The combined organic phases were dried over sodium sulfate and concentrated in vacuo to furnish 60 mg (94%) of the title compound as a colorless oil. LC-MS (m/z) 182 (MH$^+$); $t_R$=1.06, (UV, ELSD) 78%, 98%.

The following compounds were prepared analogously:

2-(4-Trifluoro-phenyl)-morpholine

Yield: 85%. LC-MS (m/z) 232 (MH$^+$); $t_R$=1.59, (UV, ELSD) 79%, 99%.

2-(2-Chloro phenyl)-morpholine

Yield: 86%. LC-MS (m/z) 198 (MH$^+$); $t_R$=1.21, (UV, ELSD) 66%, 99%.

4-Bromo-2-methoxy-6-methyl-phenylamine

To 2-methoxy-6-methyl-phenylamine (10.0 g) dissolved in acetonitrile (200 mL) was added N-bromosuccinimide (14.3 g) and the reaction mixture was heated to 145° C. for 15 minutes in a sealed microwave process vessel. The crude mixture was filtered through Celite, diluted with diethyl ether (200 mL) and washed with sodium hydroxide (2 M, 2×100 mL) and brine (1×100 mL). The organic phase was dried over magnesium sulfate, concentrated in vacuo and purified by flash chromatography to furnish 3.4 g (26%) of the title compound as a black solid. $^1$NMR (500 MHz, DMSO-d$_6$): 2.06 (s, 3H), 3.77 (s, 3H), 4.55 (s, 2H), 6.78 (d, 1H), 6.82 (d, 1H).

The following compound was prepared analogously:

4-Bromo-2-methyl-6-trifluoromethyl-phenylamine

Yield: 80%. GC-MS (m/z) 254 (M$^+$); $t_R$=3.73.

2-Methoxy-6-methyl-4-morpholin-4-yl-phenylamine

Bis(dibenzylideneacetone)palladium (0.63 g) and (2'-dicyclohexylphosphanyl-biphenyl-2-yl)-dimethyl-amine (0.68 g) were added to dry toluene (100 mL purged with argon) and stirred for 15 minutes under argon. Potassium tert-butoxide (3.70 g), morpholine (4.0 mL) and 4-bromo-2-methoxy-6-methyl-phenylamine (3.40 g) were added subsequently. The reaction mixture was heated to reflux for 16 hours under argon, cooled and filtered through silica (50 g). Sodium hydroxide (2 M, 200 mL) was added and the mixture was extracted with ethyl acetate (3×200 mL). The combined organic phases were washed with brine (1x 200 mL), dried over magnesium sulfate and concentrated in vacuo. The crude product was purified by flash chromatography to furnish 1.0 g (29% yield) of the title compound as a black oil. $^1$H NMR (500 MHz, DMSO-d$_6$): 2.05 (s, 3H), 2.91 (t, 4H), 3.69 (t, 4H), 3.74 (s, 3H), 3.95 (s, 2H), 6.23 (d, 1H), 6.39 (d, 1H).

The following compound was prepared analogously:

2-Methyl-4-morpholin-4-yl-6-trifluoromethyl-phenylamine

Yield: 28%. $^1$H NMR (500 MHz, DMSO-d$_6$): 2.13 (s, 3H), 2.93 (t, 4H), 3.70 (t, 4H), 4.67 (s, 2H), 6.75 (d, 1H), 6.99 (d, 1H).

4-(3,5-Difluoro-4-nitro-phenyl)-morpholine 2,4,6-Trifluoronitrobenzene (4.95 g) and potassium carbonate (4.63 g) were mixed in dry dimethyl sulfoxide (40 mL) and cooled to 10° C. under argon. Morpholine (2.56 mL) was added and the reaction mixture was allowed to warm to 25° C. and stirred under argon for 16 hours. The reaction mixture was concentrated in vacuo. Brine (50 mL) was added and the product was extracted with ethyl acetate (3×50 mL). The combined organic phases were dried over magnesium sulfate and concentrated in vacuo. The crude material was purified by flash chromatography to furnish 2.49 g (37% yield) of the title compound as a yellow solid. $^1$H NMR (500 MHz, DMSO-d$_6$): 3.43 (t, 4H), 3.69 (t, 4H), 6.87 (d, 2H).

2,6-Difluoro-4-morpholin-4-yl-phenylamine

Concentrated hydrochloric acid (4.2 mL) was added slowly to a mixture of zinc dust (3.3 g) and 4-(3,5-difluoro-4-nitro-phenyl)-morpholine (2.49 g) in tetrahydrofuran (40 mL) cooled to 0° C. The reaction mixture was then stirred for 1 hour at 0° C. and 2 hours at 25° C. The reaction mixture was filtered through Celite (10 g), concentrated in vacuo and purified by flash chromatography to furnish 1.96 g (90% yield) of the title compound as a white solid. GC-MS (m/z)

214 (M$^+$); $t_R$=5.83. $^1$H NMR (500 MHz, DMSO-d$_6$): 2.94 (t, 4H), 3.69 (t, 4H), 4.53 (s, 2H), 6.57 (m, 2H).

2-Chloro-4-nitro-6-trifluoromethyl-phenylamine

4-Nitro-2-trifluoromethyl-phenylamine (5.6 g) and N-chlorosuccinimide (4.0 g) were suspended in acetonitrile (15 mL) and heated to 150° C. for 10 minutes in a sealed microwave process vial. Ethyl acetate (80 mL) was added and the organic phase was washed with 5% aqueous NaOH (2×50 mL), water (2×50 mL) and brine (2×50 mL). The organic phase was dried over magnesium sulfate and concentrated in vacuo. The crude product was purified by flash chromatography to furnish 4.9 g (75% yield) of the title compound as a yellow solid. $^1$H NMR (500 MHz, CDCl$_3$): 5.35 (b, 2H), 8.35 (b, 1H), 8.37 (b, 1H).

The following compound was prepared analogously:

2-Chloro-6-methyl-4-nitro-phenylamine

Yield: 95%. $^1$H NMR (500 MHz, DMSO-d$_6$): 2.22 (s, 3H), 6.56 (b, 2H), 7.89 (d, 1H), 8.00 (d, 1H).

N-(2-Chloro-6-methyl-4-nitro-phenyl)-2-cyclopentyl-acetamide

2-Chloro-6-methyl-4-nitro-phenylamine (6.0 g) and cyclopentylacetyl chloride (5.1 g) were dissolved in acetonitrile (45 mL) and heated to 150° C. for 20 minutes in a sealed microwave process vessel. The reaction mixture was cooled to 0° C. and the precipitated product collected by filtration and washed with cold acetonitrile to furnish 5.5 g (58%) of the title compound as a yellow solid. $^1$H NMR (500 MHz, DMSO-d$_6$): 1.24 (m, 2H), 1.58 (m, 4H), 1.78 (m, 2H), 2.27 (m, 1H), 2.30 (s, 3H), 2.38 (d, 2H), 8.15 (d, 1H), 8.18 (d, 1H), 9.83 (s, 1H).

The following compound was prepared analogously:

N-(2-Chloro-6-methyl-4-nitro-phenyl)-2-(3-fluoro-phenyl)-acetamide

Yield: 72%. $^1$H NMR (500 MHz, DMSO-d$_6$): 2.24 (s, 3H), 3.77 (s, 2H), 7.10 (dt, 1H), 7.21 (m, 2H), 7.39 (m, 1H), 8.14 (d, 1H), 8.19 (d, 1H), 10.15 (s, 1H).

2-Chloro-6-trifluoromethyl-benzene-1,4-diamine

Acetic acid (13 mL) was added slowly to a mixture of zinc dust (12.4 g) and 2-chloro-4-nitro-6-trifluoromethyl-phenylamine (4 g) in tetrahydrofuran (40 mL). The reaction mixture was stirred for 1 hour, filtered through silica and concentrated in vacuo. The crude product was purified by flash chromatography to furnish 2.9 g (83%) of the title compound as a black solid. $^1$H NMR (500 MHz, CDCl$_3$): 3.44 (b, 2H), 4.16 (b, 2H), 6.77 (d, 1H), 6.86 (d, 1H).

The following compounds were prepared analogously:

N-(4-Amino-2-chloro-6-methyl-phenyl)-2-cyclopentyl-acetamide

Yield: 69%. $^1$H NMR (500 MHz, DMSO-d$_6$): 1.21 (m, 2H), 1.57 (m, 4H), 1.76 (m, 2H), 2.00 (s, 3H), 2.23 (d, 2H), 2.26 (m, 1H), 5.23 (s, 2H), 6.36 (d, 1H), 6.48 (d, 1H), 8.98 (s, 1H).

N-(4-Amino-2-chloro-6-methyl-phenyl)-2-(3-fluoro-phenyl)-acetamide

Yield: 88%. $^1$H NMR (500 MHz, DMSO-d$_6$): 1.90 (s, 3H), 3.62 (s, 2H), 5.26 (s, 2H), 6.35 (d, 1H), 6.49 (d, 1H), 7.07 (dt, 1H), 7.20 (m, 2H), 7.37 (m, 1H), 9.34 (s, 1H).

2-Chloro-4-morpholin-4-yl-6-trifluoromethyl-phenylamine

2-Chloro-6-trifluoromethyl-benzene-1,4-diamine (2.9 g), bis-(2-chloroethyl)ether (1.7 mL) and sodium iodide (516 mg) were mixed in acetonitrile (45 mL) and heated to 165° C. for 1 hour in a sealed microwave process vessel. The crude mixture was concentrated in vacuo, redissolved in ethyl acetate (100 mL) and washed with water (2×100 mL) and brine (1×100 mL). The organic phase was dried over magnesium sulfate and concentrated in vacuo. The crude product was purified by flash chromatography to furnish 940 mg (24%) of the title compound as a black oil. $^1$H NMR (500 MHz, CDCl$_3$): 3.02 (m, 4H), 3.84 (m, 4H), 4.30 (b, 2H), 6.97 (d, 1H), 7.06 (d, 1H).

N-(2,6-Diisopropyl-4-nitro-phenyl)-4-methyl-benzenesulfonamide 2,6-Diisopropyl-phenylamine (1.80 mL) and para-toluenesulfonyl chloride (2.00 g) were dissolved in pyridine (4 mL) and heated to 160° C. for 10 minutes in a sealed microwave process vial. The resulting slurry was diluted with ethyl acetate (10 mL) and washed with hydrochloric acid (2 M, 10 mL) and brine (10 mL). The organic phase was dried over Sodium sulfate, concentrated in vacuo and suspended in 65% nitric acid (15 mL) and water (60 mL). Acetic acid (60 mL) and sodium nitrite (0.99 g) were added successively and the reaction mixture was heated to 100° C. for 12 hours. The mixture was cooled to 25° C. and poured into ice water (200 mL) and filtered to furnish 2.07 g (58%) of the title compound as a yellow solid. $^1$H NMR (500 MHz, CDCl$_3$): 1.06 (d, 12H), 2.43 (s, 3H), 3.19 (m, 2H), 6.29 (s, 1H), 7.28 (d, 2H), 7.59 (d, 2H), 7.97 (s, 2H).

N-(4-Amino-2,6-diisopropyl-phenyl)-4-methyl-benzenesulfonamide

To a suspension of N-(2,6-diisopropyl-4-nitro-phenyl)-4-methyl-benzenesulfonamide (3.72 g) in ethanol (50 mL) was added stannous(II) chloride dihydrate (11.2 g) and the mixture was heated to −80° C. for 1.5 hour. It was then poured onto ice (300 mL), made strongly basic with solid sodium hydroxide (20 g) and diluted with ethyl acetate (100 mL). The suspension was filtered and extracted with ethyl acetate (3×100 mL). The combined organic phases were dried over sodium sulfate and concentrated in vacuo. The crude product was purified by flash chromatography to furnish 2.60 g (76%) of the title compound as an off-white solid. $^1$H NMR (500 MHz, CDCl$_3$): 0.95 (d, 12H), 2.40 (s, 3H), 3.02 (m, 2H), 3.68 (b, 2H), 5.74 (s, 1H), 6.39 (s, 2H), 7.23 (d, 2H), 7.60 (d, 2H).

2,6-Diisopropyl-4-morpholin-4-yl-phenylamine

A mixture of N-(4-amino-2,6-diisopropyl-phenyl)-4-methyl-benzenesulfonamide (346 mg), bis-(2-bromoethyl)ether (151 µL), N,N-diisopropyl-ethylamine (0.53 mL) and N-methylpyrrolidine (1.0 mL) was heated to 180° C. for 20 minutes in a sealed microwave process vial. The mixture was diluted with ethyl acetate (20 mL), washed with brine (30 mL) and saturated aqueous potassium carbonate (30 mL) and dried over sodium sulfate. The organic phase was concentrated in vacuo and redissolved in a mixture of sulfuric acid (1.9 mL) and water (0.1 mL) and stirred at 40° C. for 3 hours. Ice (30 mL) and water (30 mL) were added and the mixture was basified with solid potassium carbonate. The mixture was extracted with ethyl acetate (3×20 mL) and the combined organic phases were dried over sodium sulfate and concentrated in vacuo to furnish 260 mg (99%) of the title compound as a white solid. $^1$H NMR (500 MHz, CDCl$_3$): 1.26 (d, 12H), 2.95 (m, 2H), 3.06 (m, 4H), 3.49 (b, 2H), 3.87 (m, 4H), 6.69 (s, 2H).

N-(2,6-Diethyl-4-nitro-phenyl)-4-methyl-benzene-sulfonamide 2,6-Diethyl-phenylamine (1.57 mL) and para-toluenesulfonyl chloride (2.00 g) were dissolved in pyridine (4 mL) and heated to 160° C. for 10 minutes in a sealed microwave process vial. The resulting slurry was diluted with ethyl acetate (10 mL) and washed with hydrochloric acid (2 M, 10 mL) and brine (10 mL). The organic phase was dried over sodium sulfate, concentrated in vacuo and suspended in 65% nitric acid (15 mL) and water (60 mL). Acetic acid (60 mL) and sodium nitrite (0.99 g) were added successively and the reaction mixture was heated to 100° C. for 12 hours. The mixture was cooled to 25° C. and poured into ice water (200 mL), basified with solid sodium hydroxide and extracted with ethyl acetate (3×50 mL). The combined organic phases were washed with brine (1×100 mL), dried over sodium sulfate and concentrated in vacuo to furnish 0.31 g (9%) of the title compound as a yellow syrup. $^1$H NMR (500 MHz, DMSO-d$_6$): 0.98 (t, 6H), 2.34 (s, 3H), 3.30 (m, 4H), 7.25 (d, 2H), 7.52 (d, 2H), 7.80 (s, 2H).

N-(4-Amino-2,6-diethyl-phenyl)-4-methyl-benzene-sulfonamide

A solution of sodium dithionite (772 mg) in water (6 mL) was added to a solution of N-(2,6-diethyl-4-nitro-phenyl)-4-methyl-benzenesulfonamide (309 mg) in tetrahydrofuran (6 mL) and the resulting mixture was stirred at 50° C. for 20 hours. After cooling, the water was saturated with potassium carbonate and extracted with ethyl acetate (2×10 mL). The combined organic phases were dried over sodium sulfate, concentrated in vacuo and purified by flash chromatography to furnish 70 mg (25%) of the title compound as a off-white solid. The product was used directly in the following reaction without spectral characterization.

N-(2,6-Diethyl-4-morpholin-4-yl-phenyl)-4-methyl-benzenesulfonamide

A mixture of N-(4-amino-2,6-diethyl-phenyl)-4-methyl-benzenesulfonamide (70 mg), bis-(2-bromoethyl)ether (33 µL), N,N-diisopropyl-ethylamine (115 µL) and N-methylpyrrolidine (0.3 mL) was heated to 180° C. for 20 minutes in a sealed microwave process vial. The mixture was diluted with ethyl acetate (20 mL), washed with brine (30 mL) and saturated aqueous potassium carbonate (30 mL), and dried over sodium sulfate. The organic phase was concentrated in vacuo to furnish 78 mg (91%) of the title compound. LC-MS (m/z) 389 (MH$^+$); t$_R$=2.77, (UV, ELSD) 57%, 98%. The crude product was used without further purification.

(3,4-Difluoro-phenyl)-acetyl chloride

To (3,4-difluoro-phenyl)-acetic acid (2.0 g) dissolved in 1,2-dichloroethane (5 mL) was added thionyl chloride (5 mL) and the mixture was refluxed for 16 hours under argon. The crude mixture was concentrated in vacuo to furnish 2.2 g (100%) of the title compound as a yellow oil. $^1$H NMR (500 MHz, CDCl$_3$): 4.10 (s, 2H), 7.00 (m, 1H), 7.11 (m, 1H), 7.17 (m, 1H).

The following compound was prepared analogously:

(3-Fluoro-phenyl)-acetyl chloride

Yield: 99%. $^1$H NMR (500 MHz, CDCl$_3$): 4.13 (s, 2H), 6.92 (m, 1H), 7.01 (m, 2H), 7.34 (m, 1H).

Compounds of the Invention

Acid addition salts of the compounds of the invention may easily be formed by methods known to the person skilled in the art.

Example 1

1a N-(2-Bromo-4-morpholin-4-yl-6-trifluoromethyl-phenyl)-2-(4-fluoro-phenyl)-acetamide 2-Bromo-4-morpholin-4-yl-6-trifluoromethyl-phenylamine (0.236 g) and 4-fluorophenylacetyl chloride (0.105 mL) were dissolved in acetonitrile (5 mL) and heated to 150° C. for 10 minutes in a sealed microwave process vial. Water (25 mL) was added and the product was extracted with ethyl acetate (3×25 mL). The organic phases were washed with brine (50 mL), dried over magnesium sulfate and concentrated in vacuo. The crude product was purified by flash chromatography to furnish 0.027 g (9%) of the title compound as an off-white solid. LC-MS (m/z) 462 (MH$^+$); t$_R$=2.84, (UV, ELSD) 96%, 100%. $^1$H NMR (500 MHz, DMSO-d$_6$): 3.23 (m, 4H), 3.62 (s, 2H), 3.72 (m, 4H), 7.14 (dd, 2H), 7.19 (d, 1H), 7.35 (dd, 2H), 7.46 (d, 1H), 9.78 (s, 1H).

The following compounds were prepared analogously:

1b 2-Cyclopentyl-N-(2-bromo-6-trifluoromethyl-4-morpholin-4-yl-phenyl)-acetamide Yield: 22%. LC-MS (m/z) 436 (MH$^+$); t$_R$=2.95, (UV, ELSD) 97%, 98%. NMR (500 MHz, DMSO-d$_6$): 1.20 (m, 2H), 1.50 (m, 2H), 1.60 (m, 2H), 1.77 (m, 2H), 2.24 (m, 1H), 2.26 (d, 2H), 3.23 (m, 4H), 3.72 (m, 4H), 7.19 (d, 1H), 7.46 (d, 1H), 9.46 (s, 1H).

1c N-(2-Bromo-4-morpholin-4-yl-6-trifluoromethyl-phenyl)-3-cyclopentyl-propionamide Yield: 20%. LC-MS (m/z) 450 (MH$^+$); t$_R$=3.20, (UV, ELSD) 99%, 98%. $^1$H NMR (500 MHz, DMSO-d$_6$): 1.09 (m, 2H), 1.49 (m, 2H), 1.59 (m, 4H), 1.76 (m, 2H), 1.80 (m, 1H), 2.27 (t, 2H), 3.22 (m, 4H), 3.72 (m, 4H), 7.18 (d, 1H), 7.46 (d, 1H), 9.48 (s, 1H).

1d N-(2-Chloro-6-cyano-4-morpholin-4-yl-phenyl)-3-cyclohexyl-propionamide

Yield: 24%. LC-MS (m/z) 376 (MH$^+$); t$_R$=3.10, (UV, ELSD) 98%, 100%. $^1$H NMR (500 MHz, DMSO-d$_6$): 0.90 (m, 2H), 1.23 (m, 4H), 1.51 (m, 2H), 1.64 (m, 1H), 1.70 (m, 4H), 2.33 (t, 2H), 3.22 (m, 4H), 3.71 (m, 4H), 7.37 (s, 2H), 9.79 (s, 1H).

1e N-(2-Bromo-4-morpholin-4-yl-6-trifluoromethyl-phenyl)-3-cyclohexyl-propionamide Yield: 19%. LC-MS (m/z) 464 (MH$^+$); t$_R$=3.38, (UV, ELSD) 97%, 99%. $^1$H NMR (500 MHz, DMSO-d$_6$): 0.86 (dq, 2H), 1.16 (m, 3H), 1.27 (m, 1H), 1.48 (q, 2H), 1.61 (m, 1H), 1.70 (m, 4H), 2.27 (t, 2H), 3.23 (m, 4H), 3.72 (m, 4H), 7.18 (d, 1H), 7.46 (d, 1H), 9.47 (s, 1H).

1f N-(2-Bromo-4-morpholin-4-yl-6-trifluoromethyl-phenyl)-2-(3-fluoro-phenyl)-acetamide Yield: 44%. LC-MS (m/z) 462 (MO; $t_R$=2.85, (UV, ELSD) 98%, 99%. $^1$H NMR (500 MHz, DMSO-$d_6$): 3.23 (m, 4H), 3.67 (s, 2H), 3.72 (m, 4H), 7.10 (m, 2H), 7.18 (m, 2H), 7.36 (m, 1H), 7.46 (m, 1H), 9.82 (s, 1H).

1g N-(2-Bromo-4-morpholin-4-yl-6-trifluoromethyl-phenyl)-propionamide

Yield: 41%. LC-MS (m/z) 382 (MH$^+$); $t_R$=2.16, (UV, ELSD) 99%, 99%. $^1$H NMR (500 MHz, DMSO-$d_6$): 1.09 (t, 3H), 2.27 (q, 2H), 3.23 (m, 4H), 3.72 (m, 4H), 7.19 (d, 1H), 7.47 (d, 1H), 9.46 (s, 1H).

1h N-(2-Bromo-4-morpholin-4-yl-6-trifluoromethyl-phenyl)-butyramide

Yield: 76%. LC-MS (M/z) 396 (MH$^+$); $t_R$=2.43, (UV, ELSD) 99%; 96%. $^1$H NMR (500 MHz, DMSO-$d_6$): 0.93 (t, 3H), 1.60 (m, 2H), 2.24 (t, 2H), 3.23 (m, 4H), 3.72 (m, 4H), 7.18 (d, 1H), 7.46 (d, 1H), 9.45 (s, 1H).

1i N-(2-Chloro-4-morpholin-4-yl-6-trifluoromethyl-phenyl)-2-(3-fluoro-phenyl)-acetamide Yield: 21%. LC-MS (m/z) 417 (MH$^+$); $t_R$=2.84, (UV, ELSD) 97%, 99%. $^1$H NMR (500 MHz, DMSO-$d_6$): 3.23 (m, 4H), 3.67 (s, 2H), 3.72 (m, 4H), 7.07 (dt, 1H), 7.15 (m, 3H), 7.32 (d, 1H), 7.36 (m, 1H), 9.76 (s, 1H).

1j N-(2-Chloro-4-morpholin-4-yl-6-trifluoromethyl-phenyl)-2-cyclopentyl-acetamide Yield: 76%. LC-MS (m/z) 391 (MH$^+$); $t_R$=2.97, (UV, ELSD) 99%, 99%. $^1$H NMR (500 MHz, DMSO-$d_6$): 1.19 (m, 2H), 1.50 (m, 2H), 1.60 (m, 2H), 1.76 (m, 2H), 2.23 (m, 1H), 2.26 (d, 2H), 3.23 (m, 4H), 3.72 (m, 4H), 7.15 (d, 1H), 7.32 (d, 1H), 9.40 (s, 1H).

Example 2

2a 2-Cyclopentyl-N-(2,6-dimethyl-4-thiomorpholin-4-yl-phenyl)-acetamide

Bis(dibenzylideneacetone)palladium (37 mg) and (2'-dicyclohexylphosphanyl-biphenyl-2-yl)-dimethyl-amine (38 mg) were mixed in dry degassed toluene (2 mL) under argon for 5 minutes. To this mixture were added N-(4-bromo-2,6-dimethyl-phenyl)-2-cyclopentyl-acetamide (200 mg), potassium tert-butoxide (90 mg) and thiomorpholine (80 mg) and the reaction mixture was heated to 90° C. in a sealed 4 mL vial under argon for 16 hours, cooled and filtered through silica (2 g). Water/brine (1:1, 4 mL total) was added and the mixture was extracted with ethyl acetate (3×2 mL). The combined organic phases were dried over magnesium sulfate and concentrated in vacuo. The crude product was purified by preparative LC-MS to furnish 5.6 mg (3% yield) of the title compound. LC-MS-TOF (m/z) 333 (MIT); $t_R$=2.03, (UV, ELSD) 98%, 100%.

The following compounds were prepared analogously:

2b 2-Cyclopentyl-N-[2,6-dimethyl-4-(2-phenyl-morpholin-4-yl)-phenyl]-acetamide

Yield: 3%. LC-MS-TOF (m/z) 393 (MH$^+$); $t_R$=3.11, (UV, ELSD) 96%, 98%.

2c 2-Cyclopentyl-N-[2,6-dimethyl-4-(2-phenyl-thiomorpholin-4-yl)-phenyl]acetamide Yield: 4%. LC-MS-TOF (m/z) 409 (MH$^+$); $t_R$=3.30, (UV, ELSD) 99%, 98%.

2d 2-Cyclopentyl-N-[2,6-dimethyl-4-(3-pyridin-3-yl-thiomorpholin-4-yl)-phenyl]-acetamide Yield: 12%. LC-MS-TOF (m/z) 410 (Min; $t_R$=2.00, (UV, ELSD) 99%, 100%.

2e 2-Cyclopentyl-N-{2,6-dimethyl-4-[2-(4-trifluoromethyl-phenyl)-thiomorpholin-4-yl]-phenyl}-acetamide Yield: 6%. LC-MS (m/z) 477 (MH$^+$); $t_R$=3.64, (UV, ELSD) 95%, 100%.

2f N-(4-[2-(2-Chloro-phenyl)-thiomorpholin-4-yl]-2,6-dimethyl-phenyl)-2-cyclopentyl-acetamide Yield: 20%. LC-MS-TOF (m/z) 444 (MH$^+$); $t_R$=3.59, (UV, ELSD) 89%, 100%.

2g 2-Cyclopentyl-N-{2,6-dimethyl-4-[2-(4-trifluoromethyl-phenyl)-morpholin-4-yl]-phenyl}-acetamide Yield: 26%. LC-MS (m/z) 461 (MH$^+$); $t_R$=3.55, (UV, ELSD) 90%, 95%.

2h N-{4-[2-(2-Chloro-phenyl)-morpholin-4-yl]-2,6-dimethyl-phenyl}-2-cyclopentyl-acetamide Yield: 35%. LC-MS (m/z) 427 (MH$^+$); $t_R$=3.44, (UV, ELSD) 77%, 95%.

2i 2-Cyclopentyl-N-{4-[2-(4-fluoro-phenyl)-morpholin-4-yl]-2,6-dimethyl-phenyl}-acetamide Yield: 17%. LC-MS (M/z) 411 (MH$^+$); $t_R$=3.17, (UV, ELSD) 98%, 99%.

Example 3

3a 2-Bicyclo[2.2.1]hept-2-yl-N-(2,6-dimethyl-4-morpholin-4-yl-phenyl)-acetamide

Bicyclo[2.2.1]hept-2-yl-acetic acid (0.41 g) was heated to 50° C. for 2 hours under argon in a 1:1 mixture of thionyl chloride and 1,2-dichloroethane (10 mL total). The solvents were removed in vacuo and the resulting acid chloride was redissolved in acetonitrile (5 mL) and 2,6-dimethyl-4-morpholin-4-yl-phenylamine (0.50 g) was added. The reaction mixture was heated to 150° C. for 10 minutes in a sealed microwave process vial. Water (25 mL) was added and the product was extracted with ethyl acetate (3×25 mL). The combined organic phases were washed with brine (50 mL), dried over magnesium sulfate and concentrated in vacuo. The crude product was purified by flash chromatography to furnish 0.074 g (9%) of the title compound as an off-white solid. LC-MS-TOF (m/z) 343 (MH⁺); t$_R$=2.21, (UV, ELSD) 98%, 100%. ¹H NMR (500 MHz, DMSO-d$_6$): 1.14 (m, 4H), 1.41 (m, 4H), 1.90 (m, 1H), 2.02 (m, 1H), 2.06 (s, 6H), 2.10 (m, 1H), 2.20 (m, 2H), 3.05 (m, 4H), 3.71 (m, 4H), 6.62 (s, 2H), 8.92 (s, 1H).

The following compounds were prepared analogously:

3b 2-Cyclohexyl-N-(2,6-dimethyl-4-morpholin-4-yl-phenyl)-acetamide

Yield: 19%. LC-MS-TOF (m/z) 331 (MH⁺); t$_R$=2.21, (UV, ELSD) 97%, 100%. ¹H NMR (500 MHz, DMSO-d$_6$): 0.98 (m, 2H), 1.22 (m, 4H), 1.68 (m, 6H), 2.07 (s, 6H), 2.15 (d, 2H), 3.05 (m, 4H), 3.71 (m, 4H), 6.63 (s, 2H), 8.93 (s, 1H).

3c 3-(3,4-Difluoro-phenyl)-N-(2,6-dimethyl-4-morpholin-4-yl-phenyl)-propionamide Yield: 40%. LC-MS-TOF (m/z) 375 (MK); t$_R$=2.39, (UV, ELSD) 97%, 100%. ¹H NMR (500 MHz, DMSO-d$_6$): 1.95 (s, 6H), 2.60 (t, 2H), 2.91 (t, 2H), 3.04 (m, 4H), 3.71 (m, 4H), 6.60 (s, 2H), 7.10 (m, 1H), 7.34 (m, 2H), 8.97 (s, 1H).

Example 4

4a 2-Cyclopentyl-N-(2,6-dimethyl-4-morpholin-4-yl-phenyl)-acetamide 2,6-Dimethyl-4-morpholin-4-yl-phenylamine (0.50 g) and cyclopentylacetyl chloride (0.53 mL) were dissolved in acetonitrile (5 mL) and heated to 150° C. for 10 minutes in a sealed microwave process vial. Water (25 mL) was added and the product was extracted with ethyl acetate (3×25 mL). The organic phases were washed with brine (50 mL), dried over magnesium sulfate and concentrated in vacuo. The crude product was purified by flash chromatography to furnish 0.138 g (20%) of the title compound as an off-white solid. LC-MS-TOF (m/z) 317 (MH⁺); t$_R$=1.93, (UV, ELSD) 95%, 100%. ¹H NMR (500 MHz, DMSO-d$_6$): 1.21 (m, 2H), 1.52 (m, 2H), 1.61 (m, 2H), 1.76 (m, 2H), 2.07 (s, 6H), 2.11 (m, 1H), 2.25 (d, 2H), 3.05 (dd, 4H), 3.71 (dd, 4H), 6.63 (s, 2H), 8.94 (s, 1H).

The following compounds were prepared analogously:

4b (2,6-Dimethyl-4-morpholin-4-yl-phenyl)-carbamic acid butyl ester

Yield: 2%. LC-MS-TOF (m/z) 307 (MH⁺); t$_R$=2.25, (UV/ELSD) 99%, 100%.

4c 2-(4-Chloro-phenyl)-N-(2,6-dimethyl-4-morpholin-4-yl-phenyl)-acetamide

Yield: 8%. LC-MS-TOF (m/z) 359 (MH⁺); t$_R$=2.16, (UV, ELSD) 98%, 100%. ¹H NMR (500 MHz, DMSO-d$_6$): 2.01 (s, 6H), 3.04 (dd, 4H), 3.60 (s, 2H), 3.71 (dd, 4H), 6.62 (s, 2H), 7.39 (m, 4H), 9.24 (s, 1H).

4d 2,3-Dihydro-benzofuran-2-carboxylic acid (2,6-dimethyl-4-morpholin-4-yl-phenyl)-amide Yield: 13%. LC-MS-TOF (m/z) 353 (MH⁺); t$_R$=2.11, (UV, ELSD) 97%, 100%. ¹H NMR (500 MHz, DMSO-d$_6$): 2.01 (s, 6H), 3.05 (dd, 4H), 3.30 (m, 1H), 3.55 (dd, 1H), 3.71 (dd, 4H), 5.31 (dd, 1H), 6.64 (s, 2H), 6.88 (t, 2H), 7.15 (t, 1H), 7.25 (d, 1H), 9.33 (s, 1H).

4e 3-Cyclohexyl-N-(2,6-dimethyl-4-morpholin-4-yl-phenyl)-propionamide

Yield: 8%. LC-MS-TOF (m/z) 345 (MH⁺); t$_R$=2.64, (UV, ELSD) 97%, 98%. ¹H NMR (500 MHz, DMSO-d$_6$): 0.88 (m, 2H), 1.16 (m, 2H), 1.25 (m, 2H), 1.49 (q, 2H), 1.63 (m, 1H), 1.69 (m, 4H), 2.06 (s, 6H), 2.27 (t, 2H), 3.05 (dd, 4H), 3.71 (dd, 4H), 6.63 (s, 2H), 8.95 (s, 1H).

4f 3-Cyclopentyl-N-(2,6-dimethyl-4-morpholin-4-yl-phenyl)-propionamide

Yield: 34%. LC-MS (m/z) 331 (MH⁺); t$_R$=2.33, (UV, ELSD) 97%, 100%. ¹H NMR (500 MHz, DMSO-d$_6$): 1.11 (m, 2H), 1.49 (m, 2H), 1.60 (m, 4H), 1.77 (m, 2H), 2.07 (s, 6H), 2.28 (t, 2H), 3.11 (dd, 4H), 3.73 (dd, 4H), 6.74 (s, 2H), 9.01 (s, 1H).

4g N-(2,6-Dimethyl-4-morpholin-4-yl-phenyl)-2-(4-fluoro-phenyl)-acetamide

Yield: 13%. LC-MS-TOF (m/z) 343 (MO; t$_R$=2.05, (UV, ELSD) 98%, 100%. ¹H NMR (500 MHz, DMSO-d$_6$): 2.01 (s, 6H), 3.05 (m, 4H), 3.59 (s, 2H), 3.70 (m, 4H), 6.61 (s, 2H), 7.16 (dd, 2H), 7.38 (dd, 2H), 9.22 (s, 1H).

4h N-(2,6-Dimethyl-4-morpholin-4-yl-phenyl)-2-thiophen-2-yl-acetamide

Yield: 3%. LC-MS-TOF (m/z) 331 (MH⁺); t$_R$=1.94, (UV, ELSD) 97%, 100%.

4i N-(2,6-Dimethyl-4-morpholin-4-yl-phenyl)-3,3-dimethyl-butyramide

Yield: 43%. LC-MS-TOF (m/z) 305 (MH⁺); t$_R$=2.14, (UV, ELSD) 99%, 100%. ¹H NMR (500 MHz, DMSO-d$_6$): 1.05 (s, 9H), 2.09 (s, 6H), 2.17 (s, 2H), 3.05 (m, 4H), 3.72 (m, 4H), 6.63 (s, 2H), 8.89 (s, 1H).

4j Hexanoic acid (2,6-dimethyl-4-morpholin-4-yl-phenyl)-amide

Yield: 14%. LC-MS (m/z) 305 (MH⁺); t$_R$=1.99, (UV, ELSD) 95%, 97%. ¹H NMR (500 MHz, DMSO-d$_6$): 0.88 (t, 3H), 1.31 (m, 4H), 1.60 (m, 2H), 2.06 (s, 6H), 2.26 (t, 2H), 3.05 (m, 4H), 3.71 (m, 4H), 6.63 (s, 2H), 8.94 (s, 1H).

Example 5

5a 2-Cycloheptyl-N-(2,6-dimethyl-4-morpholin-4-yl-phenyl)-acetamide

Cycloheptyl-acetic acid (0.45 g) and one drop of N,N-dimethylformamide was stirred at 25° C. for 2 hours under argon in a 1:1 mixture of oxalyl chloride (2 M in dichloromethane) and 1,2-dichloroethane (12 mL total). The solvents were removed in vacuo and the resulting acid chloride was redissolved in acetonitrile (8 mL) and 2,6-dimethyl-4-morpholin-4-yl-phenylamine (0.50 g) and magnesium oxide (0.20 g) were added. The reaction mixture was stirred at 25° C. for 16 hours under argon and then filtered through Celite (10 g). The organic phase was concentrated in vacuo and the crude product was purified by flash chromatography to furnish 0.133 g (16%) of the title compound as an off-white solid. LC-MS (m/z) 345 (MH$^+$); $t_R$=2.36, (UV, ELSD) 97%, 100%. $^1$H NMR (500 MHz, DMSO-$d_6$): 1.23 (m, 2H), 1.44 (m, 4H), 1.60 (m, 4H), 1.73 (m, 2H), 1.99 (m, 1H), 2.07 (s, 6H), 2.18 (d, 2H), 3.05 (m, 4H), 3.71 (m, 4H), 6.63 (s, 2H), 8.94 (s, 1H).

Example 6

6a
(2,6-Dimethyl-4-morpholin-4-yl-phenyl)-carbamic acid benzyl ester

Benzyl chloroformate (32 mg) was added to a solution of 0.15 M 2,6-dimethyl-4-morpholin-4-yl-phenylamine and 0.30 M N,N-diisopropyl-ethylamine in 1,2-dichloroethane (1 mL). The vial was shaken for 16 hours and concentrated in vacuo. Aqueous sodium hydroxide (1 M, 2 mL) was added and the crude mixture was extracted with isopropyl acetate/tetrahydrofuran (4:1, 2.5 mL). The organic phase was concentrated in vacuo and redissolved in dimethyl sulfoxide (0.5 mL) of which 0.2 mL was subjected to preparative LC-MS purification to furnish 9.5 mg (47% yield) of the title compound as an oil. LC-MS (m/z) 341 (MH$^+$); $t_R$=2.28, (UV, ELSD) 100%, 100%.

The following compounds were prepared analogously:

6b (2,6-Dimethyl-4-morpholin-4-yl-phenyl)-carbamic acid 2-chloro-benzyl ester

Yield: 33%. LC-MS (m/z) 375 (MH$^+$); $t_R$=2.53, (UV, ELSD) 99%, 100%.

6c 3,5,5-Trimethyl-hexanoic acid (2,6-dimethyl-4-morpholin-4-yl-phenyl)-amide

Yield: 36%. LC-MS (m/z) 347 (MH$^+$); $t_R$=2.53, (UV, ELSD) 99%, 100%.

6d Octanoic acid (2,6-dimethyl-4-morpholin-4-yl-phenyl)-amide

Yield: 47%. LC-MS (m/z) 333 (MI-r); $t_R$=2.47, (UV, ELSD) 99%, 100%.

6e Heptanoic acid (2,6-dimethyl-4-morpholin-4-yl-phenyl)-amide

Yield: 40%. LC-MS (m/z) 319 (MH$^+$); $t_R$=2.20, (UV, ELSD) 91%, 99%.

6f N-(2,6-Dimethyl-4-morpholin-4-yl-phenyl)-2-phenyl-acetamide

Yield: 35%. LC-MS (m/z) 325 (MH$^+$); $t_R$=1.80, (UV, ELSD) 99%, 100%.

Example 7

7a 2-(3,4-Dichloro-phenyl)-N-(2,6-dimethyl-4-morpholin-4-yl-phenyl)-acetamide 3,4-Dichlorophenylacetic acid (39 mg) was stirred at 25° C. for 2 hours under argon in a 1:1 mixture of oxalyl chloride (2 M in dichloromethane) and 1,2-dichloroethane (1 mL total). The solvents were removed in vacuo and a solution of 0.15 M 2,6-dimethyl-4-morpholin-4-yl-phenylamine and 0.30 M N,N-diisopropyl-ethylamine in 1,2-dichloroethane (1 mL) was added to the resulting acid chloride. The vial was shaken for 16 hours and concentrated in vacuo. Aqueous sodium hydroxide (1 M, 2 mL) was added and the crude mixture was extracted with isopropyl acetate/tetrahydrofuran (4:1, 2.5 mL). The organic phase was concentrated in vacuo and redissolved in dimethyl sulfoxide (0.5 mL) of which 0.2 mL was subjected to preparative LC-MS purification to furnish 2.7 mg (11% yield) of the title compound as an oil. LC-MS (m/z) 394 (MH$^+$); $t_R$=2.40, (UV, ELSD) 80%, 100%.

The following compounds were prepared analogously:

7b 2-(4-Allyloxy-3-chloro-phenyl)-N-(2,6-dimethyl-4-morpholin-4-yl-phenyl)-acetamide Yield: 14%. LC-MS (m/z) 415 (MH$^+$); $t_R$=2.40, (UV, ELSD) 91%, 100%

7c N-(2,6-Dimethyl-4-morpholin-4-yl-phenyl)-2-(3-trifluoromethyl-phenyl)-acetamide Yield: 18%. LC-MS (m/z) 393 (MH$^+$); $t_R$=2.31, (UV, ELSD) 97%, 100%.

7d N-(2,6-Dimethyl-4-morpholin-4-yl-phenyl)-2-naphthalen-2-yl-acetamide

Yield: 16%. LC-MS (m/z) 375 (MH$^+$); $t_R$=2.27, (UV, ELSD) 83%, 100%.

7e 3-(3-Chloro-phenyl)-N-(2,6-dimethyl-4-morpholin-4-yl-phenyl)-propionamide

Yield: 10%. LC-MS (m/z) 373 (MH$^+$); $t_R$=2.23, (UV, ELSD) 71%, 94%.

7f N-(2,6-Dimethyl-4-morpholin-4-yl-phenyl)-2-(3,4-dimethyl-phenyl)-acetamide

Yield: 44%. LC-MS (m/z) 353 (MH$^+$); $t_R$=2.21, (UV, ELSD) 80%, 100%.

7g 2-(3-Bromo-phenyl)-N-(2,6-dimethyl-4-morpholin-4-yl-phenyl)-acetamide

Yield: 22%. LC-MS (m/z) 404 (MH$^+$); $t_R$=2.19, (UV, ELSD) 95%, 100%.

7h 2-(3-Chloro-phenyl)-N-(2,6-dimethyl-4-morpholin-4-yl-phenyl)-acetamide

Yield: 25%. LC-MS (m/z) 359 (MH$^+$); $t_R$=2.13, (UV, ELSD) 95%, 100%.

7i N-(2,6-Dimethyl-4-morpholin-4-yl-phenyl)-2-p-tolyl-acetamide

Yield: 26%. LC-MS (m/z) 339 (MH$^+$); $t_R$=2.04, (UV, ELSD) 99%, 100%.

7j N-(2,6-Dimethyl-4-morpholin-4-yl-phenyl)-2-m-tolyl-acetamide

Yield: 24%. LC-MS (m/z) 339 (MH$^+$); $t_R$=2.03, (UV, ELSD) 88%, 100%.

7k 2-(3,4-Difluoro-phenyl)-N-(2,6-dimethyl-4-morpholin-4-yl-phenyl)-acetamide Yield: 24%. LC-MS (m/z) 361 (MH$^+$); $t_R$=2.03, (UV, ELSD) 99%, 100%.

7l N-(2,6-Dimethyl-4-morpholin-4-yl-phenyl)-2-(3-fluoro-phenyl)-acetamide

Yield: 12%. LC-MS (m/z) 343 (MH$^+$); $t_R$=1.90, (UV, ELSD) 88%, 97%.

7m 2-(2-Chloro-phenyl)-N-(2,6-dimethyl-4-morpholin-4-yl-phenyl)-acetamide

Yield: 2%. LC-MS (m/z) 359 (MH$^+$); $t_R$=2.01, (UV, ELSD) 98%, 99%.

7n Pentanoic acid (2,6-dimethyl-4-morpholin-4-yl-phenyl)-amide

Pentanoic acid (0.37 g), N,N-diisopropyl-ethylamine (1.51 mL) and N-[(dimethylamino)-1H-1,2,3-triazolo-[4,5-b]pyridin-1-yl-methylene]-N-methyl-methanaminium hexafluorophosphate N-oxide (1.66 g) were mixed in dry N,N-dimethylformamide (3 mL) and stirred under argon for 2 minutes. 2,6-Dimethyl-4-morpholin-4-yl-phenylamine (0.50 g) dissolved in dry N,N-dimethylformamide (2 mL) was added to the reaction mixture, which was stirred at 25° C. under argon for 16 hours. Ethyl acetate (20 mL) was added and the organic phase was washed with saturated aqueous ammonium chloride/water (1:1, 20 mL), water (20 mL), brine/water (1:1, 20 mL), dried over magnesium sulfate, concentrated in vacuo and purified by flash chromatography to furnish 0.28 g (40% yield) of the title compound as a white solid. LC-MS (m/z) 291 (MH$^+$); $t_R$=1.61, (UV, ELSD) 99%, 99%. $^1$H NMR (500 MHz, DMSO-d$_6$): 0.91 (t, 3H), 1.34 (m, 2H), 1.58 (qui, 2H), 2.06 (s, 6H), 2.27 (t, 2H), 3.04 (t, 4H), 3.71 (t, 4H), 6.62 (s, 2H), 8.94 (s, 1H).

The following compounds were prepared analogously:

7o 4-Methyl-pentanoic acid (2,6-dimethyl-4-morpholin-4-yl-phenyl)-amide

Yield: 28%. LC-MS (m/z) 305 (MH$^+$); $t_R$=1.88, (UV, ELSD) 98%, 99%. $^1$H NMR (500 MHz, DMSO-d$_6$): 0.91 (d, 6H), 1.49 (m, 2H), 1.57 (m, 1H), 2.06 (s, 6H), 2.27 (t, 2H), 3.05 (t, 4H), 3.71 (t, 4H), 6.63 (s, 2H), 8.95 (s, 1H).

7p 2-Cyclopent-2-enyl-N-(2,6-dimethyl-4-morpholin-4-yl-phenyl)-acetamide

Yield: 69%. LC-MS (m/z) 315 (MH$^+$); $t_R$=1.82, (UV, ELSD) 97%, 99%. $^1$H NMR (500 MHz, DMSO-d$_6$): 1.51 (m, 2H), 2.06 (m, 1H), 2.08 (s, 6H), 2.23 (m, 1H), 2.29 (m, 1H), 2.34 (m, 2H), 3.05 (m, 4H), 3.72 (m, 4H), 5.73 (m, 1H), 5.76 (m, 1H), 6.63 (s, 2H), 8.98 (s, 1H).

7q 5-Methyl-hexanoic acid (2,6-dimethyl-4-morpholin-4-yl-phenyl)-amide

Yield: 41%. LC-MS (m/z) 319 (MH$^+$); $t_R$=2.18, (UV, ELSD) 96%, 99%. $^1$H NMR (500 MHz, DMSO-d$_6$): 0.87 (d, 6H), 1.21 (m, 2H), 1.59 (m, 3H), 2.07 (s, 6H), 2.24 (t, 2H), 3.05 (t, 4H), 3.72 (t, 4H), 6.63 (s, 2H), 8.94 (s, 1H).

7r 3-Methyl-pentanoic acid (2,6-dimethyl-4-morpholin-4-yl-phenyl)-amide

Yield: 31%. LC-MS (m/z) 305 (MH$^+$); $t_R$=1.86, (UV, ELSD) 98%, 99%. $^1$H NMR (500 MHz, DMSO-d$_6$): 0.89 (t, 3H), 0.93 (d, 3H), 1.22 (m, 1H), 1.39 (m, 1H), 1.88 (m, 1H), 2.07 (s, 6H), 2.26 (m, 1H), 3.05 (t, 4H), 3.72 (t, 4H), 6.63 (s, 2H), 8.95 (s, 1H).

7s Hex-5-enoic acid (2,6-dimethyl-4-morpholin-4-yl-phenyl)-amide

Yield: 68%. LC-MS (m/z) 303 (MH$^+$); $t_R$=1.71, (UV, ELSD) 99%, 99%. $^1$H NMR (500 MHz, DMSO-d$_6$): 1.69 (qui, 2H), 2.07 (s, 6H), 2.09 (m, 2H), 2.28 (t, 2H), 3.05 (t, 4H), 3.71 (t, 4H), 4.99 (dd, 1H), 5.04 (dd, 1H), 5.84 (m, 1H), 6.63 (s, 2H), 8.95 (s, 1H).

7t 3-Ethyl-pentanoic acid (2,6-dimethyl-4-morpholin-4-yl-phenyl)-amide

3-Ethylpentanoic acid (0.79 g) and thionyl chloride (0.44 mL) were mixed in acetonitrile (10 mL) and heated to 110° C. for 5 minutes in a sealed microwave process vial. 2,6-Dimethyl-4-morpholin-4-yl-phenylamine (1:25 g) dissolved in acetonitrile (10 mL) was added to the reaction mixture and heated to 150° C. for 15 minutes in a sealed microwave process vial. Saturated aqueous sodium bicarbonate/brine/water (1:1:1, 50 mL) was added to the crude mixture and it was extracted with ethyl acetate (3×50 mL). The combined organic phases were dried over magnesium sulfate and concentrated in vacuo. The crude product was recrystallized from hot toluene, and the product was collected by filtration, washed with cold toluene and dried in vacuo to furnish 0.59 g (30% yield) of the title compound as an off-white solid. LC-MS (m/z) 319 (MH$^+$); $t_R$=2.04, (UV, ELSD) 98%, 99%. $^1$H NMR (500 MHz, DMSO-d$_6$): 0.87 (t, 6H), 1.35 (qui, 4H), 1.76 (m, 1H), 2.07 (s, 6H), 2.20 (d, 2H), 3.05 (t, 4H), 3.71 (t, 4H), 6.62 (s, 2H), 8.94 (s, 1H).

Example 8

8a 2-Cyclopentyl-N-(4-morpholin-4-yl-2-pyridin-3-yl-6-trifluoromethyl-phenyl)-acetamide 2-Cyclopentyl-N-(2-bromo-6-trifluoromethyl-4-morpholin-4-yl-phenyl)-acetamide (1b, 15 mg), 3-pyridylboronic acid (21 mg), aqueous potassium carbonate (5 M, 90 µL) and palladium(II) acetate (1 mg) were mixed in acetone (2 mL) and heated to 130° C. for 20 minutes in a sealed microwave process vial. The reaction mixture was filtered through silica (500 mg), concentrated in vacuo, redissolved in dimethyl sulfoxide (0.5 mL) and subjected to preparative LC-MS purification to furnish 2.7 mg (18% yield) of the title compound as a colorless oil. LC-MS (m/z) 434 (MH$^+$); $t_R$=1.89, (UV, ELSD) 99%, 99%.

The following compounds were prepared analogously:

8b 2-Cyclopentyl-N-(5-morpholin-4-yl-3-trifluoromethyl-biphenyl-2-yl)-acetamide Yield: 46%. LC-MS (m/z) 433 (MH$^+$); $t_R$=3.16, (UV, ELSD) 96%, 99%.

8c 2-Cyclopentyl-N-(4'-fluoro-5-morpholin-4-yl-3-trifluoromethyl-biphenyl-2-yl)-acetamide Yield: 20%. LC-MS (m/z) 451 (MH$^+$); $t_R$=3.18, (UV, ELSD) 99%, 99%.

8d 2-Cyclopentyl-N-(4'-methyl-5-morpholin-4-yl-3-trifluoromethyl-biphenyl-2-yl)-acetamide Yield: 51%. LC-MS (m/z) 447 (MH$^+$); $t_R$=3.32, (UV, ELSD) 97%, 99%.

8e 2-Cyclopentyl-N-(3'-methyl-5-morpholin-4-yl-3-trifluoromethyl-biphenyl-2-yl)-acetamide Yield: 37%. LC-MS (m/z) 447 (MH$^+$); $t_R$=3.33, (UV, ELSD) 99%, 99%.

8f 2-Cyclopentyl-N-(3',4'-difluoro-5-morpholin-4-yl-3-trifluoromethyl-biphenyl-2-yl)-acetamide Yield: 51%. LC-MS (m/z) 469 (MH$^+$); $t_R$=3.29, (UV, ELSD) 99%, 99%.

8g 2-(4-Fluoro-phenyl)-N-(4-morpholin-4-yl-2-pyridin-3-yl-6-trifluoromethyl-phenyl)-acetamide Yield: 25%. LC-MS (m/z) 460 (MH$^+$); $t_R$=1.81, (UV, ELSD) 94%, 99%.

Example 9

9a 2-Cyclopentyl-N-(2,6-diethyl-4-morpholin-4-yl-phenyl)-acetamide

N-(2,6-Diethyl-4-morpholin-4-yl-phenyl)-4-methyl-benzenesulfonamide (78 mg), sulfuric acid (0.95 mL) and water (50 µL) were stirred at 40° C. for 3 hours. Ice (30 mL) and water (30 mL) were added and the mixture was basified with solid potassium carbonate. The mixture was extracted with ethyl acetate (3×20 mL), the combined organic phases were dried over sodium sulfate and concentrated in vacuo. The residue was redissolved in tetrahydrofuran (1 mL) and mixed with pyridine (49 µL) and cyclopentylacetyl chloride (44 µL). The mixture was stirred for 1 hour at 25° C., diluted with ethyl acetate (20 mL) and washed with 10% aqueous sodium bicarbonate (20 mL) and brine (20 mL). The organic phase was dried over sodium sulfate, concentrated in vacuo and purified by flash chromatography to furnish 35 mg (51%) of the title compound as a tan solid. LC-MS (m/z) 345 (MH$^+$); $t_R$=2.27, (UV, ELSD) 84%, 98%.

9b 2-Cyclopentyl-N-(2,6-diisopropyl-4-morpholin-4-yl-phenyl)-acetamide

To a solution of 2,6-diisopropyl-4-morpholin-4-yl-phenylamine (279 mg) and pyridine (245 µL) in tetrahydrofuran (2 mL) was added cyclopentylacetyl chloride (210 µL) and the mixture was stirred for 1 hour at 25° C. The reaction mixture was diluted with ethyl acetate (20 mL) and washed with 10% aqueous sodium bicarbonate (20 mL) and brine (20 mL). The organic phase was dried over sodium sulfate, concentrated in vacuo and purified by flash chromatography. Recrystallisation of the crude brown material from hot ethyl acetate/heptane furnished 122 mg (33%) of the title compound as a white solid. LC-MS (m/z) 373 (MH$^+$); $t_R$=2.58, (UV, ELSD) 98%, 99%. $^1$H NMR (500 MHz, CDCl$_3$): 1.19 (d, 12H), 1.27 (m, 2H), 1.60 (m, 2H), 1.68 (m, 2H), 1.93 (m, 2H), 2.40 (m, 1H), 2.41 (m, 2H), 3.05 (m, 2H), 3.17 (m, 4H), 3.87 (m, 4H), 6.49 (s, 1H), 6.70 (s, 2H).

Example 10

10a 2-Cyclopentyl-N-(2,6-difluoro-4-morpholin-4-yl-phenyl)-acetamide 2,6-Difluoro-4-morpholin-4-yl-phenylamine (0.20 g) and cyclopentylacetyl chloride (149 µL) were dissolved in acetonitrile (4 mL) and heated to 150° C. for 10 minutes in a sealed microwave process vial. The reaction mixture was concentrated in vacuo and purified by flash chromatography to furnish 228 mg (75%) of the title compound as a white solid. LC-MS (m/z) 325 (MH$^+$); $t_R$=2.61, (UV, ELSD) 99%, 99%. $^1$H NMR (500 MHz, DMSO-d$_6$): 1.19 (m, 2H), 1.51 (m, 2H), 1.60 (m, 2H), 1.74 (m, 2H), 2.19 (m, 1H), 2.26 (d, 2H), 3.14 (m, 4H), 3.70 (m, 4H), 6.68 (d, 2H), 9.20 (s, 1H).

The following compounds were prepared analogously:

10b Hexanoic acid (2,6-difluoro-4-morpholin-4-yl-phenyl)-amide

Yield: 84%. LC-MS (m/z) 313 (MH$^+$); $t_R$=2.60, (UV, ELSD) 99%, 98%. $^1$H NMR (500 MHz, DMSO-d$_6$): 0.87 (t, 3H), 1.29 (m, 4H), 1.57 (qui, 2H), 2.27 (t, 2H), 3.14 (t, 4H), 3.70 (t, 4H), 6.68 (d, 2H), 9.22 (s, 1H).

10c N-(2,6-Difluoro-4-morpholin-4-yl-phenyl)-3,3-dimethyl-butyramide

Yield: 58%. LC-MS (m/z) 313 (MH$^+$); $t_R$=2.49, (UV, ELSD) 99%, 99%. $^1$H NMR (500 MHz, DMSO-d$_6$): 1.02 (s, 9H), 2.15 (s, 2H), 3.14 (m, 4H), 3.71 (m, 4H), 6.68 (d, 2H), 9.15 (s, 1H).

10d N-(2,6-Difluoro-4-morpholin-4-yl-phenyl)-2-(3-fluoro-phenyl)-acetamide

Yield: 68%. LC-MS (m/z) 351 (MH$^+$); $t_R$=2.52, (UV, ELSD) 96%, 99%. $^1$H NMR (500 MHz, DMSO-d$_6$): 3.14 (t, 4H), 3.67 (s, 2H), 3.70 (t, 4H), 6.69 (d, 2H), 7.09 (m, 1H), 7.14 (m, 2H), 7.37 (m, 1H), 9.58 (s, 1H).

10e 2-Cyclopent-2-enyl-N-(2,6-difluoro-4-morpholin-4-yl-phenyl)-acetamide

Cyclopent-2-enylacetic acid (0.17 mL), N,N-diisopropylethylamine (0.50 mL) and N-[(dimethylamino)-1H-1,2,3-triazolo-[4,5-b]pyridin-1-yl-methylene]-N-methyl-methanaminium hexafluoro-phosphate N-oxide (0.55 g) were mixed in dry N,N-dimethylformamide (3 mL) and stirred under argon for 2 minutes. 2,6-Difluoro-4-morpholin-4-yl-phenylamine (0.20 g) dissolved in dry N,N-dimethylformamide (2 mL) was added to the reaction mixture, which was stirred at 25° C. under argon for 16 hours. Ethyl acetate (20 mL) was added and the organic phase was washed with saturated aqueous ammonium chloride/water (1:1, 20 mL), water (20 mL), brine/water (1:1, 20 mL), dried over magnesium sulfate, concentrated in vacuo and purified by flash chromatography to furnish 0.21 g (71% yield) of the title compound as a white solid. LC-MS (m/z) 323 (MH$^+$); $t_R$=2.49, (UV, ELSD) 96%, 99%. $^1$H NMR (500 MHz, DMSO-d$_6$): 1.48 (m, 1H), 2.02 (m, 1H), 2.29 (m, 4H), 3.03 (m, 1H), 3.14 (t, 4H), 3.71 (t, 4H), 5.71 (m, 1H), 5.76 (m, 1H), 6.68 (d, 2H), 9.25 (s, 1H).

The following compound was prepared analogously:

10f 2-Bicyclo[2.2.1]hept-2-yl-N-(2,6-difluoro-4-morpholin-4-yl-phenyl)-acetamide Yield: 56%. LC-MS (m/z) 351 (MH+); $t_R$=2.90, (UV, ELSD) 98%, 99%. $^1$H NMR (500 MHz, DMSO-$d_6$): 1.11 (m, 4H), 1.43 (m, 4H), 1.85 (m, 1H), 2.00 (m, 1H), 2.11 (m, 1H), 2.21 (m, 2H), 3.14 (t, 4H), 3.71 (t, 4H), 6.67 (d, 2H), 9.19 (s, 1H).

Example 11

11a 2-Bicyclo[2.2.1]hept-2-yl-N-(2-methyl-4-morpholin-4-yl-6-trifluoromethyl-phenyl)-acetamide Bicyclo[2.2.1]hept-2-yl-acetic acid (160 mg), N,N-diisopropyl-ethylamine (0.44 mL) and N-[(dimethylamino)-1H-1,2,3-triazolo-[4,5-b]pyridin-1-yl-methylene]-N-methyl-methanaminium hexafluoro-phosphate N-oxide (0.47 g) were mixed in dry N,N-dimethylformamide (3 mL) and stirred under argon for 2 minutes. 2-Methyl-4-morpholin-4-yl-6-trifluoromethyl-phenylamine (0.18 g) dissolved in dry N,N-dimethylformamide (2 mL) was added to the reaction mixture, which was stirred at 25° C. under argon for 16 hours. Ethyl acetate (20 mL) was added and the organic phase was washed with saturated aqueous ammonium chloride/water (1:1, 20 mL), water (20 mL), brine/water (1:1, 20 mL), dried over magnesium sulfate, concentrated in vacuo and purified by flash chromatography to furnish 16 mg (6% yield) of the title compound as a white solid. LC-MS (m/z) 397 (MH+); $t_R$=3.12, (UV, ELSD) 91%, 98%.

The following compounds were prepared analogously:

11b 5-Methyl-pentanoic acid (2-methyl-4-morpholin-4-yl-6-trifluoromethyl-phenyl)-amide.

Yield: 6%. LC-MS (m/z) 359 (MH+); $t_R$=2.76, (UV, ELSD) 94%, 99%.

11c 5-Methyl-hexanoic acid (2-methyl-4-morpholin-4-yl-6-trifluoromethyl-phenyl)-amide Yield: 6%. LC-MS (m/z) 373 (MH+); $t_R$=3.06, (UV, ELSD) 85%, 99%.

11d 2-Cyclopent-2-enyl-N-(2-methyl-4-morpholin-4-yl-6-trifluoromethyl-phenyl)-acetamide Yield: 25%. LC-MS (m/z) 369 (MH+); $t_R$=2.70, (UV, ELSD) 96%, 99%. $^1$H NMR (500 MHz, DMSO-$d_b$): 1.48 (m, 1H), 2.04 (m, 1H), 2.25 (m, 2H), 2.34 (m, 2H), 3.06 (m, 1H), 3.16 (t, 4H), 3.74 (t, 4H), 5.71 (m, 1H), 5.76 (m, 1H), 7.00 (m, 1H), 7.13 (m, 1H), 9.23 (s, 1H).

11e 2-Cyclopentyl-N-(2-methyl-4-morpholin-4-yl-6-trifluoromethyl-phenyl)-acetamide 2-Methyl-4-morpholin-4-yl-6-trifluoromethyl-phenylamine (0.18 g) and cyclopentylacetyl chloride (112 mg) were dissolved in acetonitrile (4 mL) and heated to 150° C. for 10 minutes in a sealed microwave process vial. The reaction mixture was diluted with ethyl acetate (20 mL) and washed with water (2×20 mL) and brine (1×20 mL). The organic phase was dried over magnesium sulfate, concentrated in vacuo and purified by flash chromatography to furnish 132 mg (52%) of the title compound as a white solid. LC-MS (m/z) 371 (MH+); $t_R$=2.87, (UV, ELSD) 99%, 99%. $^1$H NMR (500 MHz, DMSO-$d_6$): 1.20 (m, 2H), 1.51 (m, 2H), 1.60 (m, 2H), 1.76 (m, 2H), 2.11 (s, 3H), 2.24 (m, 1H), 2.26 (d, 2H), 3.16 (t, 4H), 3.73 (t, 4H), 7.00 (d, 1H), 7.12 (d, 1H), 9.16 (s, 1H).

The following compounds were prepared analogously:

11f Hexanoic acid (2-methyl-4-morpholin-4-yl-6-trifluoromethyl-phenyl)-amide

Yield: 64%. LC-MS (m/z) 359 (MH+); $t_R$=2.86, (UV, ELSD) 95%, 99%. $^1$H NMR (500 MHz, DMSO-$d_6$): 0.88 (t, 3H), 1.30 (m, 4H), 1.58 (qui, 2H), 2.11 (s, 3H), 2.26 (t, 2H), 3.16 (t, 4H), 3.73 (t, 4H), 6.99 (d, 1H), 7.11 (d, 1H), 9.17 (s, 1H).

11g 3,3-Dimethyl-N-(2-methyl-4-morpholin-4-yl-6-trifluoromethyl-phenyl)-butyramide Yield: 58%. LC-MS (m/z) 359 (MH+); $t_R$=2.76, (UV, ELSD) 97%, 99%. $^1$H NMR (500 MHz, DMSO-$d_6$): 1.03 (s, 9H), 2.13 (s, 3H), 2.18 (s, 2H), 3.16 (t, 4H), 3.73 (t, 4H), 7.00 (d, 1H), 7.12 (d, 1H), 9.12 (s, 1H).

11h 2-(3,4-Difluoro-phenyl)-N-(2-methyl-4-morpholin-4-yl-6-trifluoromethyl-phenyl)-acetamide Yield: 23%. LC-MS (m/z) 415 (MH+); $t_R$=2.77, (UV, ELSD) 97%, 99%. $^1$H NMR (500 MHz, DMSO-$d_6$): 2.03 (s, 3H), 3.16 (t, 4H), 3.63 (d, 2H), 3.72 (t, 4H), 7.00 (d, 1H), 7.11 (d, 1H), 7.17 (m, 1H), 738 (m, 2H), 9.52 (b, 1H).

11i Hexanoic acid (2-methoxy-6-methyl-4-morpholin-4-yl-phenyl)-amide

Yield: 87%. LC-MS (m/z) 321 (MH+); $t_R$=2.04, (UV, ELSD) 99%, 99%. $^1$H NMR (500 MHz, DMSO-$d_6$): 0.88 (t, 3H), 1.31 (m, 4H), 1.57 (qui, 2H), 2.04 (s, 3H), 2.23 (t, 2H), 3.13 (t, 4H), 3.71 (s, 3H), 3.75 (t, 4H), 6.43 (b, 1H), 6.49 (b, 1H), 8.78 (s, 1H).

11j 2-Cyclopentyl-N-(2-methoxy-6-methyl-4-morpholin-4-yl-phenyl)-acetamide

Yield: 81%. LC-MS (m/z) 333 (MH+); $t_R$=2.06, (UV, ELSD) 99%, 99%. $^1$H NMR (500 MHz, DMSO-$d_6$): 1.21 (m, 2H), 1.51 (m, 2H), 1.60 (m, 2H), 1.75 (m, 2H), 2.05 (s, 3H), 2.21 (m, 1H), 2.23 (d, 2H), 3.17 (m, 4H), 3.71 (s, 3H), 3.77 (m, 4H), 6.48 (b, 1H), 6.55 (b, 1H), 8.80 (s, 1H).

11k N-(2-Methoxy-6-methyl-4-morpholin-4-yl-phenyl)-3,3-dimethyl-butyramide

Yield: 90%. LC-MS (m/z) 321 (MH+); $t_R$=1.95, (UV, ELSD) 99%, 99%. $^1$H NMR (500 MHz, DMSO-$d_6$): 1.03 (s, 9H), 2.08 (s, 3H), 2.14 (s, 2H), 3.17 (m, 4H), 3.71 (s, 3H), 3.78 (m, 4H), 6.49 (b, 1H), 6.55 (b, 1H), 8.73 (s, 1H).

11l 2-(3,4-Difluoro-phenyl)-N-(2-methoxy-6-methyl-4-morpholin-4-yl-phenyl)-acetamide Yield: 41%. LC-MS (M/z) 377 (MH+); $t_R$=2.12, (UV, ELSD) 99%, 99%. $^1$H NMR (500 MHz, DMSO-$d_6$): 1.96 (s, 3H), 3.09 (t, 4H), 3.59 (s, 2H), 3.71 (s, 3H), 3.72 (t, 4H), 6.34 (d, 1H), 6.42 (d, 1H), 7.19 (m, 1H), 7.40 (m, 2H), 9.13 (s, 1H).

11m 2-Cyclopent-2-enyl-N-(2-methoxy-6-methyl-4-morpholin-4-yl-phenyl)-acetamide Yield: 27%. LC-MS (m/z) 331 (MH$^+$); $t_R$=1.91, (UV, ELSD) 96%, 99%. $^1$H NMR (500 MHz, DMSO-d$_6$): 1.51 (m, 1H), 2.04 (m, 1H), 2.05 (s, 3H), 2.22 (m, 2H), 2.29 (m, 2H), 3.04 (m, 1H), 3.13 (t, 4H), 3.71 (s, 3H), 3.75 (t, 4H), 5.74 (m, 2H), 6.43 (b, 1H), 6.49 (b, 1H), 8.82 (s, 1H).

11n 2-(3-Fluoro-phenyl)-N-(2-methoxy-6-methyl-4-morpholin-4-yl-phenyl)-acetamide Yield: 14%. LC-MS (m/z) 359 (MH$^+$); $t_R$=2.02, (UV, ELSD) 99%, 99%. $^1$H NMR (500 MHz, DMSO-d$_6$): 1.96 (s, 3H), 3.09 (t, 4H), 3.61 (s, 2H), 3.71 (s, 3H), 3.72 (t, 4H), 6.34 (d, 1H), 6.42 (d, 1H), 7.07 (dt, 1H), 7.19 (m, 2H), 7.36 (m, 1H), 9.13 (s, 1H).

11o 2-Bicyclo[2.2.1]hept-2-yl-N-(2-methoxy-6-methyl-4-morpholin-4-yl-phenyl)-acetamide Bicyclo[2.2.1]hept-2-yl-acetic acid (0.17 g) dissolved in oxalyl chloride (2 M in dichloromethane, 0.7 mL) was stirred at 25° C. for 2 hours under argon. The solvents were removed in vacuo and the resulting acid chloride was redissolved in acetonitrile (4 mL) and 2-methoxy-6-methyl-4-morpholin-4-yl-phenylamine (50 mg) was added. The reaction mixture was heated to 150° C. for 10 minutes in a sealed microwave process vial and then diluted with ethyl acetate (20 mL) and washed with water (2×20 mL) and brine (lx 20 mL). The organic phase was dried over magnesium sulfate, concentrated in vacuo and purified by flash chromatography to furnish 20 mg (25%) of the title compound as a white solid. LC-MS (m/z) 359 (MH$^+$); $t_R$=2.30, (UV, ELSD) 99%, 99%. $^1$H NMR (500 MHz, DMSO-d$_6$): 1.14 (m, 4H), 1.43 (m, 4H), 1.86 (m, 1H), 2.03 (s, 3H), 2.06 (m, 2H), 2.19 (m, 2H), 3.11 (t, 4H), 3.70 (s, 3H), 3.74 (t, 4H), 6.38 (b, 1H), 6.45 (b, 1H), 8.74 (s, 1H).

The following compounds were prepared analogously:

11p 4-Methyl-pentanoic acid (2-methoxy-6-methyl-4-morpholin-4-yl-phenyl)-amide Yield: 66%. LC-MS (M/z) 321 (MH$^+$); $t_R$=1.99, (UV, ELSD) 99%, 99%. $^1$H NMR (500 MHz, DMSO-d$_6$): 0.90 (d, 6H), 1.47 (m, 2H), 1.58 (m, 1H), 2.03 (s, 3H), 2.24 (t, 2H), 3.13 (m, 4H), 3.70 (s, 3H), 3.75 (m, 4H), 6.42 (b, 1H), 6.48 (b, 1H), 8.79 (s, 1H).

11q 5-Methyl-hexanoic acid (2-methoxy-6-methyl-4-morpholin-4-yl-phenyl)-amide Yield: 54%. LC-MS (m/z) 335 (MH$^+$); $t_R$=2.26, (UV, ELSD) 94%, 99%. $^1$H NMR (500 MHz, DMSO-d$_6$): 0.88 (d, 6H), 1.22 (m, 4H), 1.57 (m, 3H), 2.03 (s, 3H), 2.21 (t, 2H), 3.09 (t, 4H), 3.76 (s, 3H), 3.73 (t, 4H), 6.35 (d, 1H), 6.41 (d, 1H), 8.74 (s, 1H).

Example 12

12a N-(2-Chloro-6-methyl-4-morpholin-4-yl-phenyl)-2-(3-fluoro-phenyl)-acetamide N-(4-Amino-2-chloro-6-methyl-phenyl)-2-(3-fluoro-phenyl)-acetamide (616 mg), bis-(2-chloroethyl)ether (260 pt) and potassium iodide (400 mg) were mixed in dry N,N-dimethylformamide (11 mL) and heated to 180° C. for 30 minutes in a sealed microwave process vial. 5% aqueous sodium bicarbonate (100 mL) was added and the mixture was extracted with ethyl acetate (3×80 mL). The combined organic phases were washed with water (2×100 mL), brine (1×100 mL), dried over sodium sulfate and concentrated in vacuo. The crude product was purified by flash chromatography to furnish 236 mg (31%) of the title compound as a white solid. LC-MS (m/z) 363 (MH$^+$); $t_R$=2.56, (UV, ELSD) 96%, 99%. $^1$H NMR (500 MHz, DMSO-d$_6$): 2.04 (s, 3H), 3.10 (m, 4H), 3.65 (s, 2H), 3.70 (m, 4H), 6.79 (d, 1H), 6.85 (d, 1H), 7.07 (dt, 1H), 7.19 (m, 2H), 7.37 (m, 1H), 9.52 (s, 1H).

12b N-(2-Chloro-6-methyl-4-morpholin-4-yl-phenyl)-2-cyclopentyl-acetamide

N-(4-Amino-2-chloro-6-methyl-phenyl)-2-cyclopentyl-acetamide (830 mg), bis-(2-chloroethyl)ether (3.35 mL) and potassium iodide (470 mg) were mixed in absolute ethanol (33 mL) and heated to 170° C. for 1 hour in a sealed microwave process vial. The crude mixture was concentrated in vacuo and purified by flash chromatography to furnish 390 mg (41%) of the title compound as a white solid. LC-MS (m/z) 337 (MH$^+$); $t_R$=2.61, (UV, ELSD) 97%, 99%. $^1$H NMR (500 MHz, DMSO-d$_6$): 1.22 (m; 2H), 1.51 (m, 2H), 1.61 (m, 2H), 1.77 (m, 2H), 2.11 (s, 3H), 2.25 (m, 1H), 2.26 (m, 2H), 3.10 (m, 4H), 3.71 (m, 4H), 6.80 (d, 1H), 6.84 (d, 1H), 9.18 (s, 1H).

TABLE 1

Reagents used for the preparation of compounds in Examples 1-12.

| Name | Supplier | CAS no. | Cat. no. |
|---|---|---|---|
| (±)-2,2'-Bis(diphenylphosphino)-1,1'-binaphthyl | Aldrich | 76189-55-4 | 48,108-4 |
| (2'-dicyclohexylphosphanyl-biphenyl-2-yl)-dimethyl-amine | STREM | 213697-53-1 | 15-1145 |
| hydroquinine (anthraquinone-1,4-diyl)diether | Aldrich | — | 45,670-5 |
| 2-(2-Chlorophenyl)thiomorpholine hydrochloride | Array | — | 2TMA-S02-1 |
| 2,3-dihydro-1-benzofuran-2-carbonyl chloride | Maybridge | 27347-32-6 | CC23902 |
| 2,4,6-Trifluoronitrobenzene | Aldrich | 315-14-0 | 26,180-7 |
| 2,6-Diethylphenylamine | Aldrich | 579-66-8 | 14,938-1 |
| 2,6-Diisopropyl-phenylamine | Aldrich | 24544-04-5 | 37,473-3 |
| 2-[4-(Trifluoromethyl)phenyl]thiomorpholine hydrochloride | Array | — | 2TMA-Q07-1 |
| 2-Amino-3-chloro-5-nitro-benzonitrile | Acros | 20352-84-5 | 34367-0050 |
| 2-chlorobenzyl chloroformate | Aldrich | 39545-31-8 | 49,379-1 |
| 2-Chlorophenylacetic acid | Aldrich | 2444-36-2 | 19,063-2 |

TABLE 1-continued

Reagents used for the preparation of compounds in Examples 1-12.

| Name | Supplier | CAS no. | Cat. no. |
|---|---|---|---|
| 2-Chlorostyrene | Aldrich | 2039-87-4 | 16,067-9 |
| 2-Cyclopentene-1-acetic acid | Aldrich | 13668-61-6 | C11,285-2 |
| 2-Methoxy-6-methylphenylamine | Aldrich | 50868-73-0 | 36,009-0 |
| 2-Methyl-6-(trifluoromethyl)phenylamine | ABCR | — | F05171PF |
| 2-Naphthylacetic acid | Aldrich | 581-96-4 | 31,791-8 |
| 2-Phenylmorpholine hydrochloride | Array | — | 2FMA-0-1 |
| 2-Phenylthiomorpholine hydrochloride | Array | — | 2TMA-0-1 |
| 2-Pyridin-3-ylthiomorpholine hydrochloride | Array | — | 2TMA-P03-1 |
| 3-(3,4-Difluorophenyl)-propionyl acid | Aldrich | 161712-75-0 | 45,702-7 |
| 3-(3-Chlorophenyl)propionic acid | ABCR | 21640-48-2 | TWC2925 |
| 3-(Trifluoromethyl)phenylacetic acid | Aldrich | 351-35-9 | 19,335-6 |
| 3,4-Dichlorophenylacetic acid | Aldrich | 5807-30-7 | 28,000-3 |
| 3,4-Difluorophenylacetic acid | ABCR | 658-93-5 | F02874E |
| 3,4-difluorophenylboronic acid | Aldrich | 168267-41-2 | 46,508-9 |
| 3,4-Dimethylphenylacetic acid | Vitas-M | 17283-16-8 | TBB000367 |
| 3,5,5-Trimethylhexanoic acid | Acros | 3302-10-1 | 26944-0250 |
| 3-bromophenylacetic acid | Aldrich | 1878-67-7 | 28,886-1 |
| 3-Chlorophenylacetic acid | Aldrich | 1878-65-5 | C6,335-9 |
| 3-Cyclohexylpropionyl chloride | Acros | 39098-75-4 | 35071-0250 |
| 3-cyclohexylpropionyl chloride | Acros | 39098-75-4 | 35071-0250 |
| 3-Cyclopentylpropionyl chloride | Aldrich | 104-97-2 | 26,859-3 |
| 3-Ethylpentanoic acid | Narchem | 58888-87-2 | 58888-87-2 |
| 3-Fluorophenylacetic acid | Aldrich | 331-25-9 | 24,804-5 |
| 3-Methylpentanoic acid | Aldrich | 105-43-1 | 22,245-3 |
| 3-methylphenylboronic acid | Aldrich | 17933-03-8 | 39,361-4 |
| 4-(Trifluoromethyl)styrene | Aldrich | 402-50-6 | 36,960-8 |
| 4-Bromo-2,6-dimethylaniline | Aldrich | 24596-19-8 | 19,237-6 |
| 4-Chlorophenylacetyl chloride | Lancaster | 25026-34-0 | 6317 |
| 4-Fluorophenylacetyl chloride | Aldrich | 459-04-1 | 46,695-6 |
| 4-fluorophenylboronic acid | Aldrich | 1765-93-1 | 41,755-6 |
| 4-Fluorostyrene | Aldrich | 405-99-2 | 15,579-9 |
| 4-Methylpentanoic acid | Aldrich | 646-07-1 | 27,782-7 |
| 4-Nitro-2-(trifluoromethyl)-phenylamine | Aldrich | 121-01-7 | 19,657-6 |
| 4-Nitro-2-methyl-phenylamine | Aldrich | 99-52-5 | 14,643-9 |
| 4-tolylboronic acid | Aldrich | 5720-05-8 | 39,362-2 |
| 5-Hexenoic acid | Lancaster | 1577-22-6 | 12863 |
| 5-Methylhexanoic acid | Matrix | 628-46-6 | 3527 |
| Benzyl chloroformate | Aldrich | 501-53-1 | 11,993-8 |
| Bicyclo[2.2.1]hept-2-yl-acetic acid | Aldrich | 1007-01-8 | 12,726-4 |
| Bis-(2-bromoethyl)ether | Aldrich | 5414-19-7 | 38,220-5 |
| Bis-(2-chloroethyl)ether | Aldrich | 111-44-4 | C4,113-4 |
| Bis(dibenzylideneacetone)palladium | Acros | 32005-36-0 | 29197-0050 |
| Bromine | Aldrich | 7726-95-6 | 20,788-8 |
| Butyl chloroformate | Aldrich | 592-34-7 | 18,446-2 |
| Butyryl chloride | Aldrich | 141-75-3 | 23,634-9 |
| Carbamic acid tert-butyl ester | Aldrich | 4248-19-5 | 16,739-8 |
| Chloroacetyl chloride | Aldrich | 79-04-9 | 10,449-3 |
| Cycloheptylacetic acid | Lancaster | 4401-20-1 | 15553 |
| Cyclohexyl-acetic acid | Aldrich | 5292-21-7 | C10,450-7 |
| Cyclopentylacetyl chloride | Lancaster | 1122-99-2 | 14562 |
| Heptanoic acid | Aldrich | 111-14-8 | 14,687-0 |
| Hexanoyl chloride | Aldrich | 142-61-0 | 29,465-9 |
| Morpholine | Aldrich | 110-91-8 | 25,236-0 |
| m-Tolylacetic acid | Aldrich | 621-36-3 | T3,809-1 |
| N-[(Dimethylamino)-1H-1,2,3-triazolo[4,5-b]pyridin-1-ylmethylene]-N-methylmethanaminium hexafluorophosphate N-oxide | Fluka | 148893-10-1 | 11373 |
| N-Bromosuccinimide | Aldrich | 128-08-5 | B8,125-5 |
| Octanoic acid | Aldrich | 124-07-2 | 15,375-3 |
| Oxalyl chloride | Aldrich | 79-37-8 | 32,042-0 |
| palladium(II) acetate | Aldrich | 3375-31-3 | 20,586-9 |
| Pentanoyl chloride | Aldrich | 638-29-9 | 15,714-7 |
| Phenylacetyl chloride | Aldrich | 103-80-0 | P1,675-3 |
| phenylboronic acid | Aldrich | 98-80-6 | P2,000-9 |
| Potassium osmate(VI) dihydrate | Aldrich | 10022-66-9 | 20,910-4 |
| Propionyl chloride | Aldrich | 79-03-8 | P5,155-9 |
| p-Toluenesulfonyl chloride | Aldrich | 98-59-9 | T3,595-5 |
| p-Tolylacetic acid | Aldrich | 622-47-9 | T3,810-5 |
| Pyridine-3-boronic acid | Asymchem | 1692-25-7 | 111347 |
| Sodium bis(2-methoxyethoxy)aluminium hydride (70% in toluene) | Aldrich | 22722-98-1 | 19,619-3 |
| Sodium dithionite | Aldrich | 7775-14-6 | 15,795-3 |
| Stannous(II) chloride dihydrate | Aldrich | 10025-69-1 | 20,803-5 |
| Tert-butyl hypochlorite | VWR | 507-40-4 | 081328 |
| Tert-butylacetyl chloride | Aldrich | 7065-46-5 | B8,880-2 |
| Thiomorpholine | Aldrich | 123-90-0 | 19,627-4 |

TABLE 1-continued

Reagents used for the preparation of compounds in Examples 1-12.

| Name | Supplier | CAS no. | Cat. no. |
|---|---|---|---|
| Thionyl chloride | Aldrich | 7719-09-7 | 23,046-4 |
| Thiophene-2-acetyl chloride | Aldrich | 39098-97-0 | 19,599-5 |

In vitro and in vivo Testing

The compounds of the invention have been tested and shown effect in one or more of the below models:

Relative Efflux Through the KCNQ2 Channel.

This exemplifies a KCNQ2 screening protocol for evaluating compounds of the present invention. The assay measures the relative efflux through the KCNQ2 channel, and was carried out according to a method described by Tang et al. (Tang, W. et. al., *J. Biomol. Screen.* 2001, 6, 325-331) for hERG potassium channels with the modifications described below.

An adequate number of CHO cells stably expressing voltage-gated KCNQ2 channels were plated at a density sufficient to yield a mono-confluent layer on the day of the experiment. Cells were seeded on the day before the experiment and loaded with 1 μCi/ml [$^{86}$Rb] over night. On the day of the experiment cells were washed with a HBSS-containing buffer. Cells were pre-incubated with drug for 30 minutes and the $^{86}$Rb$^+$ efflux was stimulated by a submaximal concentration of 15 mM KCl in the continued presence of drug for additional 30 minutes. After a suitable incubation period, the supernatant was removed and counted in a liquid scintillation counter (Tricarb). Cells were lysed with 2 mM NaOH and the amount of $^{86}$Rb$^+$ was counted. The relative efflux was calculated $((CPM_{super}/(CPM_{super}+CPM_{cell})_{Cmpd}/(CPM_{super}/(CPM_{super}+CPM_{cell}))_{15mM\,KCl})*100-100$.

The compounds of the invention have an EC$_{50}$ of less than 20000 nM, in most cases less than 2000 nM and in many cases less than 200 nM. Accordingly, the compounds of the invention are considered to be useful in the treatment of diseases associated with the KCNQ family potassium channels.

Electrophysiological Patch-clamp Recordings in CHO Cells

Voltage-activated KCNQ2 currents were recorded from mammalian CHO cells by use of conventional patch-clamp recordings techniques in the whole-cell patch-clamp configuration (Hamill O P et. al. *Pflügers Arch* 1981; 391: 85-100). CHO cells with stable expression of voltage-activated KCNQ2 channels were grown under normal cell culture conditions, in CO$_2$ incubators and used for electrophysiological recordings 1-7 days after plating. KCNQ2 potassium channels were activated by voltage steps up to +80 mV in increments of 5-20 mV (or with a ramp protocol) from a membrane holding potential between −100 mV and −40 mV (Tatulian L et al. *J Neuroscience* 2001; 21 (15): 5535-5545). The electrophysiological effects induced by the compounds were evaluated on various parameters of the voltage-activated KCNQ2 current. Especially effects on the activation threshold for the current and on the maximum induced current were studied.

Some of the compounds of the invention have been tested in this test: A left-ward shift of the activation threshold or an increase in the maximum induced potassium current is expected to decrease the activity in neuronal networks and thus make the compounds useful in diseases with increased neuronal activity-like epilepsia.

Electrophysiological Recordings of KCNQ2, KCNQ2/KCNQ3 or KCNQ5 Channels in Oocytes Voltage-activated KCNQ2, KCNQ2/KCNQ3 or KCNQ5 currents were recorded from *Xenopus oocytes* injected with mRNA coding for KCNQ2, KCNQ2+KCNQ3 or KCNQ5 ion channels (Wang et al., Science 1998, 282, 1890-1893; Lerche et al., *J Biol Chem* 2000, 275, 22395-400). KCNQ2, KCNQ2/KCNQ3 or KCNQ5 potassium channels were activated by voltage steps from the membrane holding potential (between −100 mV and −40 mV) up to +40 mV in increments of 5-20 mV (or by a ramp protocol). The electrophysiological effects induced by the compounds were evaluated on various parameters of the voltage-activated KCNQ2, KCNQ2/KCNQ3 or KCNQ5 currents. Especially effects on the activation threshold for the current and on the maximum induced current were studied.

The hyperpolarizing effects of some of the compounds were also tested directly on the membrane potential during current clamp.

Maximum Electroshock

The test was conducted in groups of male mice using corneal electrodes and administering a square wave current of 26 mA for 0.4 seconds in order to induce a convulsion characterised by a tonic hind limb extension (Wlaz et al. *Epilepsy Research* 1998, 30, 219-229).

Pilocarpine Induced Seizures

Pilocarpine induced seizures are induced by intraperitoneal injection of pilocarpine 250 mg/kg to groups of male mice and observing for seizure activity resulting in loss of posture within a period of 30 minutes (Starr et al. *Pharmacology Biochemistry and Behavior* 1993, 45, 321-325).

Electrical Seizure—Threshold Test

A modification of the up-and-down method (Kimball et al. *Radiation Research* 1957, 1-12) was used to determine the median threshold to induce tonic hind-limb extension in response to corneal electroshock in groups of male mice. The first mouse of each group received an electroshock at 14 mA, (0.4 s, 50 Hz) and was observed for seizure activity. If a seizure was observed the current was reduced by 1 mA for the next mouse, however, if no seizure was observed then the current was increased by 1 mA. This procedure was repeated for all 15 mice in the treatment group.

Chemical Seizure—Threshold Test

The threshold dose of pentylenetetrazole required to induce a clonic convulsion was measured by timed infusion of pentylenetetrazole (5 mg/mL at 0.5 mL/minute) into a lateral tail vein of groups of male mice (Nutt et al. *J. Pharmacy and Pharmacology* 1986, 38, 697-698).

Amygdala Kindling

Rats underwent surgery to implantation of tri-polar electrodes into the dorsolateral amygdala. After surgery the animals were allowed to recover before the groups of rats received either varying doses of test compound or the drug's vehicle. The animals were stimulated with their initial after discharge threshold+25 μA daily for 3-5 weeks and on each occasion seizure severity, seizure duration, and duration of electrical after discharge were noted. (Racine, *Electroencephalography and Clinical Neurophysiology* 1972, 32, 281-294).

Side Effects

Central nervous system side-effects were measured by measuring the time mice would remain on rotarod apparatus (Capacio et al. Drug and Chemical Toxicology 1992, 15, 177-201); or by measuring their locomotor activity by counting the number of infra-red beams crossed in a test cage (Watson et al. Neuropharmacology 1997, 36, 1369-1375). Hypothermic actions on the animals core body temperature of the compound were measured by either rectal probe or implanted radiotelemetry transmitters capable of measuring temperature (Keeney et al. Physiology and Behaviour 2001, 74, 177-184).

Pharmacokinetics

The pharmacokinetic properties of the compound were determined via. i.v. and p.o. dosing to Sprague Dawley rats, and, thereafter, drawing blood samples over 20 hours. Plasma concentrations were determined with LC/MS/MS.

The invention claimed is:

1. A method of treating epilepsy comprising administering an anti-convulsive and a compound of formula I:

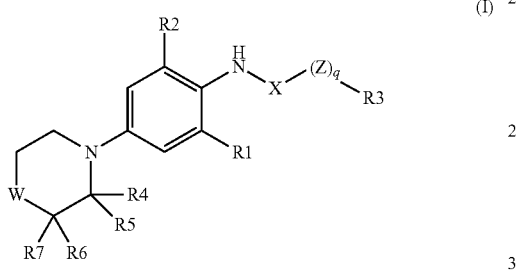

wherein
q is 0 or 1;
W is O;
X is CO;
Z is O;
R1 is selected from the group consisting of halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, $C_{1-6}$-alk(en/yn)yloxy, $C_{3-8}$-cycloalk(en)yloxy and $C_{3-8}$-cycloalk(en)yl-$C_{1-6}$-alk(en/yn)yloxy;
R2 is selected from the group consisting of halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, $C_{1-6}$-alk(en/yn)yloxy, $C_{3-8}$-cycloalk(en)yloxy, $C_{3-8}$-cycloalk(en)yl-$C_{1-6}$-alk(en/yn)yloxy, optionally substituted phenyl and optionally substituted pyridyl; wherein phenyl and pyridyl are optionally substituted with one or more substituents independently being halogen, $C_{1-6}$-alk(en/yn)yl, $C_{3-8}$-cycloalk(en)yl or $C_{3-8}$-cycloalk(en)yl-$C_{1-6}$-alk(en/yn)yl;
R3 is selected from the group consisting of $C_{1-10}$-alk(en/yn)yl, $C_{3-8}$-cycloalk(en)yl, $C_{3-8}$-cycloalk(en)yl-$C_{1-6}$-alk(en/yn)yl, Ar—$C_{1-6}$-alk(en/yn)yl, Ar—$C_{3-8}$-cycloalk(en)yl, Ar—$C_{3-8}$-cycloalk(en)yl-$C_{1-6}$-alk(en/yn)yl and Ar; and
each of R4, R5, R6 and R7 is independently selected from the group consisting of hydrogen and Ar;
wherein Ar is selected from the group consisting of phenyl, naphthyl, pyridine, optionally substituted thiophene, furan, thiazole, quinoline, indole, 2,3-dihydro-benzofuran, pyrimidine, pyrrole and oxazole; in which the Ar is optionally substituted with one or more substituents independently being hydroxy, halogen, $C_{1-6}$-alk(en/yn)yl, $C_{3-8}$-cycloalk(en)yl, $C_{3-8}$-cycloalk(en)yl-$C_{1-6}$-alk(en/yn)yl, halo-$C_{1-6}$-alk(en/yn)yl, $C_{1-6}$-alk(en/yn)yloxy, $C_{3-8}$-alk(en/yn)yloxy, acyl, nitro or cyano, —CO—NH—$C_{1-6}$-alk(en/yn)yl, —CO—N($C_{1-6}$-alk(en/yn)yl)$_2$, —NH$_2$, —NH—$C_{1-6}$-alk(en/yn)yl, —N($C_{1-6}$-alk(en/yn)yl)$_2$, —S—$C_{1-6}$-alk(en/yn)yl, —SO$_2$—$C_{1-6}$-alk(en/yn)yl, —SO$_2$N($C_{1-6}$-alk(en/yn)yl)$_2$ and —SO$_2$NH—$C_{1-6}$-alk(en/yn)yl; or two adjacent substituents may together with the aromatic group to which they are attached form a 4-8 membered ring, which optionally contains one, two or three heteroatoms; when Ar is substituted with CO—NH—$C_{1-6}$-alk(en/yn)yl or CO—N($C_{1-6}$-alk(en/yn)yl)$_2$, then the carbon atom of the CO group is attached to Ar; when Ar is substituted with NH$_2$, NH—$C_{1-6}$-alk(en/yn)yl or N($C_{1-6}$-alk(en/yn)yl)$_2$, then the nitrogen atom is attached to Ar; when Ar is substituted with —S—$C_{1-6}$-alk(en/yn)yl, —SO$_2$—$C_{1-6}$-alk(en/yn)yl), —SO$_2$N($C_{1-6}$-alk(en/yn)yl)$_2$ or —SO$_2$NH—$C_{1-6}$-alk(en/yn)yl then the sulphur atom is attached to Ar;
or a salt thereof.

2. The method according to claim 1 wherein q is 0.

3. The method according to claim 1 wherein q is 1.

4. The method according to claim 1, wherein R1 is selected from the group consisting of halogen, cyano, $C_{1-6}$-alk(en/yn)yl, halo-$C_{1-6}$-alk(en/yn)yl and $C_{1-6}$-alk(en/yn)yloxy.

5. The method according to claim 1, wherein R2 is selected from the group consisting of halogen, cyano, $C_{1-6}$-alk(en/yn)yl, halo-$C_{1-6}$-alk(en/yn)yl, $C_{1-6}$-alk(en/yn)yloxy, optionally substituted phenyl and optionally substituted pyridyl.

6. The method according to claim 1, wherein optionally substituted phenyl and optionally substituted pyridyl may be substituted with one or more substituents independently being halogen or $C_{1-6}$-alk(en/yn)yl.

7. The method according to claim 1, wherein R3 is selected from the group consisting of $C_{1-10}$-alk(en/yn)yl, $C_{3-8}$-cycloalk(en)yl-$C_{1-6}$-alk(en/yn)yl, Ar—$C_{1-6}$-alk(en/yn)yl and Ar.

8. The method according to claim 1, wherein any Ar may be substituted with one or more substituents independently being halogen, $C_{1-6}$-alk(en/yn)yl, halo-$C_{1-6}$-alk(en/yn)yl or $C_{1-6}$-alk(en/yn)yloxy.

9. The method according to claim 1, wherein
q is 0 or 1;
W is O;
X is CO;
Z is O;
R1 and R2 are independently selected from the group consisting of halogen, halo-$C_{1-6}$-alk(en/yn)yl, $C_{1-6}$-alk(en/yn)yl and cyano;
R3 is selected from the group consisting of $C_{1-10}$-alk(en/yn)yl, $C_{3-8}$-cycloalk(en)yl-$C_{1-6}$-alk(en/yn)yl, Ar—$C_{1-6}$-alk(en/yn)yl and Ar; and
R4, R5, R6 and R7 are independently selected from the group consisting of hydrogen and Ar;
or a salt thereof.

10. A compound according to claim 1, said compound being selected from the group consisting of:
N-(2-Bromo-4-morpholin-4-yl-6-trifluoromethyl-phenyl)-2-(4-fluoro-phenyl)-acetamide;
2-Cyclopentyl-N-(2-bromo-6-trifluoromethyl-4-morpholin-4-yl-phenyl)-acetamide;
N-(2-Bromo-4-morpholin-4-yl-6-trifluoromethyl-phenyl)-3-cyclopentyl-propionamide;
N-(2-Chloro-6-cyano-4-morpholin-4-yl-phenyl)-3-cyclohexyl-propionamide;
2-Cyclopentyl-N-[2,6-dimethyl-4-(2-phenyl-morpholin-4-yl)-phenyl]-acetamide;

2-Bicyclo[2.2.1]hept-2-yl-N-(2,6-dimethyl-4-morpholin-4-yl-phenyl)-acetamide;
2-Cyclohexyl-N-(2,6-dimethyl-4-morpholin-4-yl-phenyl)-acetamide;
3-(3,4-Difluoro-phenyl)-N-(2,6-dimethyl-4-morpholin-4-yl-phenyl)-propionamide;
2-Cyclopentyl-N-(2,6-dimethyl-4-morpholin-4-yl-phenyl)-acetamide;
(2,6-Dimethyl-4-morpholin-4-yl-phenyl)-carbamic acid butyl ester;
2-(4-Chloro-phenyl)-N-(2,6-dimethyl-4-morpholin-4-yl-phenyl)-acetamide;
2,3-Dihydro-benzofuran-2-carboxylic acid (2,6-dimethyl-4-morpholin-4-yl-phenyl)-amide;
3-Cyclohexyl-N-(2,6-dimethyl-4-morpholin-4-yl-phenyl)-propionamide;
3-Cyclopentyl-N-(2,6-dimethyl-4-morpholin-4-yl-phenyl)-propionamide;
N-(2,6-Dimethyl-4-morpholin-4-yl-phenyl)-2-(4-fluoro-phenyl)-acetamide;
N-(2,6-Dimethyl-4-morpholin-4-yl-phenyl)-2-thiophen-2-yl-acetamide;
N-(2,6-Dimethyl-4-morpholin-4-yl-phenyl)-3,3-dimethyl-butyramide;
Hexanoic acid (2,6-dimethyl-4-morpholin-4-yl-phenyl)-amide;
2-Cycloheptyl-N-(2,6-dimethyl-4-morpholin-4-yl-phenyl)-acetamide;
(2,6-Dimethyl-4-morpholin-4-yl-phenyl)-carbamic acid benzyl ester;
(2,6-Dimethyl-4-morpholin-4-yl-phenyl)-carbamic acid 2-chloro-benzyl ester;
3,5,5-Trimethyl-hexanoic acid (2,6-dimethyl-4-morpholin-4-yl-phenyl)-amide;
Octanoic acid (2,6-dimethyl-4-morpholin-4-yl-phenyl)-amide;
Heptanoic acid (2,6-dimethyl-4-morpholin-4-yl-phenyl)-amide;
N-(2,6-Dimethyl-4-morpholin-4-yl-phenyl)-2-phenyl-acetamide 2-(3,4-Dichloro-phenyl)-N-(2,6-dimethyl-4-morpholin-4-yl-phenyl)-acetamide;
2-(4-Allyloxy-3-chloro-phenyl)-N-(2,6-dimethyl-4-morpholin-4-yl-phenyl)-acetamide;
N-(2,6-Dimethyl-4-morpholin-4-yl-phenyl)-2-(3-trifluoromethyl-phenyl)-acetamide;
N-(2,6-Dimethyl-4-morpholin-4-yl-phenyl)-2-naphthalen-2-yl-acetamide;
3-(3-Chloro-phenyl)-N-(2,6-dimethyl-4-morpholin-4-yl-phenyl)-propionamide;
N-(2,6-Dimethyl-4-morpholin-4-yl-phenyl)-2-(3,4-dimethyl-phenyl)-acetamide;
2-(3-Bromo-phenyl)-N-(2,6-dimethyl-4-morpholin-4-yl-phenyl)-acetamide;
2-(3-Chloro-phenyl)-N-(2,6-dimethyl-4-morpholin-4-yl-phenyl)-acetamide;
N-(2,6-Dimethyl-4-morpholin-4-yl-phenyl)-2-p-tolyl-acetamide;
N-(2,6-Dimethyl-4-morpholin-4-yl-phenyl)-2-m-tolyl-acetamide;
2-(3,4-Difluoro-phenyl)-N-(2,6-dimethyl-4-morpholin-4-yl-phenyl)-acetamide;
N-(2,6-Dimethyl-4-morpholin-4-yl-phenyl)-2-(3-fluoro-phenyl)-acetamide;
N-(2-Bromo-4-morpholin-4-yl-6-trifluoromethyl-phenyl)-3-cyclohexyl-propionamide;
N-(2-Bromo-4-morpholin-4-yl-6-trifluoromethyl-phenyl)-2-(3-fluoro-phenyl)-acetamide;
N-(2-Bromo-4-morpholin-4-yl-6-trifluoromethyl-phenyl)-propionamide;
N-(2-Bromo-4-morpholin-4-yl-6-trifluoromethyl-phenyl)-butyramide;
N-(2-Chloro-4-morpholin-4-yl-6-trifluoromethyl-phenyl)-2-(3-fluoro-phenyl)-acetamide;
N-(2-Chloro-4-morpholin-4-yl-6-trifluoromethyl-phenyl)-2-cyclopentyl-acetamide;
2-Cyclopentyl-N-{2,6-dimethyl-4-[2-(4-trifluoromethyl-phenyl)-morpholin-4-yl]-phenyl}-acetamide;
N-{4-[2-(2-Chloro-phenyl)-morpholin-4-yl]-2,6-dimethyl-phenyl}-2-cyclopentyl-acetamide;
2-Cyclopentyl-N-{4-[2-(4-fluoro-phenyl)-morpholin-4-yl]-2,6-dimethyl-phenyl}-acetamide;
2-(2-Chloro-phenyl)-N-(2,6-dimethyl-4-morpholin-4-yl-phenyl)-acetamide;
Pentanoic acid (2,6-dimethyl-4-morpholin-4-yl-phenyl)-amide;
4-Methyl-pentanoic acid (2,6-dimethyl-4-morpholin-4-yl-phenyl)-amide;
2-Cyclopent-2-enyl-N-(2,6-dimethyl-4-morpholin-4-yl-phenyl)-acetamide;
5-Methyl-hexanoic acid (2,6-dimethyl-4-morpholin-4-yl-phenyl)-amide;
3-Methyl-pentanoic acid (2,6-dimethyl-4-morpholin-4-yl-phenyl)-amide;
Hex-5-enoic acid (2,6-dimethyl-4-morpholin-4-yl-phenyl)-amide;
3-Ethyl-pentanoic acid (2,6-dimethyl-4-morpholin-4-yl-phenyl)-amide;
2-Cyclopentyl-N-(4-morpholin-4-yl-2-pyridin-3-yl-6-trifluoromethyl-phenyl)-acetamide;
2-Cyclopentyl-N-(5-morpholin-4-yl-3-trifluoromethyl-biphenyl-2-yl)-acetamide;
2-Cyclopentyl-N-(4'-fluoro-5-morpholin-4-yl-3-trifluoromethyl-biphenyl-2-yl)-acetamide;
2-Cyclopentyl-N-(4'-methyl-5-morpholin-4-yl-3-trifluoromethyl-biphenyl-2-yl)-acetamide;
2-Cyclopentyl-N-(3'-methyl-5-morpholin-4-yl-3-trifluoromethyl-biphenyl-2-yl)-acetamide;
2-Cyclopentyl-N-(3',4'-difluoro-5-morpholin-4-yl-3-trifluoromethyl-biphenyl-2-yl)-acetamide;
2-(4-Fluoro-phenyl)-N-(4-morpholin-4-yl-2-pyridin-3-yl-6-trifluoromethyl-phenyl)-acetamide;
2-Cyclopentyl-N-(2,6-diethyl-4-morpholin-4-yl-phenyl)-acetamide;
2-Cyclopentyl-N-(2,6-diisopropyl-4-morpholin-4-yl-phenyl)-acetamide;
2-Cyclopentyl-N-(2,6-difluoro-4-morpholin-4-yl-phenyl)-acetamide;
Hexanoic acid (2,6-difluoro-4-morpholin-4-yl-phenyl)-amide;
N-(2,6-Difluoro-4-morpholin-4-yl-phenyl)-3,3-dimethyl-butyramide;
N-(2,6-Difluoro-4-morpholin-4-yl-phenyl)-2-(3-fluoro-phenyl)-acetamide;
2-Cyclopent-2-enyl-N-(2,6-difluoro-4-morpholin-4-yl-phenyl)-acetamide;
2-Bicyclo[2.2.1]hept-2-yl-N-(2,6-difluoro-4-morpholin-4-yl-phenyl)-acetamide;
2-Bicyclo[2.2.1]hept-2-yl-N-(2-methyl-4-morpholin-4-yl-6-trifluoromethyl-phenyl)-acetamide;
5-Methyl-pentanoic acid (2-methyl-4-morpholin-4-yl-6-trifluoromethyl-phenyl)-amide;
5-Methyl-hexanoic acid (2-methyl-4-morpholin-4-yl-6-trifluoromethyl-phenyl)-amide;

2-Cyclopent-2-enyl-N-(2-methyl-4-morpholin-4-yl-6-trifluoromethyl-phenyl)-acetamide;
2-Cyclopentyl-N-(2-methyl-4-morpholin-4-yl-6-trifluoromethyl-phenyl)-acetamide;
Hexanoic acid (2-methyl-4-morpholin-4-yl-6-trifluoromethyl-phenyl)-amide;
3,3-Dimethyl-N-(2-methyl-4-morpholin-4-yl-6-trifluoromethyl-phenyl)-butyramide;
2-(3,4-Difluoro-phenyl)-N-(2-methyl-4-morpholin-4-yl-6-trifluoromethyl-phenyl)-acetamide;
Hexanoic acid (2-methoxy-6-methyl-4-morpholin-4-yl-phenyl)-amide;
2-Cyclopentyl-N-(2-methoxy-6-methyl-4-morpholin-4-yl-phenyl)-acetamide;
N-(2-Methoxy-6-methyl-4-morpholin-4-yl-phenyl)-3,3-dimethyl-butyramide;
2-(3,4-Difluoro-phenyl)-N-(2-methoxy-6-methyl-4-morpholin-4-yl-phenyl)-acetamide;
2-Cyclopent-2-enyl-N-(2-methoxy-6-methyl-4-morpholin-4-yl-phenyl)-acetamide;
2-(3-Fluoro-phenyl)-N-(2-methoxy-6-methyl-4-morpholin-4-yl-phenyl)-acetamide;
2-Bicyclo[2.2.1]hept-2-yl-N-(2-methoxy-6-methyl-4-morpholin-4-yl-phenyl)-acetamide;
4-Methyl-pentanoic acid (2-methoxy-6-methyl-4-morpholin-4-yl-phenyl)-amide;
5-Methyl-hexanoic acid (2-methoxy-6-methyl-4-morpholin-4-yl-phenyl)-amide;
N-(2-Chloro-6-methyl-4-morpholin-4-yl-phenyl)-2-(3-fluoro-phenyl)-acetamide; and
N-(2-Chloro-6-methyl-4-morpholin-4-yl-phenyl)-2-cyclopentyl-acetamide.

11. The method according to claim 1, wherein the anticonvulsive is selected from the group consisting of retiagabine, carbamazepine, sodium valproate, lamotrigine, gabapentin, pregabalin, ethosuximide, levetiracetam, phenyloin, topiramate and zonisamide.

* * * * *